US011453713B2

(12) United States Patent
Landgraf et al.

(10) Patent No.: US 11,453,713 B2
(45) Date of Patent: *Sep. 27, 2022

(54) INSERTABLE VARIABLE FRAGMENTS OF ANTIBODIES AND MODIFIED A1-A2 DOMAINS OF NKG2D LIGANDS

(71) Applicant: XYPHOS BIOSCIENCES INC., South San Francisco, CA (US)

(72) Inventors: Kyle Landgraf, Alameda, CA (US); Daniel P. Steiger, San Francisco, CA (US); Steven R. Williams, San Francisco, CA (US); David W. Martin, Mill Valley, CA (US)

(73) Assignee: XYPHOS BIOSCIENCES INC., South San Francisco, CA (US)

(*) Notice: Subject to any disclaimer, the term of this patent is extended or adjusted under 35 U.S.C. 154(b) by 1042 days.

This patent is subject to a terminal disclaimer.

(21) Appl. No.: 14/959,745

(22) Filed: Dec. 4, 2015

(65) Prior Publication Data

US 2016/0159882 A1 Jun. 9, 2016

Related U.S. Application Data

(60) Provisional application No. 62/088,456, filed on Dec. 5, 2014.

(51) Int. Cl.
| | | |
|---|---|---|
| C07K 14/74 | (2006.01) | |
| C07K 14/705 | (2006.01) | |
| A61K 38/17 | (2006.01) | |
| C07K 16/28 | (2006.01) | |
| A61K 39/39 | (2006.01) | |
| C07K 16/32 | (2006.01) | |
| C07K 16/40 | (2006.01) | |
| C12N 5/0783 | (2010.01) | |
| A61K 38/00 | (2006.01) | |
| A61K 39/00 | (2006.01) | |

(52) U.S. Cl.
CPC ........ *C07K 14/70539* (2013.01); *A61K 39/39* (2013.01); *C07K 16/2818* (2013.01); *C07K 16/2851* (2013.01); *C07K 16/2863* (2013.01); *C07K 16/32* (2013.01); *C07K 16/40* (2013.01); *A61K 38/00* (2013.01); *A61K 2039/505* (2013.01); *C07K 2317/31* (2013.01); *C07K 2317/622* (2013.01); *C07K 2317/73* (2013.01); *C07K 2317/92* (2013.01); *C07K 2317/94* (2013.01); *C07K 2318/20* (2013.01); *C07K 2319/32* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 10,259,858 B2* | 4/2019 | Landgraf | C07K 14/7056 |
| 11,117,969 B2* | 9/2021 | Landgraf | C07K 16/2827 |
| 2003/0147847 A1 | 8/2003 | Cosman et al. | |
| 2012/0295288 A1 | 11/2012 | Yu et al. | |
| 2014/0302072 A1 | 10/2014 | Martin, Jr. et al. | |

FOREIGN PATENT DOCUMENTS

| | | |
|---|---|---|
| JP | 2014-504861 A | 2/2014 |
| RU | 2444570 C1 | 3/2012 |
| WO | 2012/091756 A1 | 7/2012 |

OTHER PUBLICATIONS

Finlay and McFadden (Cell, 2006, 124: 767-782) (Year: 2006).*
Doubrovina etal (J. Immuno. 2003, 171: 6891-6899) (Year: 2003).*
Strong and McFarland (Adv. Prot. Chem. 2004, 68: 281-312) (Year: 2004).*
Database "Subname: Full =MHC class I chain-related antigen MICH2 {ECO: 0000313|EMBL:AAK53892.1}; Flags: Fragment;" 1 page, Feb. 15, 2005, XP002778828, [retrieved from EBI accession No. UNIPROT:Q5JCT8].
McFarland, B., et al., "Symmetry Recognizing Asymmetry: Analysis of the Interactions between the C-Type Lectin-like Immunoreceptor NKG2D and MHC Class I-like Ligands", Structure, vol. 11, No. 4, pp. 411-422, Apr. 1, 2003, XP055456047.
Henager, S., et al., "Combining different design strategies for rational affinity maturation of the MICA-NKG2

FIGURE 11

Figure 12A
Figure 12B
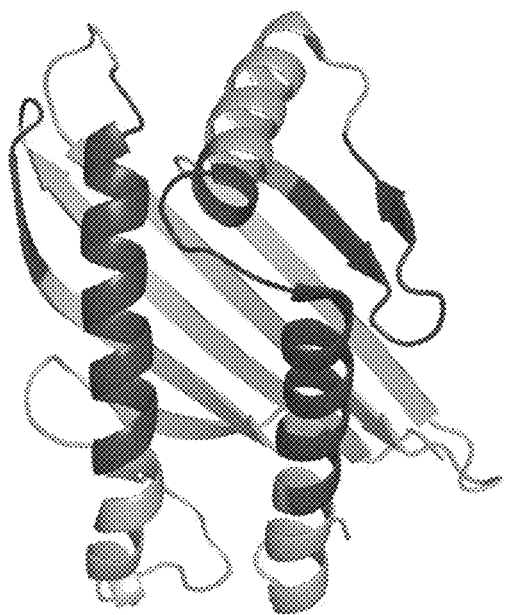
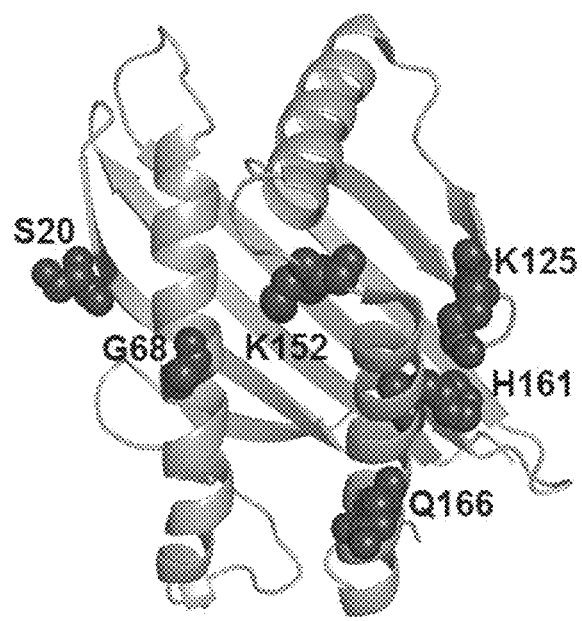

FIGURE 18

Figure 22A
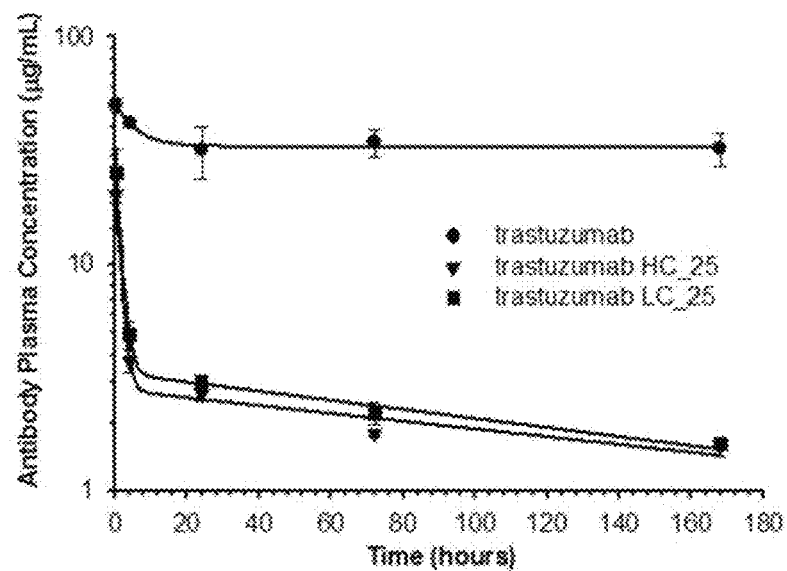
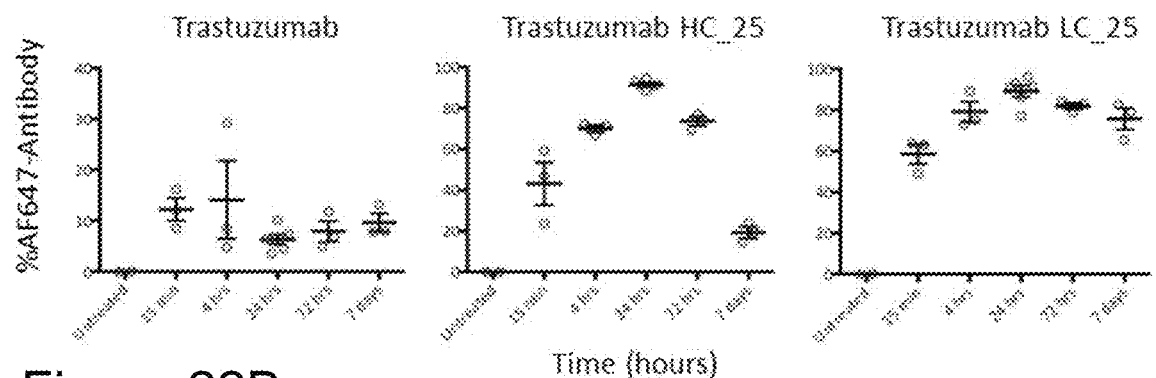
Figure 22B

US 11,453,713 B2

INSERTABLE VARIABLE FRAGMENTS OF ANTIBODIES AND MODIFIED A1-A2 DOMAINS OF NKG2D LIGANDS

BACKGROUND OF THE INVENTION

1. Field of the Invention

This application relates generally to the production of polypeptides having specific antigen-binding properties of Fv domains, for example, insertable variable fragments of antibodies, and modified α1-α2 domains of NKG2D ligands.

2. Background Information

An antibody (Ab), FIG. 1, also known as an immunoglobulin (Ig), in many mammals including humans is a large, Y-shape protein used by the immune system to identify and neutralize foreign objects such as bacteria and viruses (Charles Janeway (2001). *Immunobiology*. (5th ed.), Chapter 3. Garland Publishing. ISBN 0-8153-3642-X. (electronic full text via NCBI Bookshelf). The antibody recognizes a unique part of the foreign target, called an antigen. Each tip of the two arms of the "Y" of an antibody contains an antigen binding site, or a paratope, (a structure analogous to a lock) that is specific for one particular epitope (similarly analogous to a key) of an antigen, allowing these two structures to bind together with precision. Using this binding mechanism, an antibody can tag a microbe or an infected cell for attack by other parts of the immune system or can neutralize its target directly, for example, by blocking a part of a microbe that is essential for its invasion and survival. The production of antibodies is the main function of the humoral, or "adaptive", immune system. Antibodies are secreted by plasma cells. Antibodies in nature can occur in two physical forms, a soluble form that is secreted from the cell, and a membrane-bound form that is attached to the surface of a B cell via the "stem" of the Y.

Antibodies are glycoproteins belonging to the immunoglobulin superfamily and are typically made of basic structural units—each with two large heavy chains and two small light chains. There are several different types of antibody heavy chains, and several different kinds of antibodies, which are grouped into different isotypes based on which heavy chain they possess. Five different antibody isotypes are known in mammals (Market E, Papavasiliou F N (October 2003). "V(D)J recombination and the evolution of the adaptive immune system". *PLoS Biol.* 1 (1): E16. doi: 10.1371/journal.pbio.0000016. PMC 212695. PMID 14551913). Although the general structure of all antibodies is very similar, a small region at the tip of each arm of the Y-shaped protein is extremely variable, allowing millions of antibodies with slightly different tip structures, or antigen-binding sites, to exist. This region is known as the hypervariable or variable region. Each of these natural variants can bind to a different antigen. This enormous diversity of antibodies allows the immune system to adapt and recognize an equally wide variety of antigens (Hozumi N, Tonegawa S (1976). "Evidence for somatic rearrangement of immunoglobulin genes coding for variable and constant regions". *Proc. Natl. Acad. Sci. U.S.A.* 73 (10): 3628-3632. doi: 10.1073/pnas.73.10.3628. PMC 431171. PMID 824647.)

The natural "Y"-shaped Ig molecule consists of four polypeptide chains; two identical heavy chains and two identical light chains connected by disulfide bonds, FIG. 1. Each heavy chain has two major regions, the constant region (CH) and the variable region (VH). The constant region is essentially identical in all antibodies of the same isotype, but differs in antibodies of different isotypes. A light chain also has two successive domains: a smaller constant region (CL) and the variable region (VL) (Woof J, Burton D (2004). "Human antibody-Fc receptor interactions illuminated by crystal structures." *Nat Rev Immunol* 4 (2): 89-99. doi: 10.1038/nri1266. PMID 15040582).

Some parts of an antibody have the same functions. Each of the two arms of the Y, for example, contains the sites that can bind to antigens and, therefore, recognize specific foreign objects. This region of the antibody is called the Fv (fragment, variable) region. It is composed of one variable domain from the heavy chain ($V_H$) and one variable region from the light chain ($V_L$) of the antibody (Hochman J, Inbar D, Givol D (1973). An active antibody fragment (Fv) composed of the variable portions of heavy and light chains. *Biochemistry* 12 (6): 1130-1135. doi:10.1021/bi00730a018. PMID 4569769). The paratope is shaped at one end of the Fv and is the region for binding to antigens. It is comprised of variable loops of β-strands, three each on the $V_L$ and on the $V_H$ and is responsible for binding to the antigen, FIG. 2. These 6 loops are referred to as the complementarity determining regions (CDRs) (North B, Lehmann A, Dunbrack R L (2010). "A new clustering of antibody CDR loop conformations". *J Mol Biol* 406 (2): 228-256. doi:10.1016/j.jmb.2010.10.030. PMC 3065967. PMID 21035459).

Useful polypeptides that possess specific antigen binding function can be derived from the CDRs of the variable regions of antibodies. These two antibody variable domains, one of the light chain (VL) and one from the heavy chain ($V_H$), each with 3 CDRs can be fused in tandem, in either order, using a single, short linker peptide of 10 to about 25 amino acids to create a linear single-chain variable fragment (scFv) polypeptide comprising one each of heavy and light chain variable domains, FIG. 3 (Bird, R. E., Hardman, K. D., Jacobson, J. W., Johnson, S., Kaufman, B. M., Lee, S. M., Lee, T., Pope, S. H., Riordan, G. S., and Whitlow, M. (1988) Single-chain antigen-binding proteins, *Science* 242, 423-426; Huston, J. S., Levinson, D, Mudgett-Hunter, M, Tai, M-S, Novotny, J, Margolies, M. N., Ridge, R., Bruccoleri, R E., Haber, E., Crea, R., and Opperman, H. (1988). Protein engineering of antibody binding sites: Recovery of specific activity in an anti-digoxin single-chain Fv analogue produced in *Escherichia coli*. PNAS 85: 5879-5883).

The linker is usually rich in glycine for flexibility, as well as serine, threonine, or charged amino acids for solubility, and can either connect the N-terminus of the $V_H$ with the C-terminus of the $V_L$, or vice versa. This protein retains the specificity of the original immunoglobulin, despite removal of the constant regions and the introduction of the single linker. This format enables one ordinarily skilled in the art of recombinant DNA technology to genetically fuse the linear scFv to the N- or C-terminus of a parent protein in order to impart to the parent protein the antigen binding properties of the scFv. There are numerous other proposed or created arrangements of polyvalent and tandem scFv regions, but importantly as described below, all have at least two spatially distant termini, FIG. 4 (Le Gall, F.; Kipriyanov, S M; Moldenhauer, G; Little, M (1999). "Di-, tri- and tetrameric single chain Fv antibody fragments against human CD19: effect of valency on cell binding". *FEBS Letters* 453 (1): 164-168. doi:10.1016/50014-5793(99) 00713-9. PMID 10403395).

SUMMARY OF THE INVENTION

The present disclosure relates to modified α1-α2 domains of NKG2D ligands attached to polypeptides, in some embodiments antibodies or fragments of antibodies. In some aspects, the present disclosure relates to antigen-binding peptides derived from light and heavy chain antibody variable domains, which contain two linker regions and a split variable domain.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A shows the structure of variable light (VL) and variable heavy (VH) domains from FGFR3-binding antibody showing the domain topology of the iFv format. Grey arrows represent the 2 linker regions (LR), one and only one of which is used traditionally to connect the termini of VL and VH to create an scFv. The LR with a dotted border connected the C-terminus of VL to the N-terminus of VH (visible behind the molecule). The LR with a solid border connected the C-terminus of VH to the N-terminus of VL. Segments of the split VL domain are labeled Nt and Ct as described in text. As a result of the creation of non-natural pair of N- and C-termini between strand 1 (S1) and strand 2 (S2) the VL has been divided into an N-terminal segment (VLN) and a C-terminal segment (VLC). The 6 CDRs of VL and VH are represented as the loops at the top of the figure. FIG. 5B shows the scheme of the domain layout for inserting an iFv into loop 1 (L1) of MICA-α3 with or without a spacer region (SR). An iFv could also be similarly inserted into loop 2 (L2) and/or loop 3 (L3).

FIG. 11. NK-mediated target cell lysis assays. NKL effector cells were co-incubated with calcein-loaded, FGFR3-expressing P815 target cells at a effector:target ratio of 15:1. Increasing concentrations of a negative control MICA (sMICA) had no effect on target cell lysis, whereas each indicated NKG2DL-α3-iFv.2 protein stimulated target cell lysis.

FIGS. 12A and 12B. Structure-directed mutagenesis of the α1-α2 domain of MICA for enhanced NKG2D affinity. FIG. 12A shows the structure of the α1-α2 domain of MICA (PDB 1HYR) with the NKG2D-binding surface mapped to 57 residues colored dark grey. FIG. 12B shows six positions that were identified as key sites for NKG2D affinity mutations. The wild-type amino acid residues are labeled and their side chains shown in dark grey spheres.

FIG. 13A shows titration data for a panel of α1-α2 affinity variants (15-18), wild-type (WT), or WED soluble MICA proteins inhibiting human NKG2D-Fc binding to plate-coated MICA. FIG. 13B shows the same set of proteins in FIG. 13A titrated against mouse NKG2D-Fc. In both assays variants 15, 16, 17, and 18 display $IC_{50}$ values significantly less than both WT and WED proteins. The equilibrium $IC_{50}$ values are shown in Table 3.

FIG. 18. Protein sequence alignment of α1-α2 domains from MICA and ULBPs (SEQ ID NOs.: 77-83). Amino acids highlighted in grey were selected for NNK mutagenesis in ULBP2 (60 amino acids) and ULBP3 (36 amino acids). Residues highlighted in black were identified as key positions for selected and identified as mutations that modulate binding affinity to NKG2D (Tables 6 and 7).

FIG. 19A depicts experiments in which ULBP2 variants displayed on phage were titrated against NKG2D and relative binding affinities were measured relative to native ULBP2 (WT, black circles). FIG. 19B depicts experiments in which ULBP3 variants displayed on phage were titrated against NKG2D and relative binding affinities were measured relative to native ULBP3 (WT, black circles).

FIGS. 22A and 22B. Trastuzumab-based fusions of variant 25 α1-α2 domain arm NK cells in vivo. Parent trastuzumab, trastuzumab HC_25 fusion, and trastuzumab LC_25 fusion were conjugated with Alexa Flour. Groups of three C57BL/6 mice were injected with a single dose of 100 μg of parent, HC fusion or LC fusion; and blood was drawn from each animal at indicated times for plasma PK ELISAs (FIG. 22A) and flow cytometric analyses of the fluorescently labeled molecules bound to peripheral NK cells (FIG. 22B).

DETAILED DESCRIPTION OF THE INVENTION

Figure 1:
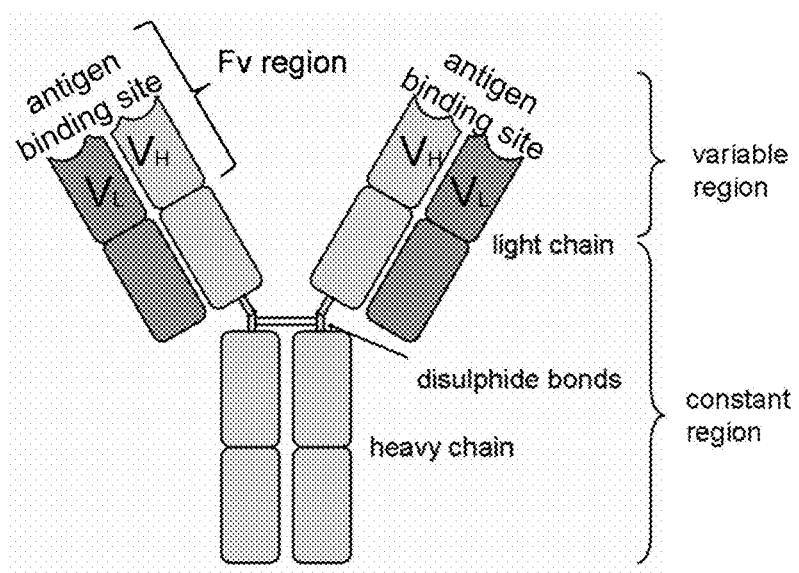
FIG. 1. A cartoon of a typical mammalian antibody showing its Y-shaped structure and structural components.
Figure 2:
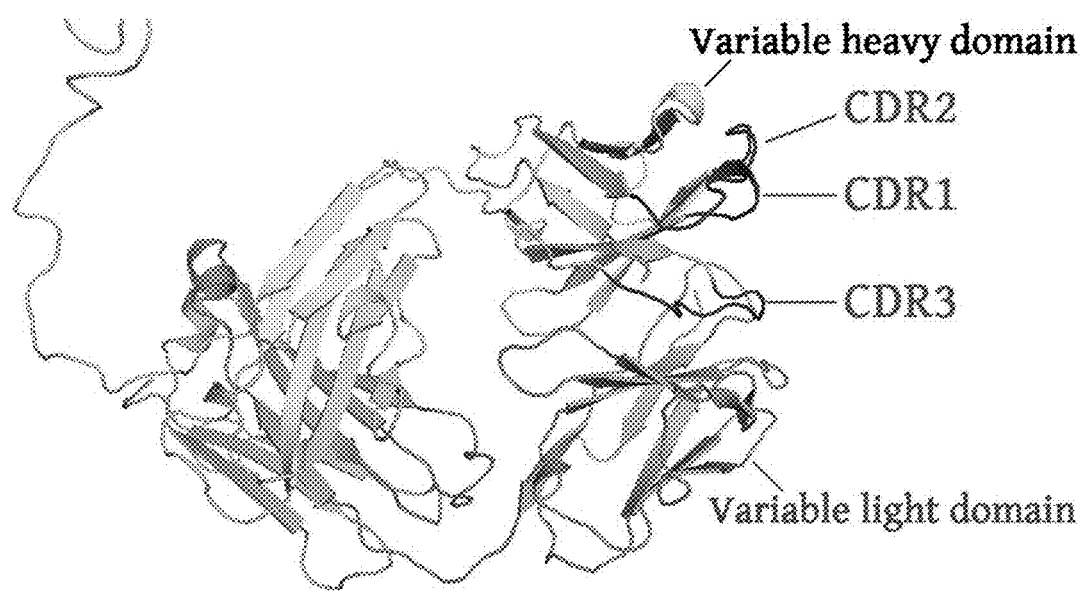
FIG. 2. A cartoon of the structure of an Fv region of a natural mammalian antibody showing the 3 labeled (Complementarity Determining Regions) CDRs of the $V_H$ and the 3 unlabeled loops of the $V_L$ CDRs, which form the paratope or antigen binding site.
Figure 3:
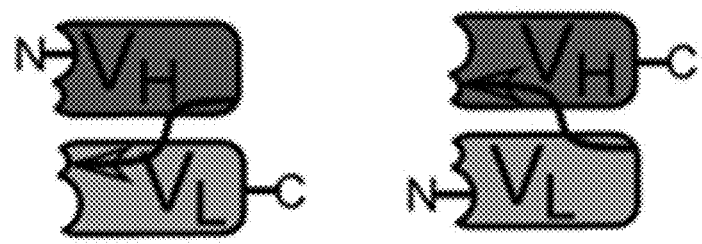
FIG. 3. A cartoon of the two possible structures of a single-chain variable fragment (scFv), with the antigen binding sites including the N-termini on the left and the C-termini on the right. The single linker region, or linker peptide, in each scFv is shown as an arrow.
Figure 4:
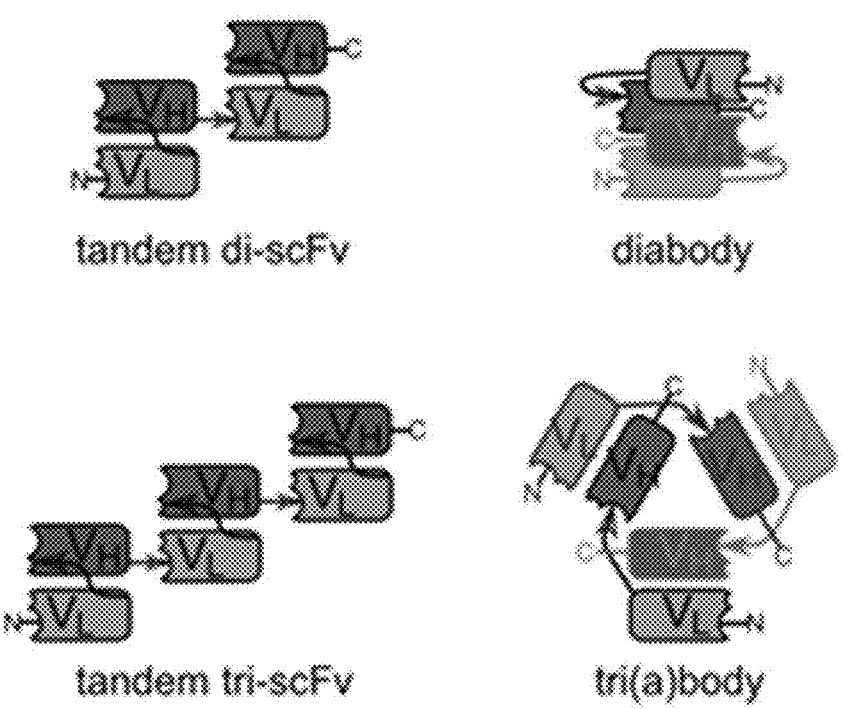
FIG. 4. Polyvalent single-chain variable fragments (scFv's). Structure of divalent (top) and trivalent (bottom) scFvs, tandem (left) and di-/trimerization format (right). Note that each has 2 or more spatially distant free termini.

In some aspects, the present invention relates to insertable variable fragment (iFv) peptides. Because the C-terminus and N-terminus of scFv molecules including polyvalent scFv structures are far apart spatially, scFv structures cannot be inserted into a loop region embedded within a protein fold of a parent or recipient protein without disrupting or destabilizing its fold(s) and/or without disrupting the Fv framework required to properly position the CDRs or hypervariable regions to retain their antigen-binding properties.

To insert the variable fragment of an antibody containing up to 6 CDRs into one or more loop regions of a nascent parent protein molecule without disrupting structural folds of the variable fragment or of the parent protein, we invented a new class of antigen-binding peptides derived from the light and heavy chain antibody variable domains. The new structures contained two linker regions, rather than the traditional single linker of scFv structures, plus a split variable domain. Conceptually the canonical termini of the variable light (VL) and heavy (VH) domains were fused into a continuous or "circular" peptide. That circular peptide structure containing all 6 CDRs of the Fv can then conceptually be split at one of several possible novel sites to create an insertable Fv (iFv). The non-natural split site can be created within either the light or the heavy chain variable domain at or near the apex or turn of a loop to create new, unique N- and C-termini spatially positioned proximal to each other, preferably within 0.5 to 1.5 nm, so as to be insertable into loops of other (parent or recipient) proteins or polypeptides without disrupting the structure, stability, or desirable function. This new class of peptides is called an insertable variable fragment (iFv). The binding or targeting specificity conveyed by an iFv to a recipient molecule can be changed by inserting into the recipient another or different iFV based on a different antibody or scFv or by replacing 1 or more of the CDRs of an existing insertable iFv.

The insertion of one or more iFv polypeptides exhibiting specific antigen-binding properties of Fv domains into other proteins and thereby imparting novel binding properties will have multiple utilities. Such uses include but are not limited to enabling the parent protein to bind the specific antigen, target the antigen, detect the presence of antigen, remove the antigen, contact or draw near the antigen, to deliver a payload to the antigen or antigen-expressing cell, recruit the antigen, and image the presence of the antigen. A payload could be conjugated directly to one or both the amino-terminus and carboxy-terminus of an iFv or indirectly to an iFv via a parent protein or peptide. Examples of payloads include but are not limited to a chromophore, a fluorophore, a pharmacophore, an atom, a heavy or radioactive isotope, an imaging agent, a chemotherapeutic agent, or a toxin. A payloaded iFv can be used to locate or identify the presence of a target molecule to which the iFv specifically binds and as such can serve as in vitro or in vivo imaging agents or diagnostic agents that are small and stable. In addition, to one or both the amino-terminus and carboxy-terminus of an iFv peptide a chemotherapeutic agent or toxic molecule can be conjugated in order to create an iFv-drug conjugate, for example, as treatment for a malignancy or infection. A single payload may be conjugated to both the amino-terminus and the carboxy-terminus of an iFv peptide so as to span or connect the two termini; such spanning may further stabilize the iFv by blocking the termini from exopeptidase degradation or protecting the iFv from denaturation or unfolding.

Examples of parent or recipient proteins or polypeptides that are candidates for insertions of iFv peptides include but are not limited to, proteins comprised of Ig folds or Ig domains, globulins, albumens, fibronectins and fibronectin domains, integrins, fluorescent proteins, enzymes, outer membrane proteins, receptor proteins, T-cell receptors, chimeric antigen receptors, viral antigens, virus capsids, viral ligands for cell receptors, high molecular weight bacteriocins, histones, hormones, knottins, cyclic peptides or polypeptides, major histocompatibility (MHC) family proteins, MIC proteins, lectins, and ligands for lectins. It is also possible to insert iFv structures into non-protein recipient molecules such a polysaccharides, dendrimers, polyglycols, peptidoglycans, antibiotics, and polyketides.

Natural killer (NK) cells and certain (CD8+ αβ and γδ) T-cells of the immunity system have important roles in humans and other mammals as first-line, innate defense against neoplastic and virus-infected cells (Cerwenka, A., and L. L. Lanier. 2001. NK cells, viruses and cancer. Nat. Rev. Immunol. 1:41-49). NK cells and certain T-cells exhibit on their surfaces NKG2D, a prominent, homodimeric, surface immunoreceptor responsible for recognizing a target cell and activating the innate defense against the pathologic cell (Lanier, L L, 1998. NK cell receptors. Ann. Rev. Immunol. 16: 359-393; Houchins J P et al. 1991. DNA sequence analysis of NKG2, a family of related cDNA clones encoding type II integral membrane proteins on human NK cells. J. Exp. Med. 173: 1017-1020; Bauer, S et al., 1999. Activation of NK cells and T cells by NKG2D, a receptor for stress-inducible MICA. Science 285: 727-730). The human NKG2D molecule possesses a C-type lectin-like extracellular domain that binds to its cognate ligands, the 84% sequence identical or homologous, monomeric MICA and MICB, polymorphic analogs of the Major Histocompatibility Complex (MHC) Class I chain-related glycoproteins (MIC) (Weis et al. 1998. The C-type lectin superfamily of the immune system. Immunol. Rev. 163: 19-34; Bahram et al. 1994. A second lineage of mammalian MHC class I genes. PNAS 91:6259-6263; Bahram et al. 1996a. Nucleotide sequence of the human MHC class I MICA gene. Immunogenetics 44: 80-81; Bahram and Spies T A. 1996. Nucleotide sequence of human MHC class I MICB cDNA. Immunogenetics 43: 230-233). Non-pathologic expression of MICA and MICB is restricted to intestinal epithelium, keratinocytes, endothelial cells and monocytes, but aberrant surface expression of these MIC proteins occurs in response to many types of cellular stress such as proliferation, oxidation and heat shock and marks the cell as pathologic (Groh et al. 1996. Cell stress-regulated human MHC class I gene expressed in GI epithelium. PNAS 93: 12445-12450; Groh et al. 1998. Recognition of stress-induced MHC molecules by intestinal γδT cells. Science 279: 1737-1740; Zwirner et al. 1999. Differential expression of MICA by endothelial cells, fibroblasts, keratinocytes and monocytes. Human Immunol. 60: 323-330). Pathologic expression of MIC proteins also seems involved in some autoimmune diseases (Ravetch, J V and Lanier L L. 2000. Immune Inhibitory Receptors. Science 290: 84-89; Burgess, S J. 2008. Immunol. Res. 40: 18-34). The differential regulation of NKG2D ligands, such as the polymorphic MICA and MICB, is important to provide the immunity system with a means to identify and respond to a broad range of emergency cues while still protecting healthy cells from unwanted attack (Stephens H A, (2001) MICA and MICB genes: can the enigma of their polymorphism be resolved? Trends Immunol. 22: 378-85; Spies, T. 2008. Regulation of NKG2D ligands: a purposeful but delicate affair. Nature Immunol. 9: 1013-1015).

Viral infection is a common inducer of MIC protein expression and identifies the viral-infected cell for NK or T-cell attack (Groh et al. 1998; Groh et al. 2001. Co-stimulation of CD8+ αβT-cells by NKG2D via engagement by MIC induced on virus-infected cells. Nat. Immunol. 2: 255-260; Cerwenka, A., and L. L. Lanier. 2001). In fact, to avoid such an attack on its host cell, cytomegalovirus and other viruses have evolved mechanisms that prevent the expression of MIC proteins on the surface of the cell they infect in order to escape the wrath of the innate immunity system (Lodoen, M., K. Ogasawara, J. A. Hamerman, H. Arase, J. P. Houchins, E. S. Mocarski, and L. L. Lanier. 2003. NKG2D-mediated NK cell protection against cytomegalovirus is impaired by gp40 modulation of RAE-1 molecules. J. Exp. Med. 197:1245-1253; Stern-Ginossar et al., (2007) Host immune system gene targeting by viral miRNA. Science 317: 376-381; Stern-Ginossar et al., (2008) Human microRNAs regulate stress-induced immune responses mediated by the receptor NKG2D. Nature Immunology 9: 1065-73; Slavuljica, I A Busche, M Babic, M Mitrovic, I Gašparovic, D Cekinovic, E Markova Car, E P Pugel, A Cikovic, V J Lisnic, W J Britt, U Koszinowski, M Messerle, A Krmpotic and S Jonjic. 2010. Recombinant mouse cytomegalovirus expressing a ligand for the NKG2D receptor is attenuated and has improved vaccine properties. J. Clin. Invest. 120: 4532-4545).

In spite of their stress, many malignant cells, such as those of lung cancer and glioblastoma brain cancer, also avoid expression of MIC proteins and as a result may be particularly aggressive as they too escape the innate immunity system (Busche, A et al. 2006, NK cell mediated rejection of experimental human lung cancer by genetic over expression of MHC class I chain-related gene A. Human Gene Therapy 17: 135-146; Doubrovina, E S, MM Doubrovin, E Vider, R B Sisson, R J O'Reilly, B Dupont, and Y M Vyas, 2003. Evasion from NK Cell Immunity by MHC Class I Chain-Related Molecules Expressing Colon Adenocarcinoma (2003) J. Immunology 6891-99; Friese, M. et al. 2003. MICA/NKG2D-mediated immunogene therapy of experimental gliomas. Cancer Research 63: 8996-9006; Fuertes, M B, M V Girart, L L Molinero, C I Domaica, L E Rossi, M M Barrio, J Mordoh, G A Rabinovich and N W Zwirner. (2008) Intracellular Retention of the NKG2D Ligand MHC Class I Chain-Related Gene A in Human Melanomas Confers Immune Privilege and Prevents NK Cell-Mediated Cytotoxicity. J. Immunology, 180: 4606-4614).

The high resolution structure of human MICA bound to NKG2D has been solved and demonstrates that the α3 domain of MICA has no direct interaction with the NKG2D (Li et al. 2001. Complex structure of the activating immunoreceptor NKG2D and its MHC class I-like ligand MICA. Nature Immunol. 2: 443-451; Protein Data Bank accession code 1HYR). The α3 domain of MICA, like that of MICB, is connected to the α1-α2 platform domain by a short, flexible linker peptide, and itself is positioned naturally as "spacer" between the platform and the surface of the MIC expressing cell. The 3-dimensional structures of the human MICA and MICB α3 domains are nearly identical (root-mean square distance <1 Å on 94 C-αα's) and functionally interchangeable (Holmes et al. 2001. Structural Studies of Allelic Diversity of the MHC Class I Homolog MICB, a Stress-Inducible Ligand for the Activating Immunoreceptor NKG2D. J Immunol. 169: 1395-1400).

As used herein, a "soluble MIC protein", "soluble MICA" and "soluble MICB" refer to a MIC protein containing the α1, α2, and α3 domains of the MIC protein but without the transmembrane or intracellular domains.

The α1-α2 platform domain of a soluble MIC protein is tethered to the α3 domain and is diffusible in the intercellular or intravascular space of the mammal. Preferably the α1-α2 platform domains of the non-natural MIC proteins of the invention are at least 80% identical or homologous to a native or natural α1-α2 domain of a human MICA or MICB protein and bind NKG2D. In some embodiments, the α1-α2 platform domain is 85% identical to a native or natural α1-α2 platform domain of a human MICA or MICB protein and binds NKG2D. In other embodiments, the α1-α2 platform domain is 90%, 95%, 96%, 97%, 98%, or 99% identical to a native or natural α1-α2 platform domain of a human MICA or MICB protein and binds NKG2D.

In some embodiments, a heterologous peptide tag may be fused to the N-terminus or C-terminus of an α1-α2 domain or a soluble MIC protein to aid in the purification of the soluble MIC protein. Tag sequences include peptides such as a poly-histidine, myc-peptide or a FLAG tag. Such tags may be removed after isolation of the MIC molecule by methods known to one skilled in the art.

As used herein "peptide", "polypeptide", and "protein" are used interchangeably; and a "heterologous molecule", "heterologous peptide", "heterologous sequence" or "heterologous atom" is a molecule, peptide, nucleic acid or amino acid sequence, or atom, respectively, that is not naturally or normally found in physical conjunction with the subject molecule.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

All references cited herein are hereby incorporated by reference in their entireties, whether previously specifically incorporated or not. As used herein, the terms "a", "an", and "any" are each intended to include both the singular and plural forms.

Having now fully described the invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and may be applied to the essential features hereinbefore set forth.

EXAMPLES OF iFv AND OF MODIFIED α1-α2 DOMAINS OF NKG2D LIGANDS

Example 1 iFv

As specific examples, we synthesized a 1126 bp and a 1144 bp DNA fragment (SEQ ID NO:1 and 2, respectively) encoding in the following order: the α3 domain of human MICA (as a parent peptide) amino acid 182 to amino acid 194 (the beginning of loop 1 of the α3 domain), no spacer or a GGS amino acid spacer region (SR), an iFv peptide based on the structure of a Fibroblast Growth Factor Receptor 3 (FGFR3)-binding antibody (MAbR3; Qing, J., Du, X., Chen, Y., Chan, P., Li, H., Wu, P., Marsters, S., Stawicki, S., Tien, J., Totpal, K., Ross, S., Stinson, S., Dornan, D., French, D., Wang, Q. R., Stephan, J. P., Wu, Y., Wiesmann, C., and Ashkenazi, A. (2009) Antibody-based targeting of FGFR3 in bladder carcinoma and t(4; 14)-positive multiple myeloma in mice, *The Journal of clinical investigation* 119, 1216-1229.), no spacer or another GGS spacer region, the distal portion of loop 1 of the α3 domain starting at amino acid 196 and including the remaining carboxy-terminal portion of the α3 domain to amino acid 276 of a soluble MICA molecule. Each synthetic, double stranded DNA polynucleotide then encoded a polypeptide that contained 6 CDRs in the form of an iFv inserted into loop 1 of the α3 domain of MICA.

Figure 5A:
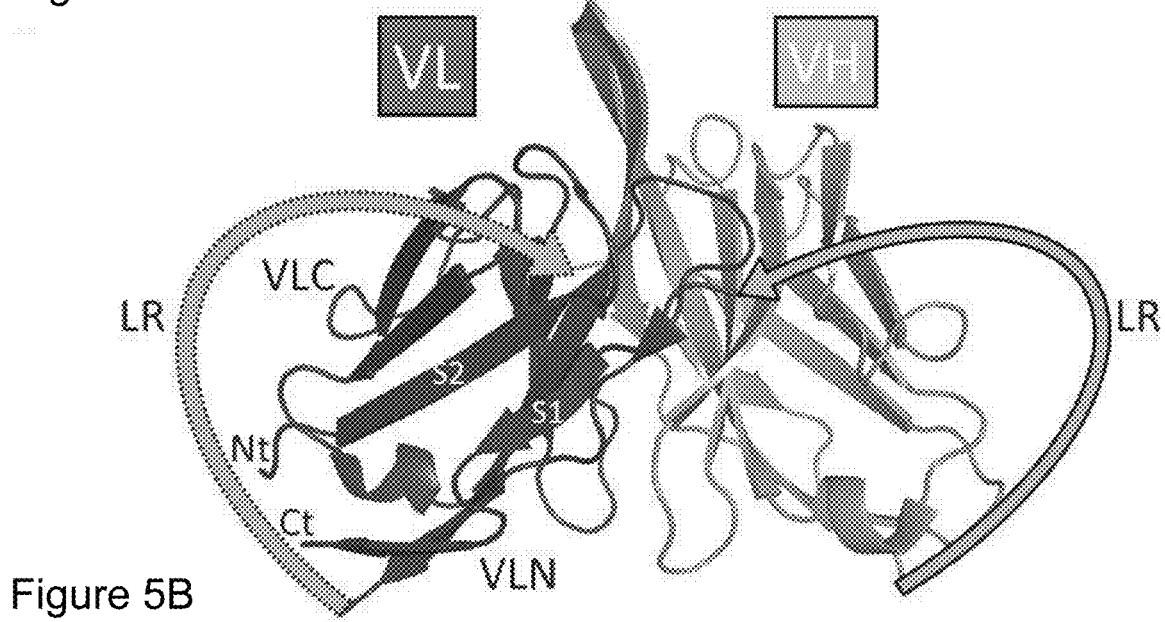
FIGS. 5A and 5B. Diagram of an insertable variable fragment, iFv. Diagram of an insertable variable fragment, iFv.
Figure 5B:
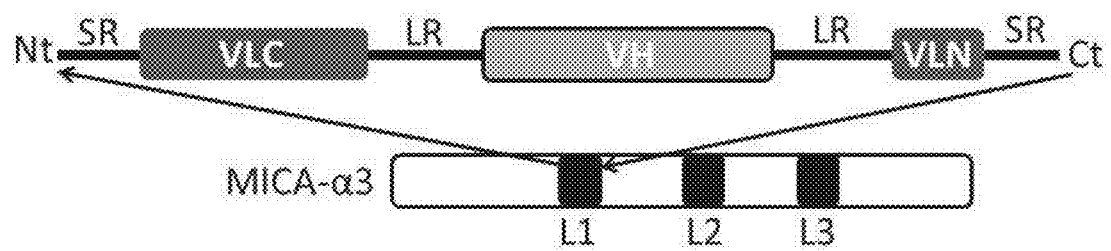

This iFv peptide itself (SEQ ID NO.:3), encoded by SEQ ID NO.:4, contained two identical, typical linker regions (LR) corresponding to residues GGSSRSSSSGGGGSGGGG (SEQ ID NO.:5) (Andris-Widhopf, J., Steinberger, P., Fuller, R., Rader, C., and Barbas, C. F., 3rd. (2011) Generation of human Fab antibody libraries: PCR amplification and assembly of light- and heavy-chain coding sequences, *Cold Spring Harbor protocols* 2011). One LR joined the C-terminus of VL to the N-terminus of the VH domain, and the second LR joined the C-terminus of the VH domain to the N-terminus of VL. Conceptually this new structure is the continuous or "circular" peptide referred to above and contained 6 CDRs of the starting Fv. The variable VL chain of the antibody was effectively split within the loop region between beta-strands 1 and 2 (S1 and S2) and thereby created a new N-terminal segment (VLN) and a new C-terminal segment (VLC) with an accompanying pair of new, non-natural C- and N-termini, respectively, FIG. 5A. This pair of termini created a sole site for attachment or conjugation of the iFv to the recipient molecule such as a protein. The schematic of the inserted iFv in the parent α3 domain is shown in FIG. 5B.

To produce the soluble MICA proteins with a heterologous iFv peptide inserted into the α3 domain we generated a baculoviral expression vector to accommodate the DNA sequences (SEQ ID NOs.:1 and 2) encoding the α3-iFv.1 (SEQ ID NO.:6) and α3-iFv.2 (SEQ ID NO.:7), respectively. The DNA fragments were amplified by PCR, digested using NcoI and EcoRI restriction enzymes, and subcloned into the baculoviral expression vector, SW403, replacing the wild-type α3 domain. SW403 is a baculoviral expression vector derived from pVL1393 (Invitrogen, Inc.) into which wild-type sMICA (residues 1-276) had previously been cloned using 5' BamHI and 3' EcoRI sites. The new expression vector was co-transfected with baculoviral DNA into SF9 insect cells, and baculovirus was grown for two amplification cycles and used to express the His-tagged MICA-α3-iFv proteins in T.ni insect cells according to manufacturer's protocol (Invitrogen). The expression was carried out in a 100 mL volume for three days and the growth medium was harvested for purification of the secreted soluble protein using Ni-affinity chromatography. Monomeric MICA-α3-iFv was purified to >90% purity with the expected molecular weight of 60.9 kDa as determined by SDS-PAGE. Functional characterization was carried out using binding ELISAs and in vitro target cell killing assays.

Figure 6:
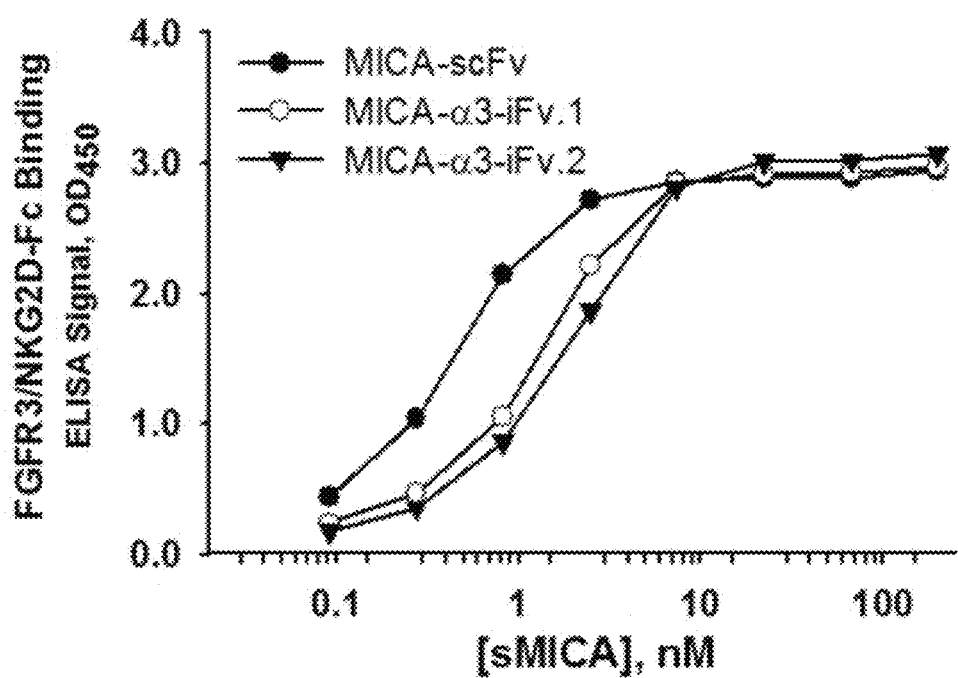
FIG. 6. Titration curves for the modified sMICA molecules binding to FGFR3 coated wells. Bound sMICA was detected by ELISA using NKG2D-Fc to confirm the bispecific activity. Both versions of the inserted variable fragments (MICA-α3-iFv.1 and MICA-α3-iFv.2) bound FGFR3 comparably to the C-terminal fusion of an scFv (MICA-scFv).

The purified MICA-α3-iFv proteins were tested in a FGFR3-binding ELISA to confirm simultaneous binding to the FGFR3 target and the NKG2D receptor. FGFR3 in phosphate buffered saline (PBS) was coated onto Maxisorp plates at 2 ug/ml concentration. Each MICA protein was titrated, allowed to bind FGFR3 for 1 hour, and washed to remove unbound sMICA protein. Bound MICA-α3-iFv protein was detected using NKG2D-Fc and anti-Fc-HRP conjugate. FIG. 6 shows that the binding of both MICA-α3-iFv.1 and MICA-α3-iFv.2 to FGFR3 was comparable to that of a MICA-scFv, made by fusing to the C-terminus of soluble MICA a traditional scFv constructed from MAbR3. These ELISA results also indicated that both the FGFR3 and NKG2D binding specificities of the scFv and the α1-α2 domain, respectively, were retained by the modified MICA and demonstrated that the iFv peptide inserted using different spacer formats was functional.

Figure 7A:
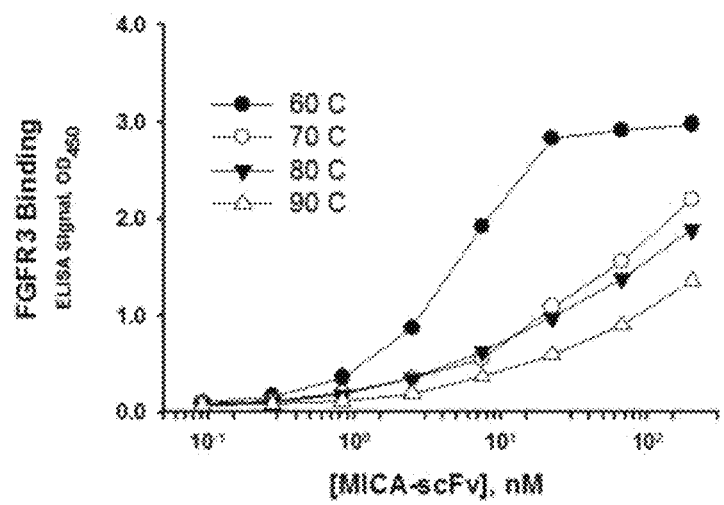
FIGS. 7A and 7B. Thermal stability of MICA-α3-iFv.2. ELISA titration curves of MICA-scFv (FIG. 7A) or MICA-α3-iFv.2 (FIG. 7B) binding to FGFR3-coated wells after exposure to the indicated temperatures (degrees Celsius) for 1 hour. The MICA-α3-iFv exhibited strong binding to FGFR3 after exposure to 80° C., whereas MICA-scFv lost significant activity after exposure to 70° C.
Figure 7B:
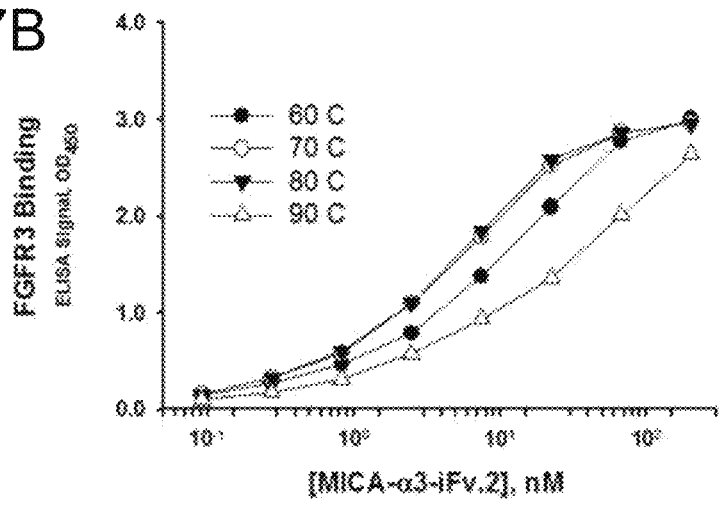

We tested and compared the thermal stability of sMICA-α3-iFv.2 to that of sMICA-scFv. Both proteins were subjected for 1 hr to increasing temperatures from 60-90° C. and then allowed to equilibrate to room temperature for 1 hour before being assayed for binding properties by ELISA. The results in FIGS. 7A and 7B showed that MICA-α3-iFv.2 can be subjected to temperatures as high as 80° C. with no loss in specific binding to FGFR3. The traditional MICA-scFv lost binding activity at 70° C. This result indicated that soluble MICA containing the invented iFv format is significantly more stable than terminal fusions of a traditional scFv (Miller, B. R., Demarest, S. J., Lugovskoy, A., Huang, F., Wu, X., Snyder, W. B., Croner, L. J., Wang, N., Amatucci, A., Michaelson, J. S., and Glaser, S. M. (2010) Stability engineering of scFvs for the development of bispecific and multivalent antibodies, *Protein engineering, design & selection: PEDS* 23, 549-557; Weatherill, E. E., Cain, K. L., Heywood, S. P., Compson, J. E., Heads, J. T., Adams, R., and Humphreys, D. P. (2012) Towards a universal disulphide stabilised single chain Fv format: importance of interchain disulphide bond location and vL-vH orientation, *Protein engineering, design & selection: PEDS* 25, 321-329).

Figure 8:
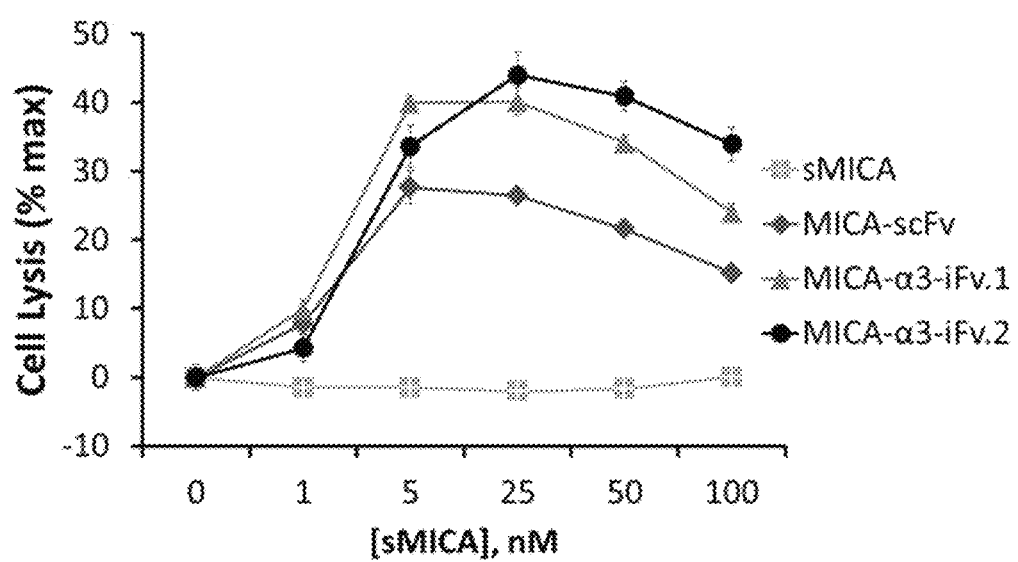
FIG. 8. NK-mediated target cell lysis assays. NKL effector cells were co-incubated with calcein-loaded, FGFR3-expressing P815 target cells at a effector:target ratio of 15:1. Increasing concentrations of a negative control MICA (sMICA) had no effect on target cell lysis, whereas the indicated FGFR3-binding MICA-α3-iFv variants stimulated target cell lysis. Compared to MICA-scFv, both MICA-α3-iFv variants directed greater target cell lysis.

The ability of MICA-α3-iFv to redirect NK cell-mediated lysis of FGFR3-expressing target cells was demonstrated in vitro in a calcein-release assay. The Natural Killer (NK) cell line, NKL, was co-cultured with calcein-loaded P815 target cells ectopically expressing FGFR3. The results in FIG. 8 showed that the two MICA-α3-iFv molecules induced significantly greater NK-mediated lysis compared to the traditional MICA-scFv fusion, while the non-targeted soluble MICA control had no killing activity. These results confirmed that the invented iFv bound FGFR3 on target cells and in the context of the complete parent protein molecule, soluble MICA, induced potent NK cell-mediated lysis.

Figure 9A:
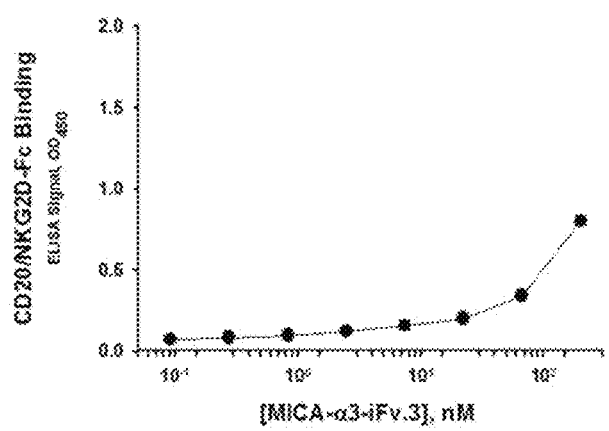
FIGS. 9A and 9B. Target binding and cell lysis activity of a CD20-specific sMICA variant. MICA-α3-iFv.3 exhibited titratable binding to CD20-coated wells in an ELISA (FIG. 9A), and also enhanced NK-mediated cell lysis of CD20-expressing Ramos cells (FIG. 9B). In the experiments shown in FIG. 9B, NKL effector cells were co-incubated with calcein-loaded CD20-expressing Ramos cells at a effector:target ratio of 15:1, and increasing concentrations of either the negative control (sMICA) or MICA-α3-iFv.3.
Figure 9B:
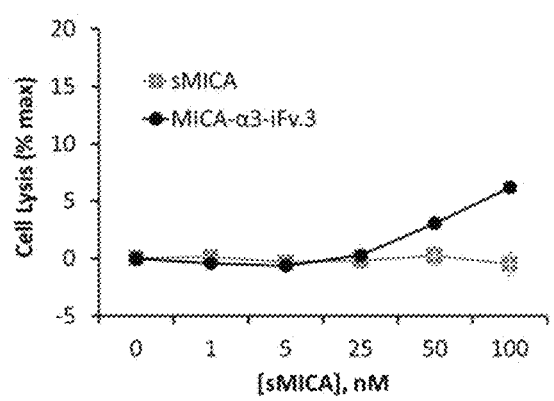

The applicability of the iFv format to other antibody variable domains was demonstrated by similarly constructing an α3-iFv.3 (SEQ ID NO.:8), which contained an iFv derived from a CD20-specific antibody (Du, J., Wang, H., Zhong, C., Peng, B., Zhang, M., Li, B., Huo, S., Guo, Y., and Ding, J. (2007) Structural basis for recognition of CD20 by therapeutic antibody Rituximab, *The Journal of biological chemistry* 282, 15073-15080). FIGS. 9A and 9B show that MICA-α3-iFv.3 was able to specifically bind wells coated with CD20 in a plate-based ELISA as described above and also induced NK-mediated lysis of Ramos cells expressing CD20 in a calcein-release assay.

Example 2

Modified α1-α2 Domains of NKG2D Ligands

Human proteins designated ULBP-1 through ULBP-6 are, like MICA and MICB, naturally occurring, stress-induced, cell surface ligands that bind NKG2D receptors on and activate human NK cells and certain T-cells (15; Cerwenka A, Lanier L L (2004). NKG2D ligands: unconventional MHC class I-like molecules exploited by viruses and cancer. *Tissue Antigens* 61 (5): 335-43. doi:10.1034/j.1399-0039.2003.00070.x. PMID 12753652). In addition, the cowpox virus protein OMCP is a secreted domain that like the α1-α2 domain of MIC proteins binds NKG2D. OMCP exhibits a very high affinity for NKG2D, apparently in order to block NKG2D's recognition of the natural stress ligands induced by the virus on its infected host cell (Eric Lazear, Lance W. Peterson, Chris A. Nelson, David H. Fremont. J Virol. 2013 January; 87(2): 840-850. doi: 10.1128/JVI.01948-12). While the ULBPs and OMCP are considered NKG2D ligands (NKG2DLs) that share the canonical α1-α2 domain structure, the sequence homology with MICA α1-α2 is less than 27%, and they all naturally lack an α3 domain for tethering targeting domains. We constructed a series of non-natural ULB and OMCP proteins by attaching the heterologous polypeptides that specifically targeted and killed FGFR3-expressing cells as the result of fusing to each of ULBP-1, ULBP-2, ULBP-3, ULBP-4, ULBP-6 and OMCP, a modified α3 domain of MICA into which a targeting iFv had been inserted. In addition, we modified the α1-α2 domain of MICA to enhance the affinity of α1-α2 domain for NKG2D and then attached to the modified α1-α2 domains heterologous molecules such as polypeptides. To produce the proteins consisting of ULBP and OMCP α1-α2 domains attached to modified α3-iFv domains we generated a baculoviral expression vector to accommodate the DNA fragments (SEQ ID NOs:9-14) that encoded the different α1-α2 domains of ULBP-1, ULBP-2, ULBP-3, ULBP-4, ULBP-6, and OMCP (SEQ ID NOs:15-20, respectively). The DNA fragments were amplified by PCR, digested using BlpI and NcoI restriction enzymes, and individually subcloned into the baculoviral expression vector, KLM44, replacing the MICA α1-α2 domain. KLM44 was a baculoviral expression vector derived from SW403 into which MICA-α3-iFv.2 had previously been cloned (example 1). The new NKG2DL-α3-iFv.2 constructs, containing the ULBPs and OMCP α1-α2 domain fusions to α3-iFv.2 (ULBP1-α3-iFv.2, ULBP2-α3-iFv.2, ULBP3-α3-iFv.2, ULBP4-α3-iFv.2, ULBP6-α3-iFv.2, and OMCP-α3-iFv.2; SEQ ID NO.:21-26, respectively), were co-transfected with baculoviral DNA into SF9 insect cells. Baculovirus was grown for two amplification cycles and used to express these His-tagged NKG2DL-α3-iFv.2 proteins in T.ni insect cells according to manufacturer's protocol (Invitrogen). The expression was carried out in a 100 mL volume for three days and the growth medium was harvested for purification of the secreted soluble protein using Ni-affinity chromatography. Monomeric proteins of correct molecular weight were purified to >90% purity as determined by SDS-PAGE. Functional characterization was carried out using binding ELISAs and in vitro target cell killing assays.

Figure 10:
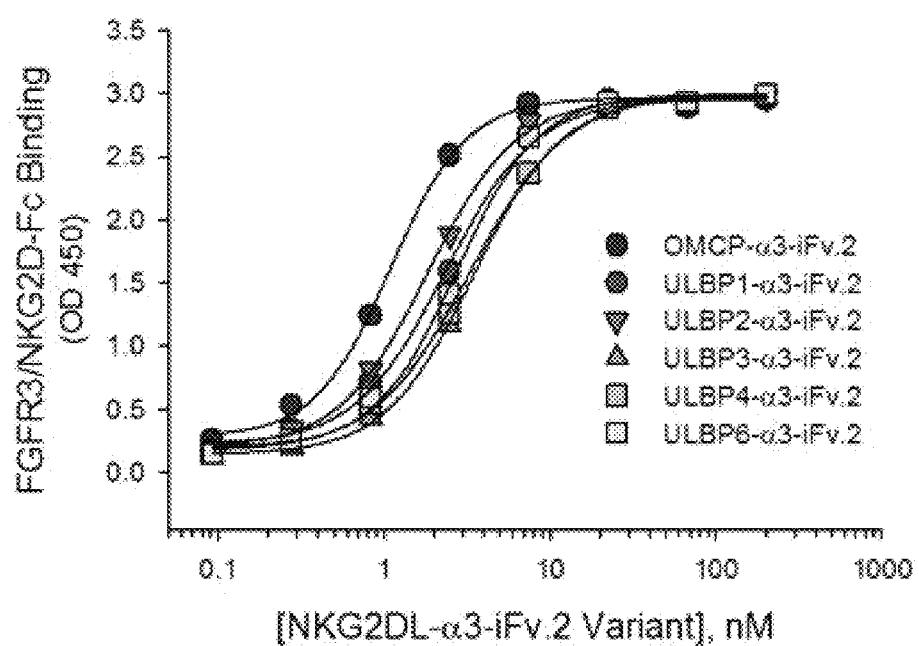
FIG. 10. Titration curves for the NKG2DL-α3-iFv.2 proteins binding to FGFR3-coated wells. Bound protein was detected by ELISA using NKG2D-Fc to confirm the bispecific activity. All versions of the NKG2DL-α3-iFv.2 proteins tested (OMCP, ULBP1, 2, 3, 4, 6) bound FGFR3 similarly.

The 6 purified NKG2DL-α3-iFv.2 proteins were tested in a FGFR3-binding ELISA to confirm simultaneous binding to the FGFR3 target and the NKG2D receptor. FGFR3 in phosphate buffered saline (PBS) was coated onto Maxisorp plates at 2 ug/ml concentration. Each NKG2DL-α3-iFv.2 protein was titrated, allowed to bind FGFR3 for 1 hour, and washed to remove unbound protein. The bound NKG2DL-α3-iFv.2 protein was detected using NKG2D-Fc and anti-Fc-HRP conjugate. FIG. 10 shows that all 6 NKG2DL-α3-iFv.2 proteins bound potently to FGFR3, as expected, through interaction with the iFv.2 domain, and the NKG2D binding activity was retained by the attached NKG2DL α1-α2 domains, which demonstrated that the attached α3-iFv domain imparted functional FGFR3 binding activity to the ULBP and OMPC proteins that, like MIC proteins, bind NKG2D.

Figure 11:
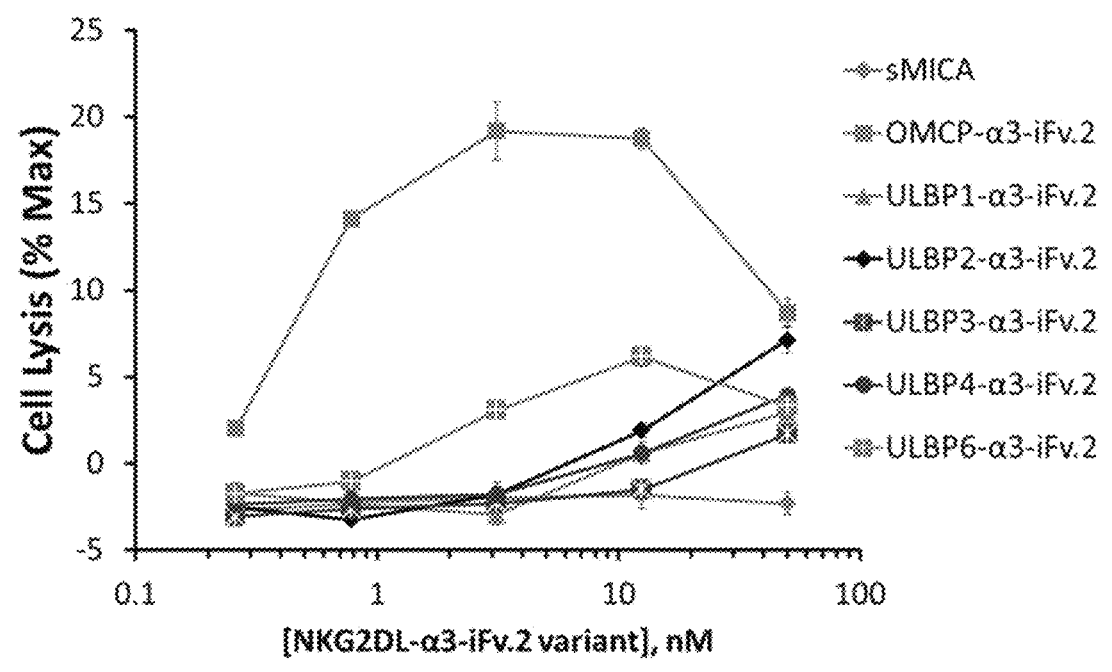

The ability of the NKG2DL-α3-iFv.2 proteins to redirect NK cell-mediated lysis of FGFR3-expressing target cells was demonstrated in vitro in a calcein-release assay. The Natural Killer (NK) cell line, NKL, was co-cultured with calcein-loaded P815 target cells ectopically expressing FGFR3. The results in FIG. 11 showed that OMCP-α3-iFv.2 induced the greatest NK-mediated lysis, while the other NKG2DL-α3-iFv.2 proteins all displayed specific killing activity with varying degrees of potency and amount of lysis. These results confirmed that the invented iFv imparts specific binding activity to other proteins that retained their own functional properties and induced different levels of cell-mediated lysis of iFv-targeted cells.

Example 3

Modified α1-α2 Domains of NKG2D Ligands

These are examples of attaching polypeptides to NKG2DLs which were modified to significantly enhance their binding affinity to the human NKG2D receptor. The α1-α2 domain of MIC proteins is an NKG2DL for the NKG2D receptor. This affinity is sufficient for physiologic activation of NK cells and stimulating lysis of cells expressing native full-length MIC proteins irreversibly tethered to the two-dimensional plasma membrane surface of a "target cell" (Bauer S, Groh V, Wu J, Steinle A, Phillips J H, Lanier L L, Spies T., Science. 1999 Jul. 30; 285(5428):727-9.). However, because engineered soluble MIC proteins of the instant invention reversibly bind specific target antigens on the surface of a target cell, the binding affinity of the engineered soluble MIC protein to NKG2D will directly affect the stability of the soluble MIC-dependent complex formed between NK cells and cells expressing target antigens. Especially if the affinity between sMICA and NKG2D is increased by a substantially slower dissociation rate or off-rate of the modified sMICA from NKG2D, the NK cell-based killing would be expected to be greater at lower densities of soluble MIC molecules bound to a target cell. Prior to the instant invention there had not been identified any α1-α2 mutations that alter the killing activity of soluble MIC proteins or significantly reduce the binding off-rate to enhance affinity of MIC proteins to NKG2D. A computational design effort showed that three mutations in the α1-α2 domain of wild-type MICA: N69W, K152E, and K154D (WED-MICA) in combination can moderately affect NKG2D binding affinity by affecting the stability of unbound MICA and thereby its association rate or on-rate of binding to NKG2D (Lengyel C S, Willis L J, Mann P, Baker D, Kortemme T, Strong R K, McFarland B J. J Biol Chem. 2007 Oct. 19; 282(42):30658-66. Epub 2007 Aug. 8); Subsequent extensive computational design work by the same group scanning by iterative calculations 22 amino acid positions of MICA theoretically in contact with NKG2D, according to the published structural descriptions (Li P, Morris D L, Willcox B E, Steinle A, Spies T, Strong R K., Nat Immunol. 2001 May; 2(5):443-451), showed experimentally that when combined with the earlier designed 3 changes, further rational, iterative computational design of MICA qualitatively changed its affinity for NKG2D from weak (Kd ~2.5 µM) to moderately tight (Kd=51 nM) with a total of seven combined mutations (Henager, Samuel H., Melissa A. Hale, Nicholas J. Maurice, Erin C. Dunnington, Carter J. Swanson, Megan J. Peterson, Joseph J. Ban, David J. Culpepper, Luke D. Davies, Lisa K. Sanders, and Benjamin J. McFarland, 2102, Combining different design strategies for rational affinity maturation f the MICA-NKG2D interface. Protein Science 21:1396-1402). In contrast, the experimental approach described in the instant invention experimentally selected amino acid modifications of MICA that slowed the off-rate between the α1-α2 domain of MICA and NKG2D, commencing with a MICA stabilized by the 3 WED changes of Lengyel et al (Lengyel C S, Willis L J, Mann P, Baker D, Kortemme T, Strong R K, McFarland B J., J Biol Chem. 2007 Oct. 19; 282(42):30658-66. Epub 2007 Aug. 8).

This example of the instant invention relates to modifying the NKG2D binding affinity of soluble MIC proteins through engineering specific mutations at selected amino acid positions within the α1-α2 domain that influence the off-rate binding kinetics and thereby alter the NK cell-mediated killing activity of the invented non-natural, targeted MIC molecules.

To engineer soluble non-natural α1-α2 domains with altered affinity to NKG2D 57 residues in the α1-α2 domain were chosen for extensive mutagenesis (FIG. 12A). Synthetic DNA libraries coding for the α1-α2 domain and containing NNK mutagenic codons at each of the 57 amino acid positions were synthesized, individually cloned as fusions to the pIII minor coat protein of M13 phage, and phage particles displaying the mutagenized α1-α2 variants were produced in SS320 *E. coli* cells according to standard methodologies (Andris-Widhopf, J., Steinberger, P., Fuller, R., Rader, C., and Barbas, C. F., 3rd. (2011) Generation of human Fab antibody libraries: PCR amplification and assembly of light- and heavy-chain coding sequences, *Cold Spring Harbor protocols* 2011). The α1-α2 phage libraries were sorted for increased binding affinity using recombinant biotinylated NKG2D as the target antigen and cycled through iterative rounds of intentionally prolonged binding, prolonged washing, and eluting of the phage clones in order to select high affinity variants enriched for slow dissociation- or off-rates. A set of specific amino acid mutations occurred at high frequencies at 6 positions in α1-α2 and were selected as preferred amino acid substitutions with enhanced NKG2D binding affinity (FIG. 12B, Table 1).

TABLE 1

Selected affinity mutations at the indicated 6 amino acid positions of the α1-α2 domain of MIC. The amino acids of SEQ ID NOs.: 35 at each of the 6 positions are shown in bold in the first row of the table. The identified affinity mutations are listed in decreasing frequency from top to bottom. All amino acids are represented by the single letter IUPAC abbreviations.

| S20 | G68 | K125 | E152 | H161 | Q166 |
|-----|-----|------|------|------|------|
| P   | L   | L    | T    | R    | F    |
| T   | F   | R    | V    | S    | S    |
| D   | S   | F    | G    | A    | H    |
| A   | A   | T    | F    | K    | Y    |
| L   | Y   | A    | Y    | G    | W    |
| N   | I   | N    | A    | L    | V    |
|     | E   | V    | Q    | F    | L    |
|     | T   | Y    | D    | Y    | M    |
|     | W   | I    | I    |      |      |
|     |     | S    | N    |      |      |
|     |     |      | S    |      |      |
|     |     |      | H    |      |      |
|     |     |      | M    |      |      |
|     |     |      | P    |      |      |

We synthesized DNA polynucleotides (SEQ ID NOs. 27-30) encoding the α1-α2 domains of 4 representative variants 15, 16, 17, 18 that contained different combinations of specific discovered mutations (Table 2).

TABLE 2

Sequences of specific α1-α2 domain variants. The specific amino acid substitutions for variants 15, 16, 17, and 18 (SEQ ID NOS.: 31-34, respectively) are listed relative to the amino acids of SEQ ID NO.: 35 in bold. All amino acids are represented by the single letter IUPAC abbreviations.

| Variant | SEQ ID NO.: | S20 | G68 | K125 | H161 |
|---|---|---|---|---|---|
| 15 | 31 | S | G | N | R |
| 16 | 32 | S | G | L | R |
| 17 | 33 | S | L | L | R |
| 18 | 34 | P | L | L | R |

Figure 13A:
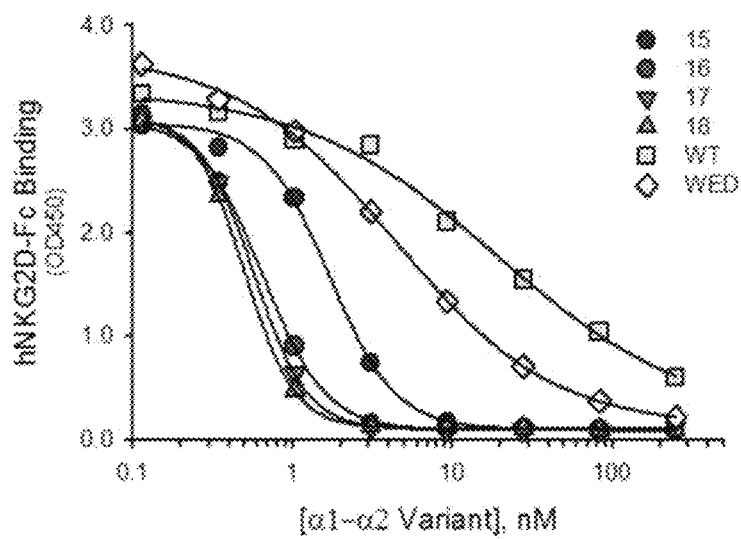
FIGS. 13A and 13B. NKG2D-Fc competition ELISAs to affinity rank α1-α2 variants.

To the NKG2DLs in the above example, we directly attached heterologous molecules such as a polypeptide to each of these 4 modified α1-α2 NKG2DLs using a linker peptide. Four His-tagged proteins (SEQ ID NOs.: 31-34) consisting of modified NKG2DLs with attached heterologous molecules were expressed in insect cells and purified to characterize their NKG2D binding affinities and kinetic binding parameters. Using a competitive binding ELISA, we determined the relative NKG2D binding affinities of the 4 modified α1-α2 variants. A soluble wild type (WT) NKG2DL, sMICA protein, was coated in all wells of a maxisorp ELISA plate to provide a binding partner for the human NKG2D-Fc reagent. Solutions of the four α1-α2 variants as well as WT and WED-α1-α2 domains (SEQ ID NO.: 35) were titrated in the ELISA wells and allowed to competitively inhibit 2 nM human NKG2D-Fc binding to the WT sMICA coated on the plate. The level of human NKG2D-Fc that bound to the WT NKG2DL on the plate was detected using an anti-Fc-HRP antibody. FIG. 13A shows variants 16, 17, and 18 exhibited $IC_{50}$ values of 0.7, 0.6, 0.5 nM while variant 15 exhibited an $IC_{50}$ value of 1.7 nM, all possessing significantly better binding to NKG2D, 27, 32-, 38- and 11-fold better, than WT NKG2DL, respectively, as well as substantially better than WED-MICA (Table 3).

TABLE 3

Figure 13B:
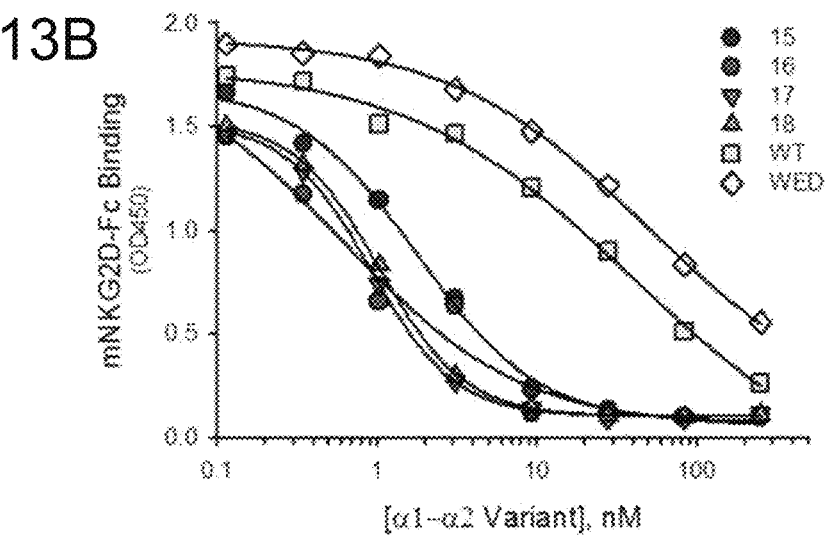

Equilibrium and kinetic binding parameters for α1-α2 variants. $IC_{50}$ values were derived from 4-parameter fits to the competition binding titrations (FIGS. 12A and 12B) and the kinetic binding parameters were derived from single exponential fits to the binding kinetics (FIGS. 13A and 13B). Equilibrium binding constants ($K_d$) were derived from the kinetic binding parameters using the equation $K_d = k_{OFF}/k_{ON}$.

| α1-α2 Variant | $IC_{50}$ (nM) | Kinetic Binding Parameters | | $K_d$ (nM) |
|---|---|---|---|---|
| | | $k_{ON}$ (M$^{-1}$s$^{-1}$) | $k_{OFF}$ (s$_{-1}$) | |
| WT | 19.4 | $1.3 \times 10^5$ | $1.8 \times 10^{-3}$ | 13.8 |
| WED | 4.4 | $2.9 \times 10^5$ | $1.7 \times 10^{-3}$ | 5.9 |
| 15 | 1.7 | $0.7 \times 10^5$ | $1.1 \times 10^{-4}$ | 1.5 |
| 16 | 0.7 | $2.0 \times 10^5$ | $0.9 \times 10^{-4}$ | 0.5 |
| 17 | 0.6 | $2.0 \times 10^5$ | $0.7 \times 10^{-4}$ | 0.4 |
| 18 | 0.5 | $2.3 \times 10^5$ | $0.9 \times 10^{-4}$ | 0.4 |

Importantly, the relative $IC_{50}$ differences also translated to better binding to murine NKG2D-Fc (FIG. 13B), and demonstrated the ability to improve binding of soluble, modified α1-α2 domains across human and non-human NKG2D receptors, an important property for preclinical drug development.

Figure 14:
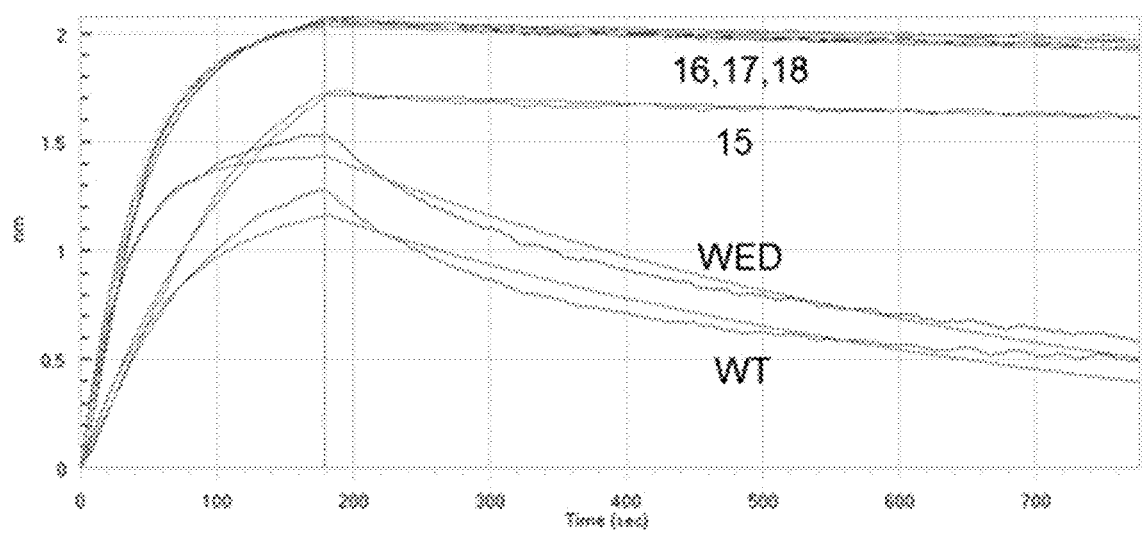
FIG. 14. Analysis of the association and dissociation kinetics for α1-α2 variants binding to NKG2D, as measured by biolayer interferometry on an Octet instrument. Kinetic traces for a panel of α1-α2 variants. The association and dissociation phases were fit using a single exponential 1:1 binding equation and on- and off-rate constants derived from the fits are shown in Table 3.

In order to understand the kinetic basis for the altered affinities, both the on-rates and off-rates for the α1-α2 variant NKG2DLs binding to surface coated biotinylated human NKG2D were measured using biolayer interferometry (Octet) at 100 nM of each of the modified α1-α2 proteins. Consistent with results from the $IC_{50}$ ELISAs, variants 16, 17 and 18 each displayed significant reductions in the off-rate (18-fold relative to WT), which is largely responsible for the affinity increase (~30-fold relative to WT α1-α2) (FIG. 14; Table 3). Although variant 15 displayed a similar slow off-rate as did 16, 17, and 18, its on-rate was decreased, resulting in an affinity stronger than WT but weaker variants 16, 17 and 18. Because the only difference between variant 15 (SEQ ID NO.:31) and 16 (SEQ ID NO.:32) was K125N versus K125L, the mutation at position 125 clearly altered the on-rate while the decreased off-rate was attributed to the H161R mutation. Therefore, while the selected set of NKG2DL mutations (Table 1) was used to increase the α1-α2 affinity for NKG2D through significant off-rate reduction, certain substitutions also altered the on-rate resulting in a range of incremental affinity increases that we showed in this invention to have differential activity in the NK cell-mediated killing assays as described below.

Figure 15:
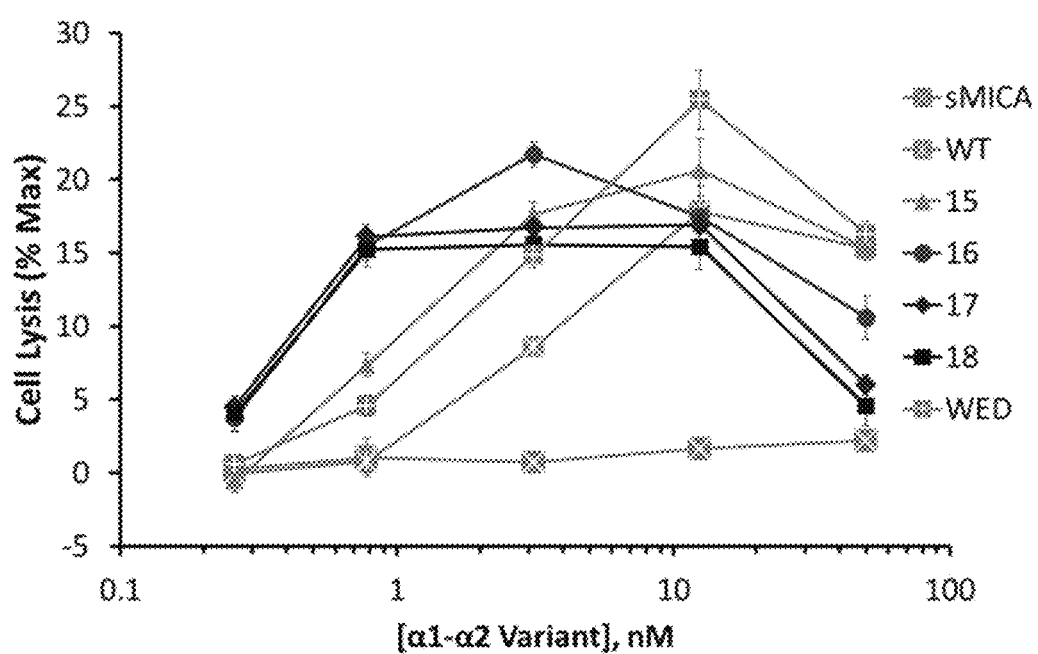
FIG. 15. NK-mediated target cell killing assay for the α1-α2 variants targeting FGFR3-expressing target cells. NKL effector cells were co-incubated with calcein-loaded, FGFR3-expressing P815 target cells at a effector:target ratio of 15:1. Increasing concentrations of a negative control MICA (sMICA) had no effect on target cell lysis, whereas the indicated α1-α2 variants stimulated target cell lysis. Relative to WT and WED-MICA, variants 16, 17, and 18 exhibited significantly increased killing at low concentrations.

The ability of the α1-α2 affinity variants to redirect NK cell-mediated lysis of FGFR3-expressing target cells was demonstrated in vitro in a calcein-release assay. The human Natural Killer (NK) cell line, NKL, was co-cultured with calcein-loaded P815 target cells ectopically expressing FGFR3 and titrated with soluble modified MIC proteins. The results in FIG. 15 showed that the killing activities of the FGFR3-specific soluble MIC variants correlated with their engineered α1-α2 affinities. Specifically, variants 16, 17, and 18 exhibited ~15-fold more killing than WT at 0.78 nM. The WED-MICA (SEQ ID NO.:35) was only slightly better than WT. Therefore, the invention describes amino acid substitutions within the α1-α2 domain that increased the NKG2D binding affinity by reducing the off-rate of soluble MIC protein binding to human NKG2D and consequentially led to the predictably increased killing potency. WED-MICA, which exhibited somewhat greater affinity than WT MICA to NKG2D (FIG. 13A) by increasing on-rate rather than reducing off-rate (FIG. 14), did not exhibit substantial improvement of target cell killing (FIG. 15). Furthermore, as shown in FIG. 13B, WED-MICA exhibited substantially poorer binding to murine NKG2D than even WT MICA, while variants 15, 16, 17, and 18 each exhibited greater affinity for both human and murine NKG2D, FIGS. 13A and 13B.

These α1-α2 NKG2DL affinity variants 15, 16, 17, and 18 enhanced the binding affinity of the attached polypeptide to the NKG2D receptor and thereby enhanced NK cell-mediated lysis of targeted cells, FIG. 15.

Example 4

Modified α1-α2 Domains of NKG2D Ligands

This embodiment of the instant invention relates to additional α1-α2 NKG2DL affinity variants derived through engineering specific mutations at selected amino acid positions within the α1-α2 domain of soluble MIC molecules, as described in Example 3 (Table 1), that also influence the off-rate binding kinetics and thereby alter the NK cell-mediated killing activity of the non-natural α1-α2 domains. While variants 15-18 focused on specific mutations found at positions S20, G68, K125, and H161, another set of variants were isolated with additional mutations at E152, H158, and Q166 (Table 4).

TABLE 4

Sequences of specific α1-α2 domain variants. The specific amino acid substitutions for variants 20, 25, and 48 are listed relative to the amino acids of SEQ ID NO.: 35, shown in bold in the first row of the table. All amino acids are represented by the single letter IUPAC abbreviations.

| Variant | SEQ ID NO.: | S20 | G68 | K125 | E152 | H158 | H161 | Q166 |
|---|---|---|---|---|---|---|---|---|
| 20 | 39 | S | A | L | Q | R | H | F |
| 25 | 40 | S | G | L | E | H | R | S |
| 48 | 41 | S | G | L | A | I | R | A |

DNA polynucleotides (SEQ ID NOs. 36-38) encoding the α1-α2 domains of 3 representative variants 20, 25, 48 (SEQ ID NOs. 39-41, respectively) that contained different combinations of specific discovered mutations (Table 4), were synthesized. To the NKG2DLs in the above example, heterologous molecules, such as an FGFR3-binding polypeptide, were directly attached to each of these 3 modified α1-α2 NKG2DLs using a linker peptide. The constructs were cloned into the XbaI and BamHI sites of pD2509, a CMV-based mammalian cell expression vector. Three His-tagged proteins (SEQ ID NOs.: 39-41), consisting of modified NKG2DLs with attached heterologous molecules that bind to FGFR3, were transiently expressed in HEK293 cells using the Expi293 expression system according to the manufacturer's protocol (Life Technologies), and purified using Ni-affinity chromatography to obtain the isolated proteins for biochemical and activity-based analysis.

In order to characterize the NKG2D binding affinities, both the on-rates and off-rates for the three α1-α2 variant NKG2DLs binding to surface-coated biotinylated human NKG2D were measured using biolayer interferometry (Octet). Binding titrations were performed for each protein using a titration range of 1-100 nM, and the kinetic data were fitted to obtain on-rates, off-rates, and equilibrium binding constants.

Figure 16:
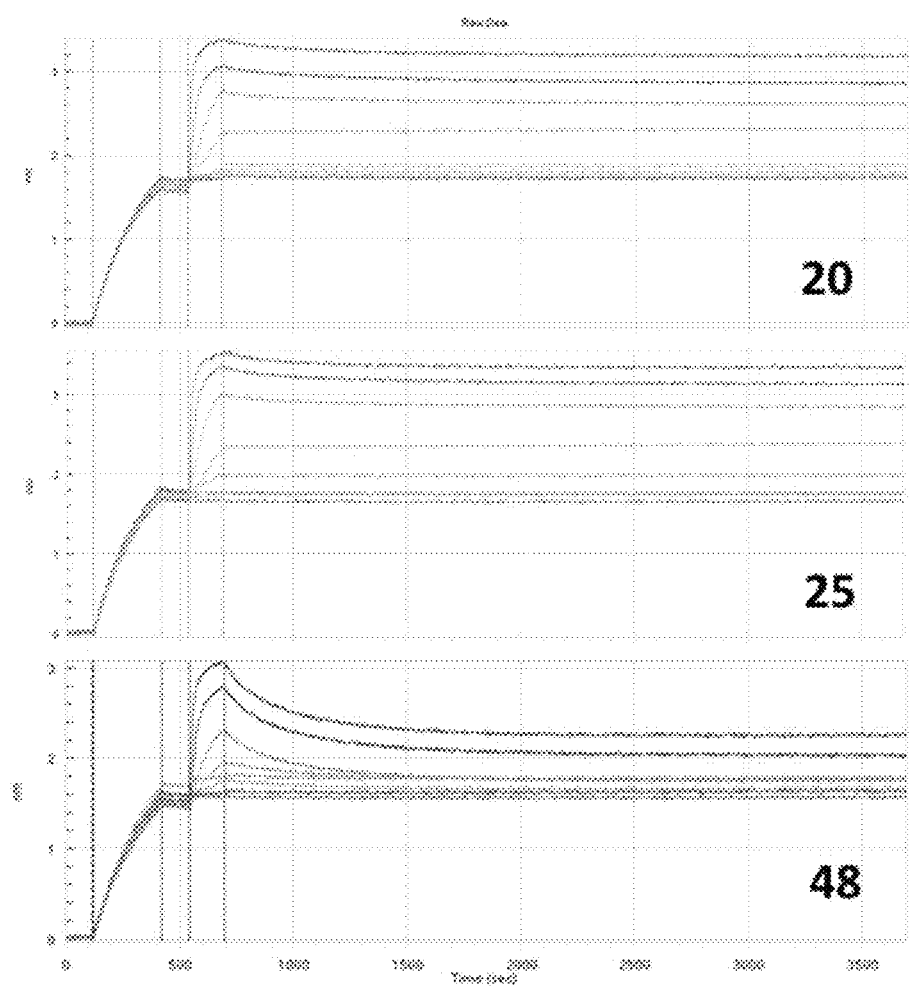
FIG. 16. Analysis of the association and dissociation kinetics for α1-α2 variants 20, 25, and 48 binding to NKG2D, as measured by biolayer interferometry on an Octet instrument. The association and dissociation phases were fit using a single exponential 1:1 binding equation, and on- and off-rate constants derived from the fits are shown in Table 5, FIG. 17. NK-mediated target cell killing, calcein-based assay for α1-α2 variants 16, 25 and WED targeting FGFR3-expressing P815 target cells.

Variant 25 (SEQ ID NO.: 40) contains only the addition of the Q166S mutation relative to variant 16 (SEQ ID NO.: 32) (Table 2), and exhibited a NKG2D binding affinity of 62 pM largely due to decreased off-rate (FIG. 16 and Table 5). This represented an 8-fold enhancement in equilibrium binding affinity due to the Q166S mutation (compare Table 3 and Table 5), and demonstrated that specific mutations at Q166 influenced binding affinity through decreased off-rate.

TABLE 5

Kinetic binding parameters for α1-α2 variants. Kinetic binding parameters were derived from single exponential fits to the binding kinetics (FIG. 16). Equilibrium binding constants ($K_d$) were derived from the kinetic binding parameters using the equation $K_d = k_{OFF}/k_{ON}$.

| | Kinetic Binding Parameters | | |
|---|---|---|---|
| α1-α2 Variant | $k_{ON}$ (M$^{-1}$s$^{-1}$) | $k_{OFF}$ (s$_{-1}$) | $K_d$ (nM) |
| 20 | 3.6 × 10$^5$ | 3.0 × 10$^{-5}$ | 0.083 |
| 25 | 4.7 × 10$^5$ | 2.9 × 10$^{-5}$ | 0.062 |
| 48 | 2.0 × 10$^5$ | 3.0 × 10$^{-3}$ | 15 |

Variant 20 (SEQ ID NO.: 39) contained the specific mutations G68A, E152Q, H158R and Q166F, and maintained binding parameters similar to variant 25 (Table 5), suggesting that this unique combination of specific mutations also has improved NKG2D binding affinity due to a decreased off-rate.

Variant 48 (SEQ ID NO.: 41) contained the K125L and H161R mutations found in variant 16 (Table 2); however the addition of mutations E152A, H158I, and Q166A (Table 4) significantly increased the off-rate, resulting in a 250-fold reduction in NKG2D binding affinity (FIG. 16 and Table 5). The Q166A mutation is not one of the favored affinity enhancement mutations selected for position Q166 (Table 1) and may have contributed to the reduction in off-rate observed. These data clearly demonstrated that unique combinations of engineered, mutations selected and identified at defined positions within α1-α2 domains tuned the NKG2D binding affinity through off-rate modulation.

Figure 17:
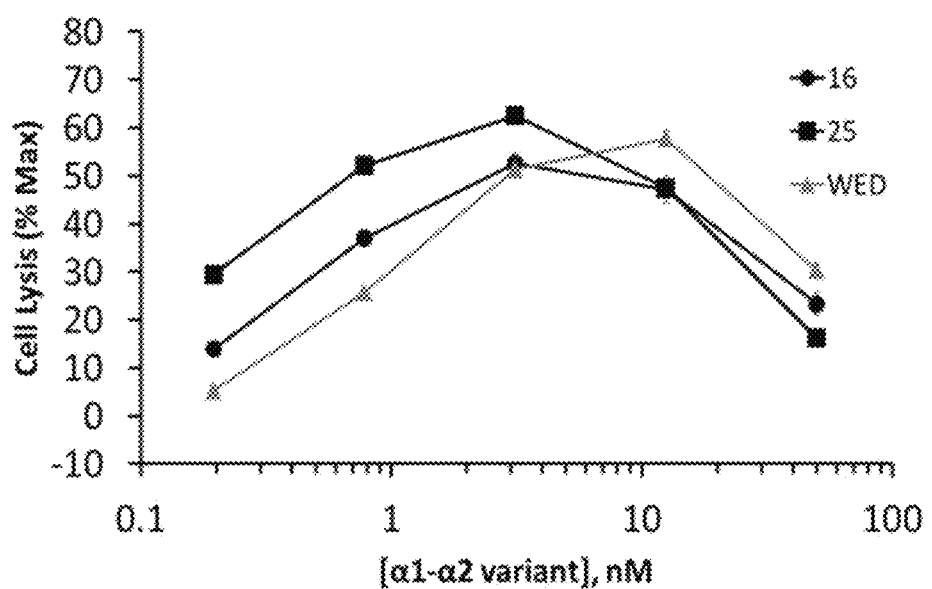

The non-natural α1-α2 affinity variants with attached polypeptides redirected NK cell-mediated lysis of FGFR3-expressing target cells, as demonstrated in vitro in a calcein-release assay. The human Natural Killer (NK) cell line, NKL, was co-cultured with calcein-loaded P815 target cells ectopically expressing FGFR3, and titrated with soluble modified NKG2D ligand α1-α2 proteins. The results in FIG. 17 showed that the killing potencies of the FGFR3-targeted soluble MIC variants correlated with their engineered α1-α2 affinities. Specifically, variant 25 exhibited ~3-fold greater killing than variant 16 at 0.2 nM, representing an ~5-fold improvement in the EC$_{50}$ for cell killing. In addition, the data clearly showed preferred killing activity across representative soluble MIC variants in the order of variant 25>16>WED (FIG. 17).

Example 5

Modified α1-α2 Domains of NKG2D Ligands

This embodiment relates to additional α1-α2 NKG2DL affinity variants derived through engineering the α1-α2 domains of ULBP proteins. ULBP proteins contain α1-α2 domains, which are NKG2D ligands capable of binding to the NKG2D receptor (Cerwenka A, Lanier L L (2004). NKG2D ligands: unconventional MHC class I-like molecules exploited by viruses and cancer. Tissue Antigens 61 (5): 335-43. doi:10.1034/j.1399-0039.2003.00070.x. PMID 12753652). This affinity of NKG2D binding is sufficient for physiologic activation of NK cells and stimulating lysis of cells expressing native full-length ULBP proteins naturally and irreversibly tethered to the two-dimensional plasma membrane surface of a "target cell" (Cerwenka A, Lanier L L (2004). NKG2D ligands: unconventional MHC class I-like molecules exploited by viruses and cancer. Tissue Antigens 61 (5): 335-43. doi:10.1034/j.1399-0039.2003.00070.x. PMID 12753652). However, because engineered soluble α1-α2 domains fused to heterologous polypeptides in certain embodiments of the instant invention reversibly bind specific target antigens on the surface of a target cell, the binding affinity of the engineered ULBP α1-α2 domains to NKG2D will directly affect the stability of the artificial synapse formed between NK cells and cells expressing target antigens, as already shown by engineered soluble MIC proteins (Examples 2-4). In order to diversify the repertoire of engineered non-natural α1-α2 domains as NKG2D ligands, ULBP proteins were used as a substrate or starting point for phage display-based engineering of their NKG2D binding affinity. Despite the structural homology observed between ULBPs and MICA (Radaev, S., Rostro, B., Brooks, A G., Colonna, M., Sun, P D. (2001) Conformational plasticity revealed by the cocrystal structure of NKG2D and its class I MHC-like Ligand ULBP3. *Immunity* 15, 1039-49.), the sequence homology is <50% for the ULBP α1-α2 domains relative to MICA (FIG. 18). Thus, we sought the identities of codon positions in ULBP α1-α2 domains that improve NKG2D binding affinity.

Figure 19A:
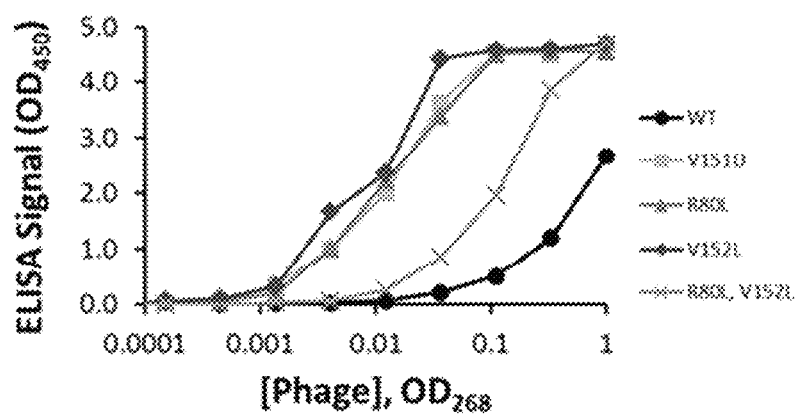
FIGS. 19A and 19B. Phage ELISA titrations of ULBP variants binding to NKG2D.

To engineer soluble, non-natural α1-α2 domains from ULBP proteins, ULBP2 and ULBP3 were chosen for phage display and selection of mutants with high affinity NKG2D binding. Sixty amino acid positions in the α1-α2 domain of ULBP2 (SEQ ID NO.:16), and thirty-six amino acid positions in the α1-α2 domain of ULBP3 (SEQ ID NO.:17), were chosen for extensive mutagenesis (FIG. 18). In addition, conservative cysteine-to-serine mutations were made at C8S in ULBP2 (SEQ ID NO.:16) and C103S in ULBP3 (SEQ ID NO.: 17) in order to remove unpaired free cysteines that could interfere with phage panning. Synthetic DNA libraries coding for these α1-α2 domains, and containing NNK mutagenic codons at each of the selected amino acid positions, were synthesized, individually; cloned as fusions to the pIII minor coat protein of M13 phage; and phage particles displaying the mutagenized α1-α2 ULBP2 or ULBP3 variants were produced in SS320 *E. coli* cells according to standard methodologies (Andris-Widhopf, J., Steinberger, P., Fuller, R., Rader, C., and Barbas, C. F., 3rd. (2011). Generation of human Fab antibody libraries: PCR amplification and assembly of light- and heavy-chain coding sequences, *Cold Spring Harbor protocols* 2011). The α1-α2 phage display libraries were sorted for increased binding affinity to NKG2D using human NKG2D-Fc as the target protein, and cycled through iterative rounds of intentionally prolonged binding, prolonged washing, and eluting of the phage clones in order to select high affinity variants enriched for slow dissociation- or off-rates. For ULBP2, specific amino acid mutations were found at high frequencies at positions R80, V151, V152, and A153 in α1-α2, and were identified as preferred amino acid substitutions with enhanced NKG2D-binding affinity (FIG. 19A and Table 6).

TABLE 6

Selected affinity mutations at the indicated 4 amino acid positions of the α1-α2 domain of ULBP2. The amino acids of SEQ ID NOs.: 16 at each of the 4 positions are shown in bold in the first row of the table. The identified affinity mutations are listed in decreasing frequency from top to bottom. All amino acids are represented by the single letter IUPAC abbreviations.

| R80 | V151 | V152 | A153 |
|---|---|---|---|
| L | D | L | E |
| W | E | W | K |
| V | Q | | G |
| F | K | | P |
| I | N | | |
| S | R | | |
| A | T | | |
| E | | | |
| P | | | |
| T | | | |

Figure 19B:
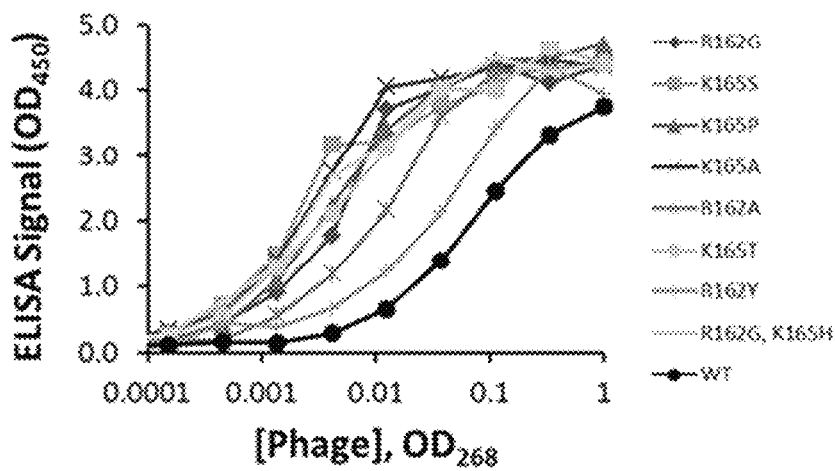

For ULBP3, specific amino acid mutations were found at high frequencies in different locations relative to ULBP2 (FIG. 18). Positions R162 and K165 in the α1-α2 domain of ULBP3 contained specific mutations that were identified as preferred amino acid substitutions with enhanced NKG2D-binding affinity (FIG. 19B and Table 7). These modified non-natural α1-α2 domains derived from ULBP2 and ULBP3 can be used for enhanced NKG2D binding in multiple therapeutic formats as single proteins or fusions to heterologous peptides or polypeptides.

TABLE 7

Selected affinity mutations at the indicated 2 amino acid positions of the α1-α2 domain of ULBP3. The amino acids of SEQ ID NOs.: 17 at each of the 2 positions are shown in bold in the first row of the table. The identified affinity mutations are listed in decreasing frequency from top to bottom. All amino acids are represented by the single letter IUPAC abbreviations.

| R162 | K165 |
|---|---|
| G | S |
| A | P |
| Y | A |
| | T |
| | H |
| | N |
| | Q |
| | G |

Example 6

Modified α1-α2 Domains Fused to Antibody Peptides

Figure 20A:
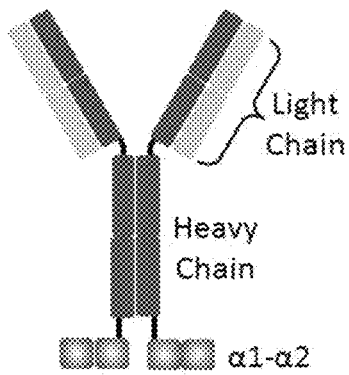
FIGS. 20A-D. Fusions of native (WT), modified variant WED, 25 or 48 α1-α2 domains to heavy chain (FIG. 20A) or light chain (FIG. 20B) of an FGFR3-specific antibody affected NK-dependent target cell killing. Fusions of variants 25 and 48 to either heavy chain (FIG. 20C) or light chain (FIG. 20D) significantly enhanced the extent of killing and the potency of killing compared to the WED variant and to the native (WT) fusions.
Figure 20B:
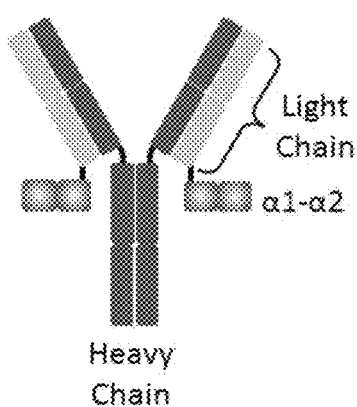

These are examples of attaching antibody polypeptides to NKG2DLs which were modified to significantly enhance their binding affinity to the human NKG2D receptor. The α1-α2 domain of MIC proteins is an NKG2DL for the NKG2D receptor. Antibodies are highly stable glycoproteins made up of two large heavy chains and two small light chains (FIG. 1). The large amount of diversity that can be generated within the CDR regions of the variable domains allows for specific antibodies to be generated to specific antigen targets (Hozumi N, Tonegawa S (1976). "Evidence for somatic rearrangement of immunoglobulin genes coding for variable and constant regions". *Proc. Natl. Acad. Sci. U.S.A.* 73 (10): 3628-3632. doi:10.1073/pnas.73.10.3628. PMC 431171. PMID 824647.) Antibodies have become a significant therapeutic platform for drug development and can mediate both target binding and neutralization, as well as modulate the immune system through complement and Fc receptor binding (Vidarsson, G., Dekkers, G., Rispens, T. (2014) IgG subclasses and allotypes: from structure to effector functions. *Frontiers in Immunology* 5, 520.). Prior to the present invention, there did not exist an IgG antibody format that can directly activate immune cells using non-natural α1-α2 domains that bind more tightly than native NKG2DLs to the NKG2D receptor. Previous work has demonstrated that the mouse NKG2D ligand, Rae1 beta, can be fused to an anti-Her2 antibody for use as an anti-tumor agent in mice (Cho, H M., Rosenblatt, J D., Tolba, K., Shin, S J., Shin, D., Calfa, C., Zhang, Y., Shin, S U. (2010) Delivery of NKG2D ligand using and anti-Her2 antibody-NKG2D ligand fusion protein results in an enhanced innate and adaptive antitumor response. *Cancer Research* 70, 10121-30.). However, mouse NKG2D ligands do not bind human NKG2D, and there are no natural human NKG2D ligands with high affinity to human and mouse NKG2D. Fusions between the engineered α1-α2 NKG2D ligands of the instant invention and the heavy chain or light chain of IgG antibodies (FIGS. 20A and 20B) overcame these limitations and highlighted the versatility of fusions of modified α1-α2 domains to heterologous proteins or peptides.

Figure 20C:
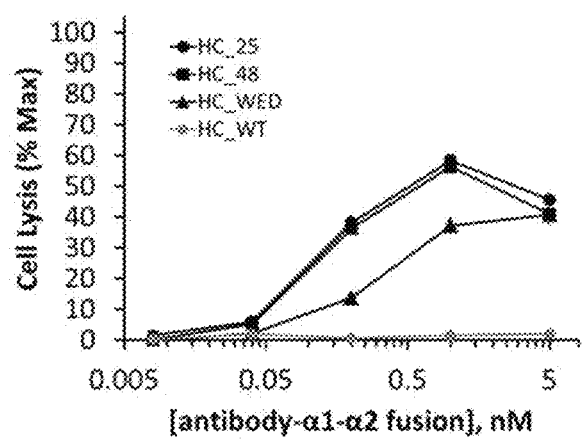
Figure 20D:
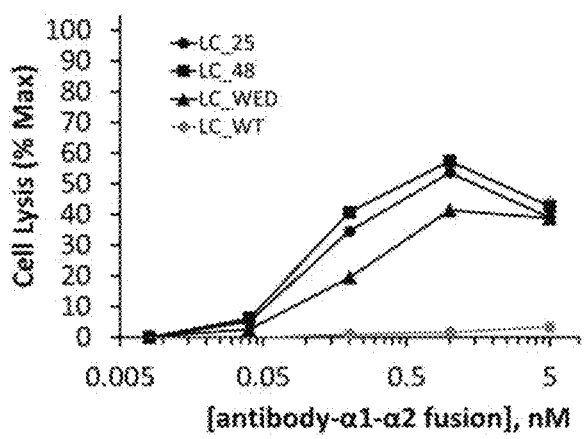

To generate variant α1-α2 domain fusions to antibodies, the DNA sequences encoding α1-α2 domain for MIC WT, variants WED, 25, and 48, were synthesized and cloned as C-terminal fusions to either the heavy chain (HC_WT, HC_WED, HC_25, HC_48) or light chain (LC_WT, LC_WED, LC_25, LC_48) sequence from the FGFR3-specific antibody (Qing, J., Du, X., Chen, Y., Chan, P., Li, H., Wu, P., Marsters, S., Stawicki, S., Tien, J., Totpal, K., Ross, S., Stinson, S., Dornan, D., French, D., Wang, Q. R., Stephan, J. P., Wu, Y., Wiesmann, C., and Ashkenazi, A. (2009) Antibody-based targeting of FGFR3 in bladder carcinoma and t(4; 14)-positive multiple myeloma in mice, *The Journal of clinical investigation* 119, 1216-1229.) (SEQ ID NOs.: 42-49, respectively). The resulting fusions were cloned into the mammalian expression vector pD2509 and expressed as paired full IgG antibodies with either heavy or light chain fusions of the modified α1-α2 domains (SEQ ID NOs.: 50-57, respectively). Transient expressions were carried out in HEK293 cells using the Expi293 expression system according to the manufacturer's protocol (Life Technologies), and purified using standard protein A affinity chromatography. The ability of the non-natural α1-α2-antibody fusions to redirect NK cell-mediated lysis of FGFR3-expressing target cells was demonstrated in vitro in a calcein-release assay. The human Natural Killer (NK) cell line, NKL, was co-cultured with calcein-loaded P815 target cells ectopically expressing FGFR3 and titrated with the engineered antibody fusion proteins. The results in FIGS. 20C and 20D showed that the killing activities of the FGFR3-specific non-natural α1-α2-antibody fusions correlated with their engineered NKG2D affinities. Specifically, antibodies that contained either heavy chain or light chain fusions of non-natural variants 25 and 48 (HC_25, HC_48 and LC_25, LC_48) killed FGFR3-expressing cells more effectively than antibody fusions containing either WT or WED α1-α2 domains.

Figure 21A:
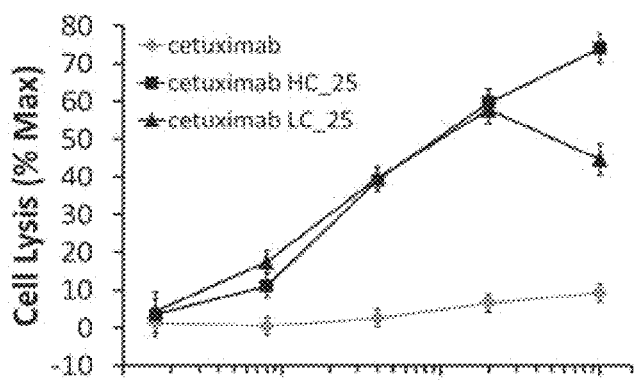
FIGS. 21A-C. Fusions of variant 25 α1-α2 domain to the heavy chains or light chains of antibodies targeting human EGFR (FIG. 21A), HER2 (FIG. 21B), or PDL1 (FIG. 21C) each enhanced NKL cell-mediated target cell killing. The poor or absent killing by the respective parent antibodies, cetuximab (FIG. 21A), trastuzumab (FIG. 21B), and anti-PDL1 (FIG. 21C) are shown.
Figure 21B:
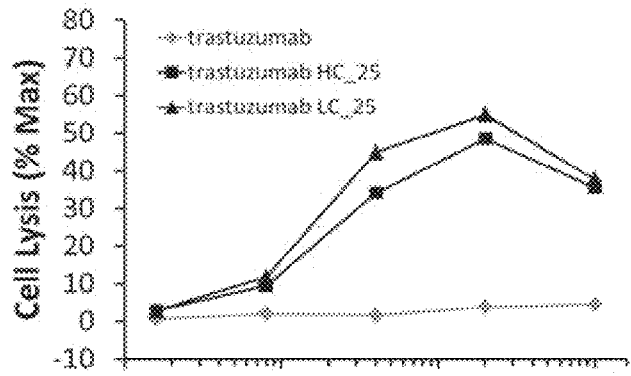
Figure 21C:
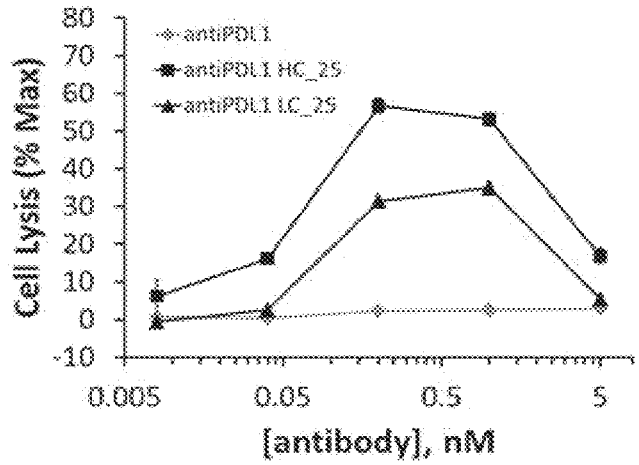

This was further demonstrated to be a general and useful approach to fusing modified α1-α2 domains to antibodies, by fusing the variant 25 α1-α2 domain to the C-terminal of either the heavy chain or light chain of EGFR-specific antibody cetuximab (U.S. Pat. No. 6,217,866), Her2-specific antibody trastuzumab (Carter, P., Presta, L., Gorman, C M., Ridgway, J B., Henner, D., Wong, W L., Rowland, A M., Kotts, C., Carver, M E., Shepard, H M. (1992) *Proc Natl Acad Sci* 15, 4285-9), or an anti-PDL1 antibody (US Patent 20140341917) (SEQ ID NOs.:58-63, respectively). The resulting fusions were expressed as paired light and heavy chain full IgG antibodies with either heavy or light chain fusions of the variant 25 α1-α2 domain. Transient expressions were carried out in HEK293 cells using the Expi293 expression system according to the manufacturer's protocol (Life Technologies), and purified using standard protein A affinity chromatography. The ability of the variant 25 antibody fusions to redirect NK cell-mediated lysis of target-expressing cells was demonstrated in vitro in a calcein-release assay. The human Natural Killer (NK) cell line, NKL, was co-cultured with calcein-loaded A431 EGFR-expressing target cells, SKBR3 Her2-expressing target cells, or PDL1-expressing B 16 cells and titrated with the respective target-specific engineered antibody fusion proteins. The results in FIGS. 21A, 21B, and 21C showed that the killing activities of the target-specific variant 25-antibody fusions were in all cases drastically improved over the non-fused parent antibody and very potent with sub-nanomolar $EC_{50}$ values. These data show that modified α1-α2 variant-antibody fusions are a universal platform for allowing IgG antibodies to bind tightly to NKG2D and to direct antigen-specific cell lysis.

Example 7

Trastuzumab Fusions to α1-α2 Variant 25 Bind NK Cells In Vivo and Elicit Potent Antigen Presentation Fusion proteins containing α1-α2 domain variants that bind NKG2D with high affinity bound NK cells in vivo. Thus, antigen-specific antibodies containing modified α1-α2 fusions bind NKG2D tightly and thereby effectively armed the surface of NK cells in vivo with antibodies to seek out target cells expressing a particular antigen. This activity was similar to engineered CAR cells (Gill, S., and June, C H. (2015) Going viral: chimeric antigen receptor T-cell therapy for hematological malignancies. *Immunol Rev* 263, 68-89.), but did not require genetic modification of the NKG2D-expressing cell type.

To demonstrate that antibodies containing modified α1-α2 fusions bind NK cells in vivo, trastuzumab and the corresponding heavy and light chain fusions of variant 25 were analyzed in vivo for serum pharmacokinetic (PK) profiles and the pharmacodynamics (PD) of NK cell labeling. All three antibodies: parent trastuzumab; trastuzumab HC_25 fusion; and trastuzumab LC_25 fusion, were conjugated with Alexa Flour 647 according to the manufacturer's protocol (Life Technologies). Groups of three C57BL/6 mice were injected with a single dose of 100 µg of each antibody, and blood was drawn at indicated time points for plasma PK ELISAs and flow cytometry of peripheral NK cells. The PK profile of the parent trastuzumab antibody displayed typical alpha-phase distribution within 24-hrs and beta-phase elimination consistent with greater than a 1 week half-life of antibodies in mice (FIG. 22A). For both the heavy chain and light chain fusions with variant 25, the initial alpha-phase showed a much greater volume of distribution relative to the parent antibody, consistent with an NKG2D-sink, while the beta-phase elimination was also consistent with typical antibody clearance in mice (FIG. 22A). Using flow cytometry of peripheral NK cells from the mouse blood, the level of NK cell staining with Alexa Fluor 647 showed a clear time-dependent increase in the percent of NK cells labeled with the antibody fusion, but not the parent antibody (FIG. 22B). The increase in labeling by the fusions peaked within 24 hrs, consistent with the sink observed in the PK profiles for the fusions, and was stable at least for three days post injection. The combined PK and PD data demonstrate that the trastuzumab antibodies containing variant 25 α1-α2 fusions formed stable complexes with NKG2D on NK cells in vivo.

Figure 23A:
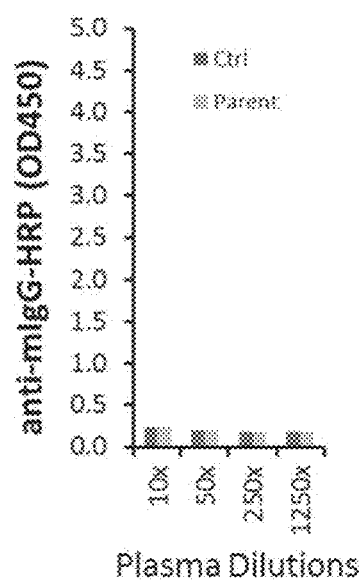
FIGS. 23A-C. Anti-drug antibodies raised in the same animals described in Example 7 and FIG. 21 administered Trastuzumab parent (FIG. 23A), Trastuzumab-based HC (FIG. 23B) and Trastuzumab-LC (FIG. 23C) fusions to variant 25. The control (Ctrl) plasma was from a mouse not administered any antibody-containing agent.
Figure 23B:
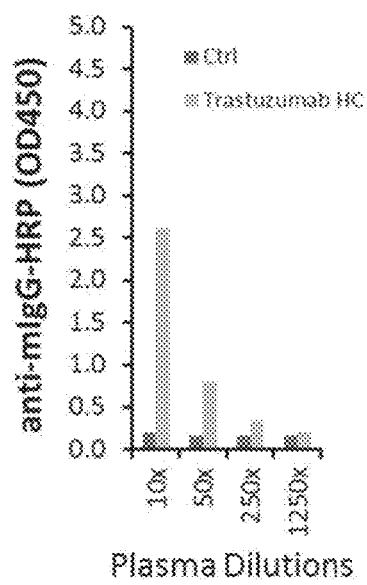
Figure 23C:
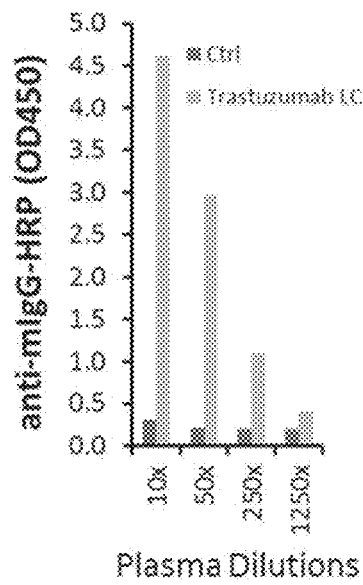
Figure 24A:
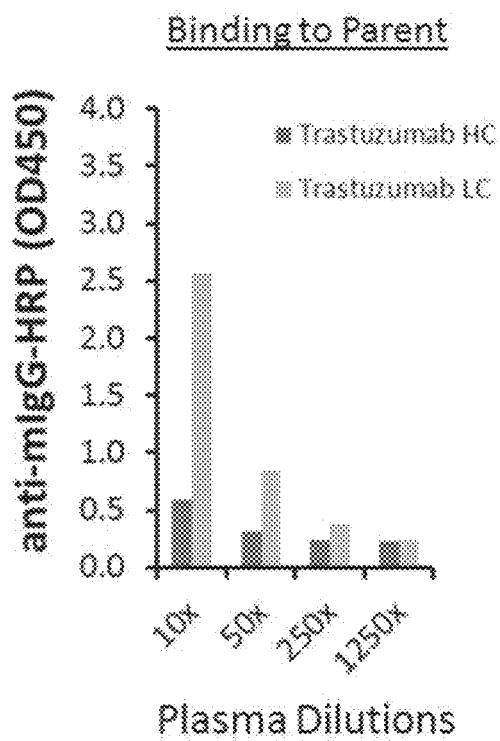
FIGS. 24A and 24B. Antibodies generated in animals administered variant 25 α1-α2 domain fusions to trastuzumab-HC and -LC, as described in Example 7 and FIGS. 21-22, bound to both the parent antibody (FIG. 24A) and to the α1-α2 domain (FIG. 24B).
Figure 24B:
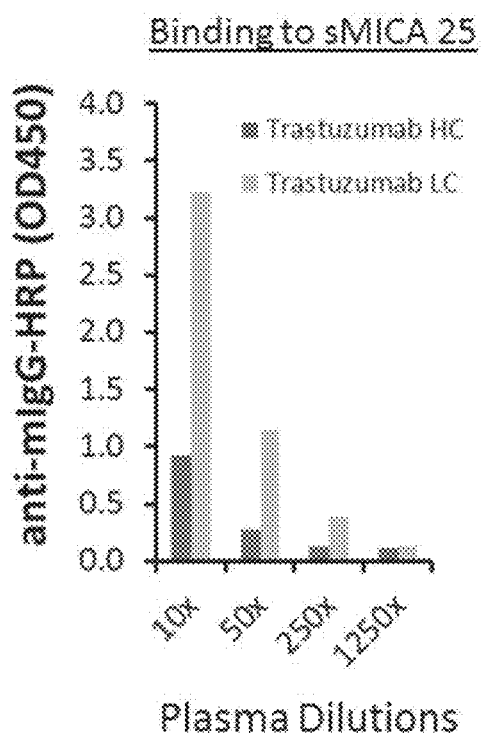

To assess the appearance of anti-drug antibodies (ADAs) to the human IgG trastuzumab antibody, the plasma samples from the PK/PD study were assessed for ADAs using an ELISA. In FIGS. 23A-C, ELISAs for mouse IgG binding to wells coated with the 3 respective dosed antibodies revealed that only the antibodies fused with variant 25 elicited ADAs within seven days after a single dose of antibody. The parent trastuzumab antibody gave no ADA signal. In order to determine whether the antibody fusions elicited an immune (ADA) response to both the α1-α2 domain and the antibody (trastuzumab) component when the trastuzumab antibody itself did not elicit an immune response, the ADA-positive plasma from the antibody fusions were tested against the parent antibody and the variant 25 α1-α2 domain individually; both moieties reacted with ADAs from plasma (FIGS. 24A and 24B). These data demonstrate that the fusion of high affinity variant 25 to the parent antibody mediated NKG2D-dependent uptake and antigen presentation to elicit potent and rapid immune responses to the parent antibody, which alone was not so immunogenic in mice. Thus, a high affinity variant α1-α2 domain attached to an antigen or immunogen provided potent presentation of the antigen and epitope spreading, effectively serving as a potent adjuvant for immunization.

The demonstrated combined effects of arming circulating NK cells for directed target cell lysis and enhancing antigen presentation are important activities for antibody fusions to modified α1-α2 domains that can provide therapeutic benefit.

Example 8

Figure 25:
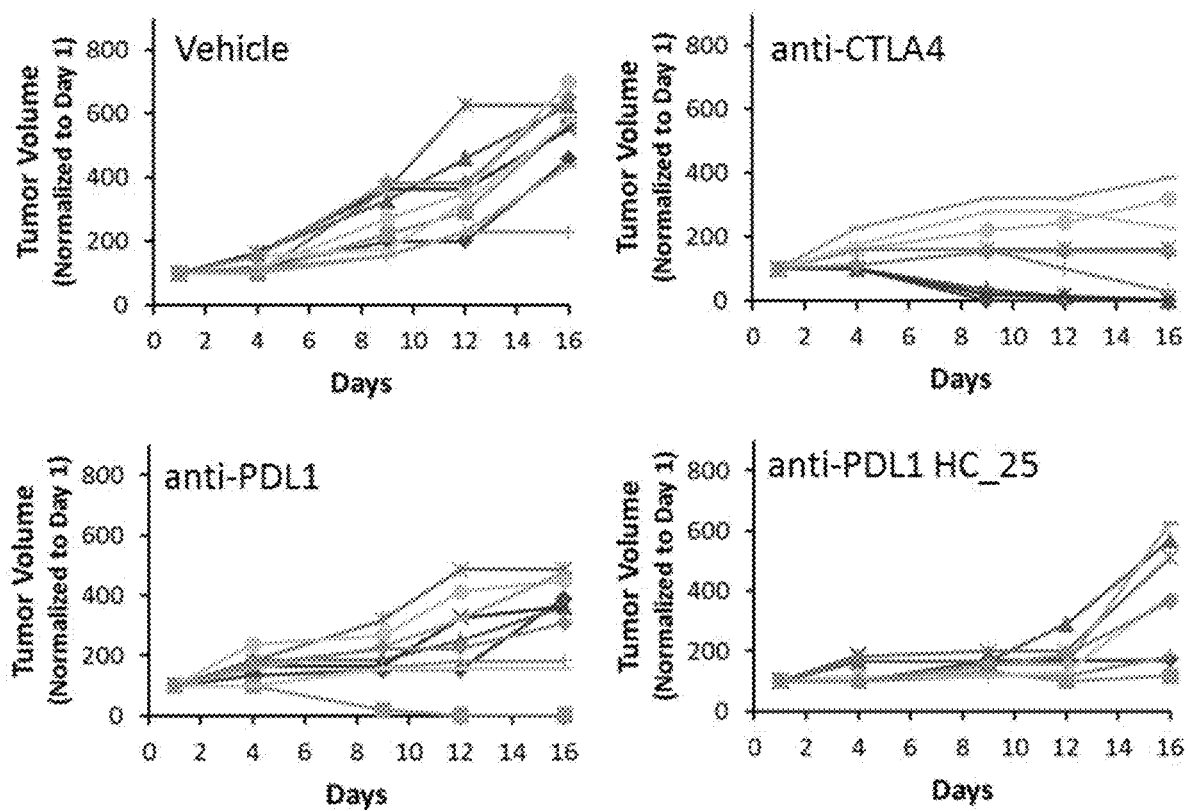
FIG. 25. Anti-tumor activity of an anti-PDL1 fusion to variant 25. Syngeneic MC38 tumors were implanted subcutaneously in C57BL/6 mice, and tumors grew to an average of 100 mm³ before the initiation of treatment. Upon initiation of treatment four cohorts of 10 mice per group were treated parenterally with vehicle, anti-CTLA4 (100 ug i.p.), parent anti-PDL1 (300 ug i.v.), or anti-PDL1 HC_25 fusion (300 ug i.v.) on days 1, 4, and 7. Tumor volumes (cubic mm) were measured in each animal at the indicated times.

Antibody Heavy Chain Fusion to α1-α2 Variant 25 Exhibited Anti-Tumor Activity In Vivo To examine the potential for antigen-specific antibodies fused to modified α1-α2 to have anti-target cell activity, an anti-PDL1 antibody heavy chain fusion to variant 25 α1-α2 was evaluated in a syngeneic MC38 tumor model. MC38 tumors were implanted sub-cutaneously in C57BL/6 mice and tumors grew to an average of 100 $mm^3$ before the initiation of treatment. Upon initiation of treatment, four cohorts of 10 mice per group were treated with vehicle, anti-CTLA4 (100 ug i.p.), parent anti-PDL1 (300 ug i.v.), or anti-PDL1 HC_25 fusion (300 ug i.v.) on days 1, 4, and 7. In FIG. 25, the tumor growth curves showed that anti-PDL1 HC_25 mediated the most effective anti-tumor activity within the first two weeks of treatment. Tumor growth inhibition was significantly better than the established anti-CTLA4 treatment and the parent anti-PDL1 antibody over the first 12 days after initiation of treatment. By day 16, the anti-PDL1 HC_25 treatment began to lose efficacy consistent with the occurrence of an ADA response as observed for trastuzumab fusions (Example 7). The significant anti-tumor activity observed for the antibody heavy chain fusion to variant 25 relative to both the parent antibody and standard anti-CTLA4 treatments demonstrated the impressive therapeutic effect of antibody fusions to modified α1-α2 domains that served as high affinity NKG2D ligands.

What is claimed is:

1. A non-natural, modified α1-α2 domain molecule from a human NKG2D ligand molecule, wherein said domain molecule comprises an amino acid sequence having at least 95% identity to the amino acid sequence of SEQ ID NO: 17, and wherein in said domain molecule, the cysteine at position 103 in SEQ ID NO: 17 is replaced by serine, and the arginine at position 162 in SEQ ID NO: 17 is replaced by glycine.

2. The modified α1-α2 domain molecule of claim 1, wherein said domain molecule comprises the amino acid sequence of SEQ ID NO: 17 but in which the cysteine at position 103 in SEQ ID NO: 17 is replaced by serine, and the arginine at position 162 in SEQ ID NO: 17 is replaced by glycine.

3. The modified α1-α2 domain molecule of claim 1, further comprising an attached heterologous peptide.

4. The molecule of claim 3, wherein the attached heterologous peptide is an antibody, or fragment thereof.

5. The modified α1-α2 domain molecule of claim 3, wherein the heterologous peptide directs the binding of the domain molecule to a target molecule on a target cell, thereby delivering the domain molecule to the target cell.

6. A composition comprising the modified α1-α2 domain molecule of claim 1, and a carrier or excipient.

7. The modified α1-α2 domain molecule of claim 1, which is attached to an immunogen, wherein the α1-α2 domain provides adjuvant activity to accelerate and/or enhance the potency of the immune response of the recipient animal to the immunogen.

8. The modified α1-α2 domain molecule of claim 1, wherein said amino acid sequence has at least 96% identity to the amino acid sequence of SEQ ID NO: 17.

9. The modified α1-α2 domain molecule of claim 1, wherein said amino acid sequence has at least 97% identity to the amino acid sequence of SEQ ID NO: 17.

10. The modified α1-α2 domain molecule of claim 1, wherein said amino acid sequence has at least 98% identity to the amino acid sequence of SEQ ID NO: 17.

11. The modified α1-α2 domain molecule of claim 1, wherein said amino acid sequence has at least 99% identity to the amino acid sequence of SEQ ID NO: 17.

* * * * *

SEQUENCE LISTING

```
<160> NUMBER OF SEQ ID NOS: 83

<210> SEQ ID NO 1
<211> LENGTH: 1126
<212> TYPE: DNA
<213> ORGANISM: Artificial Sequence
<220> FEATURE:
<223> OTHER INFORMATION: Synthetic polynucleotide, encoding alpha3-iFv.1

<400> SEQUENCE: 1 cccccatgg tgcaagttac ccgcagcgag gcctcaggag atcgcgtaac tatcacttgc      60
agagcttctc aggacgtgtc caccgcggtt gcttggtacc agcaaaagcc tggaaaggcg     120
ccgaagctgc tgatctactc cgcctcattc ttgtactcag gagtgcccag tcgatttagt     180
ggtagcggtt ctggtactga tttcaccctt accatcagca gtctccagcc cgaggatttc     240
gctacttatt actgccagca gtcatacacc actcctccca ctttcggcca aggtaccaag     300
gtcgagatta aaggcggaag ctctaggtcc tctagctccg gaggaggtgg ctctggcggc     360
ggcggagaag tccaactggt ggagagcgga ggcggactgg tgcagccagg cggatccttg     420
agacttagct gtgcggcttc gggttttacc tttacttcta ctggcatcag ttgggtcaga     480
caagcgcctg gcaagggact ggaatgggtt ggacgtatct accccactaa tggttcgacg     540
aactatgcgg atagtgtgaa aggtagattc acgatatctg ctgacacctc gaagaatacc     600
gcttaccttc aaatgaatag tttgcgtgcc gaagatactg ctgtctacta ttgcgccaga     660
acctatggaa tatacgacct ttatgtggac tacaccgagt acgtcatgga ttattggggc     720
cagggtacgt tggtgacagt gtcgagtggc ggaagctcta ggtcctctag ctccggagga     780
ggtggctctg gcggcggcgg agacattcag atgactcagt ctcccagttc tcttagtgcc     840
tctggccaaa ttaccgtcac gtgtcgtgct agcggcttct acccgtggaa tatcaccctg     900
agctggcgcc aagacggtgt tagcctgagc cacgacaccc aacaatgggg cgacgtgttg     960
ccagatggcc aaggtaccta ccagacgtgg gttgccaccc gtatttccca gggtgaagag    1020
cagcgtttta cctgctatat ggaacacagc ggccaacata gcacgcatcc ggtgccgagc    1080
ggtaaaggta gccaccatca tcaccaccat tagtaggaat tccgga                   1126

<210> SEQ ID NO 2
```

<211> LENGTH: 1144
<212> TYPE: DNA
<213> ORGANISM: Artificial Sequence
<220> FEATURE:
<223> OTHER INFORMATION: Synthetic polynucleotide, encoding alpha3-iFv.2

<400> SEQUENCE: 2

```
cccccccatgg tgcaagttac ccgcagcgag gcctcaggcg gaagcggaga tcgcgtaact    60
atcacttgca gagcttctca ggacgtgtcc accgcggttg cttggtacca gcaaaagcct   120
ggaaaggcgc cgaagctgct gatctactcc gcctcattct tgtactcagg agtgcccagt   180
cgatttagtg gtagcggttc tggtactgat ttcaccctta ccatcagcag tctccagccc   240
gaggatttcg ctacttatta ctgccagcag tcatacacca ctcctcccac tttcggccaa   300
ggtaccaagg tcgagattaa aggcggaagc tctaggtcct ctagctccgg aggaggtggc   360
tctggcggcg gcggagaagt ccaactggtg gagagcggag cggactggt gcagccaggc   420
ggatccttga gacttagctg tgcggcttcg ggttttacct ttacttctac tggcatcagt   480
tgggtcagac aagcgcctgg caagggactg gaatggggttg acgtatcta ccccactaat   540
ggttcgacga actatgcgga tagtgtgaaa ggtagattca cgatatctgc tgacacctcg   600
aagaataccg cttaccttca aatgaatagt ttgcgtgccg aagatactgc tgtctactat   660
tgcgccagaa cctatggaat atacgacctt tatgtggact acaccgagta cgtcatggat   720
tattggggcc agggtacgtt ggtgacagtg tcgagtggcg gaagctctag gtcctctagc   780
tccggaggag gtggctctgg cggcggcgga gacattcaga tgactcagtc tcccagttct   840
cttagtgcct ctggcggaag cggccaaatt accgtcacgt gtcgtgctag cggcttctac   900
ccgtggaata tcaccctgag ctggcgccaa gacggtgtta gcctgagcca cgacacccaa   960
caatggggcg acgtgttgcc agatggccaa ggtacctacc agacgtgggt tgccaccgt  1020
atttcccagg gtgaagagca gcgttttacc tgctatatgg aacacagcgg ccaacatagc  1080
acgcatccgg tgccgagcgg taaaggtagc caccatcatc accaccatta gtaggaattc  1140
cgga                                                              1144
```

<210> SEQ ID NO 3
<211> LENGTH: 269
<212> TYPE: PRT
<213> ORGANISM: Artificial Sequence
<220> FEATURE:
<223> OTHER INFORMATION: Synthetic peptide iFv (fgfr3)

<400> SEQUENCE: 3

```
Gly Asp Arg Val Thr Ile Thr Cys Arg Ala Ser Gln Asp Val Ser Thr
1               5                   10                  15
Ala Val Ala Trp Tyr Gln Gln Lys Pro Gly Lys Ala Pro Lys Leu Leu
            20                  25                  30
Ile Tyr Ser Ala Ser Phe Leu Tyr Ser Gly Val Pro Ser Arg Phe Ser
        35                  40                  45
Gly Ser Gly Ser Gly Thr Asp Phe Thr Leu Thr Ile Ser Ser Leu Gln
    50                  55                  60
Pro Glu Asp Phe Ala Thr Tyr Tyr Cys Gln Gln Ser Tyr Thr Thr Pro
65                  70                  75                  80
Pro Thr Phe Gly Gln Gly Thr Lys Val Glu Ile Lys Gly Gly Ser Ser
                85                  90                  95
Arg Ser Ser Ser Gly Gly Gly Gly Ser Gly Gly Gly Gly Glu Val
            100                 105                 110
```

```
Gln Leu Val Glu Ser Gly Gly Leu Val Gln Pro Gly Gly Ser Leu
            115                 120                 125
Arg Leu Ser Cys Ala Ala Ser Gly Phe Thr Phe Thr Ser Thr Gly Ile
130                 135                 140
Ser Trp Val Arg Gln Ala Pro Gly Lys Gly Leu Glu Trp Val Gly Arg
145                 150                 155                 160
Ile Tyr Pro Thr Asn Gly Ser Thr Asn Tyr Ala Asp Ser Val Lys Gly
            165                 170                 175
Arg Phe Thr Ile Ser Ala Asp Thr Ser Lys Asn Thr Ala Tyr Leu Gln
            180                 185                 190
Met Asn Ser Leu Arg Ala Glu Asp Thr Ala Val Tyr Tyr Cys Ala Arg
            195                 200                 205
Thr Tyr Gly Ile Tyr Asp Leu Tyr Val Asp Tyr Thr Glu Tyr Val Met
            210                 215                 220
Asp Tyr Trp Gly Gln Gly Thr Leu Val Thr Val Ser Ser Gly Gly Ser
225                 230                 235                 240
Ser Arg Ser Ser Ser Gly Gly Gly Ser Gly Gly Gly Gly Asp
            245                 250                 255
Ile Gln Met Thr Gln Ser Pro Ser Ser Leu Ser Ala Ser
            260                 265
```

<210> SEQ ID NO 4
<211> LENGTH: 807
<212> TYPE: DNA
<213> ORGANISM: Artificial Sequence
<220> FEATURE:
<223> OTHER INFORMATION: Synthetic polynucleotide, encoding iFv (fgfr3)

<400> SEQUENCE: 4

```
ggagatcgcg taactatcac ttgcagagct tctcaggacg tgtccaccgc ggttgcttgg      60
taccagcaaa agcctggaaa ggcgccgaag ctgctgatct actccgcctc attcttgtac     120
tcaggagtgc ccagtcgatt tagtggtagc ggttctggta ctgatttcac ccttaccatc     180
agcagtctcc agcccgagga tttcgctact tattactgcc agcagtcata caccactcct     240
cccactttcg gccaaggtac caaggtcgag attaaaggcg aagctctagg tcctctagc     300
tccggaggag gtggctctgg cggcggcgga gaagtccaac tggtggagag cggaggcgga     360
ctggtgcagc caggcggatc cttgagactt agctgtgcgg cttcgggttt tacctttact     420
tctactggca tcagttgggt cagacaagcg cctggcaagg gactggaatg ggttggacgt     480
atctacccca ctaatggttc gacgaactat gcggatagtg tgaaaggtag attcacgata     540
tctgctgaca cctcgaagaa taccgcttac cttcaaatga atagtttgcg tgccgaagat     600
actgctgtct actattgcgc cagaacctat ggaatatacg acctttatgt ggactacacc     660
gagtacgtca tggattattg gggccagggt acgttggtga cagtgtcgag tggcggaagc     720
tctaggtcct ctagctccgg aggaggtggc tctggcggcg gcggagacat tcagatgact     780
cagtctccca gttctcttag tgcctct                                          807
```

<210> SEQ ID NO 5
<211> LENGTH: 18
<212> TYPE: PRT
<213> ORGANISM: Artificial Sequence
<220> FEATURE:
<223> OTHER INFORMATION: Synthetic peptide linker region

<400> SEQUENCE: 5

Gly Gly Ser Ser Arg Ser Ser Ser Ser Gly Gly Gly Gly Ser Gly Gly 1           5              10              15

Gly Gly

<210> SEQ ID NO 6
<211> LENGTH: 370
<212> TYPE: PRT
<213> ORGANISM: Artificial Sequence
<220> FEATURE:
<223> OTHER INFORMATION: Synthetic peptide alpha3-iFv.1

<400> SEQUENCE: 6

Pro Pro Met Val Gln Val Thr Arg Ser Glu Ala Ser Gly Asp Arg Val
1               5                   10                  15

Thr Ile Thr Cys Arg Ala Ser Gln Asp Val Ser Thr Ala Val Ala Trp
            20                  25                  30

Tyr Gln Gln Lys Pro Gly Lys Ala Pro Lys Leu Leu Ile Tyr Ser Ala
        35                  40                  45

Ser Phe Leu Tyr Ser Gly Val Pro Ser Arg Phe Ser Gly Ser Gly Ser
    50                  55                  60

Gly Thr Asp Phe Thr Leu Thr Ile Ser Ser Leu Gln Pro Glu Asp Phe
65                  70                  75                  80

Ala Thr Tyr Tyr Cys Gln Gln Ser Tyr Thr Thr Pro Pro Thr Phe Gly
                85                  90                  95

Gln Gly Thr Lys Val Glu Ile Lys Gly Gly Ser Ser Arg Ser Ser Ser
            100                 105                 110

Ser Gly Gly Gly Gly Ser Gly Gly Gly Glu Val Gln Leu Val Glu
            115                 120                 125

Ser Gly Gly Gly Leu Val Gln Pro Gly Gly Ser Leu Arg Leu Ser Cys
            130                 135                 140

Ala Ala Ser Gly Phe Thr Phe Ser Thr Gly Ile Ser Trp Val Arg
145                 150                 155                 160

Gln Ala Pro Gly Lys Gly Leu Glu Trp Val Gly Arg Ile Tyr Pro Thr
                165                 170                 175

Asn Gly Ser Thr Asn Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ala Arg Thr Tyr Gly Ile
    210                 215                 220

Tyr Asp Leu Tyr Val Asp Tyr Thr Glu Tyr Val Met Asp Tyr Trp Gly
225                 230                 235                 240

Gln Gly Thr Leu Val Thr Val Ser Ser Gly Gly Ser Ser Arg Ser Ser
                245                 250                 255

Ser Ser Gly Gly Gly Gly Ser Gly Gly Gly Gly Asp Ile Gln Met Thr
            260                 265                 270

Gln Ser Pro Ser Ser Leu Ser Ala Ser Gly Gln Ile Thr Val Thr Cys
        275                 280                 285

Arg Ala Ser Gly Phe Tyr Pro Trp Asn Ile Thr Leu Ser Trp Arg Gln
    290                 295                 300

Asp Gly Val Ser Leu Ser His Asp Thr Gln Gln Trp Gly Asp Val Leu
305                 310                 315                 320

Pro Asp Gly Gln Gly Thr Tyr Gln Thr Trp Val Ala Thr Arg Ile Ser
                325                 330                 335

Gln Gly Glu Glu Gln Arg Phe Thr Cys Tyr Met Glu His Ser Gly Gln
            340                 345                 350

His Ser Thr His Pro Val Pro Ser Gly Lys Gly Ser His His His
        355                 360                 365

His His
    370

<210> SEQ ID NO 7
<211> LENGTH: 376
<212> TYPE: PRT
<213> ORGANISM: Artificial Sequence
<220> FEATURE:
<223> OTHER INFORMATION: Synthetic peptide alpha3-iFv.2

<400> SEQUENCE: 7

Pro Pro Met Val Gln Val Thr Arg Ser Glu Ala Ser Gly Gly Ser Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Gly Gly Ser Ser Arg
            100                 105                 110

Ser Ser Ser Ser Gly Gly Gly Ser Gly Gly Gly Gly Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Thr Phe Thr Ser Thr Gly Ile Ser
145                 150                 155                 160

Trp Val Arg Gln Ala Pro Gly Lys Gly Leu Glu Trp Val Gly Arg Ile
                165                 170                 175

Tyr Pro Thr Asn Gly Ser Thr Asn Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ala Arg Thr
    210                 215                 220

Tyr Gly Ile Tyr Asp Leu Tyr Val Asp Tyr Thr Glu Tyr Val Met Asp
225                 230                 235                 240

Tyr Trp Gly Gln Gly Thr Leu Val Thr Val Ser Ser Gly Gly Ser Ser
                245                 250                 255

Arg Ser Ser Ser Ser Gly Gly Gly Gly Ser Gly Gly Gly Gly Asp Ile
            260                 265                 270

Gln Met Thr Gln Ser Pro Ser Ser Leu Ser Ala Ser Gly Gly Ser Gly
        275                 280                 285

Gln Ile Thr Val Thr Cys Arg Ala Ser Gly Phe Tyr Pro Trp Asn Ile
    290                 295                 300

Thr Leu Ser Trp Arg Gln Asp Gly Val Ser Leu Ser His Asp Thr Gln
305                 310                 315                 320

Gln Trp Gly Asp Val Leu Pro Asp Gly Gln Gly Thr Tyr Gln Thr Trp
                325                 330                 335

Val Ala Thr Arg Ile Ser Gln Gly Glu Glu Gln Arg Phe Thr Cys Tyr
                340                 345                 350

Met Glu His Ser Gly Gln His Ser Thr His Pro Val Pro Ser Gly Lys
            355                 360                 365

Gly Ser His His His His His His
            370                 375

<210> SEQ ID NO 8
<211> LENGTH: 368
<212> TYPE: PRT
<213> ORGANISM: Artificial Sequence
<220> FEATURE:
<223> OTHER INFORMATION: Synthetic peptide alpha3-iFv.3(CD20)

<400> SEQUENCE: 8

Pro Pro Met Val Gln Val Thr Arg Ser Glu Ala Ser Gly Gly Ser Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Gly Gly Ser Ser Arg Ser
            100                 105                 110

Ser Ser Ser Gly Gly Gly Ser Gly Gly Gly Gln Val Gln Leu
            115                 120                 125

Gln Gln Pro Gly Ala Glu Leu Val Lys Pro Gly Ala Ser Val Lys Met
        130                 135                 140

Ser Cys Lys Ala Ser Gly Tyr Thr Phe Thr Ser Tyr Asn Met His Trp
145                 150                 155                 160

Val Lys Gln Thr Pro Gly Arg Gly Leu Glu Trp Ile Gly Ala Ile Tyr
                165                 170                 175

Pro Gly Asn Gly Asp Thr Ser Tyr Asn Gln Lys Phe Lys Gly Lys Ala
            180                 185                 190

Thr Leu Thr Ala Asp Lys Ser Ser Thr Ala Tyr Met Gln Leu Ser
        195                 200                 205

Ser Leu Thr Ser Glu Asp Ser Ala Val Tyr Tyr Cys Ala Arg Ser Thr
    210                 215                 220

Tyr Tyr Gly Gly Asp Trp Tyr Phe Asn Val Trp Gly Ala Gly Thr Thr
225                 230                 235                 240

Val Thr Val Ser Ala Gly Gly Ser Ser Arg Ser Ser Ser Ser Gly Gly
                245                 250                 255

Gly Gly Ser Gly Gly Gly Gly Gln Ile Val Leu Ser Gln Ser Pro Ala
            260                 265                 270

Ile Leu Ser Ala Ser Gly Gly Ser Gln Ile Thr Val Thr Cys Arg Ala
        275                 280                 285

Ser Gly Phe Tyr Pro Trp Asn Ile Thr Leu Ser Trp Arg Gln Asp Gly
    290                 295                 300

Val Ser Leu Ser His Asp Thr Gln Gln Trp Gly Asp Val Leu Pro Asp
305                 310                 315                 320

Gly Gln Gly Thr Tyr Gln Thr Trp Val Ala Thr Arg Ile Ser Gln Gly
            325                 330                 335

Glu Glu Gln Arg Phe Thr Cys Tyr Met Glu His Ser Gly Gln His Ser
        340                 345                 350

Thr His Pro Val Pro Ser Gly Lys Gly Ser His His His His His
    355                 360                 365

<210> SEQ ID NO 9
<211> LENGTH: 561
<212> TYPE: DNA
<213> ORGANISM: Artificial Sequence
<220> FEATURE:
<223> OTHER INFORMATION: Synthetic polynucleotide, encoding ULBP1
      alpha1-alpha2

<400> SEQUENCE: 9
gctgctgagc cccactgtct ctgctacgac tttattataa ctcctaagtc aagaccagag    60
cctcagtggt gcgaagtaca aggtttggtt gacgaaaggc ctttccttca ctacgattgt   120
gtgaaccata aggcaaaggc tttcgccagc ctgggtaaga aggtaaacgt tactaagacg   180
tgggaggagc agacggaaac cctccgtgat gtggttgact tcttaagggg tcagctcctc   240
gatatccaag tggagaattt aatccctatc gaaccgctca ctctgcaggc cagaatgtca   300
tgcgaacatg aagcacacgg tcatggaaga ggtagttggc aattttatt taacggtcaa   360 aaattcctgc tgttcgactc aaacaaccgc aaatggactg cgctgcaccc tggagctaag   420
aagatgactg aaaaatggga gaagaacaga gacgttacca tgttcttcca gaagatttcc   480
ctgggagatt gtaagatgtg gttagaggag ttcttaatgt actgggaaca gatgctggac   540
cccacaaaac cccccatggt g                                             561

<210> SEQ ID NO 10
<211> LENGTH: 567
<212> TYPE: DNA
<213> ORGANISM: Artificial Sequence
<220> FEATURE:
<223> OTHER INFORMATION: Synthetic polynucleotide, encoding ULBP2
      alpha1-alpha2

<400> SEQUENCE: 10
gctgctgagc ccatagtct gtgttacgac atcacagtta ttcccaagtt caggcccgga    60
ccgcgctggt gtgccgtgca aggacaagtc gacgaaaaaa cctttcttca ttacgattgc   120
ggaaataaga ctgtaacgcc agtctctcct ttaggtaaga agttaaacgt cactacggcg   180
tggaaggcac aaaaccccgt cctgcgcgag gtcgtcgaca tcctgactga caattgcgc   240 gacatccagc tcgagaatta cactccaaag gagcctctta ccctgcaggc tagaatgtct   300
tgcgagcaaa aggcagaggg ccactcctcc ggcagctggc agttcagttt cgacggacaa   360
atctttctgt tattcgattc agagaagaga atgtggacta cagttcaccc cggtgcccgt   420
aaaatgaagg agaagtggga aaacgacaaa gtggtggcga tgtcattcca ctatttctcg   480
atgggagact gcatcggttg gctggaagat ttcctcatgg gtatggactc cactttggag   540
ccatcggctg gtgcccccc catggtg                                        567

<210> SEQ ID NO 11
<211> LENGTH: 561
<212> TYPE: DNA
<213> ORGANISM: Artificial Sequence
<220> FEATURE:
<223> OTHER INFORMATION: Synthetic polynucleotide, encoding ULBP3 alpha1-alpha2

<400> SEQUENCE: 11

| gctgctgagc cccacagctt gtggtacaac ttcaccatta tccacttgcc gagacatggc | 60 |
| cagcagtggt gcgaagtgca atcgcaagtc gaccaaaaaa acttcttatc atacgactgc | 120 |
| ggcagcgata aggtcttatc tatgggtcat ttggaggaac agctctacgc gaccgacgcc | 180 |
| tggggtaaac agctcgagat gctccgtgag gttggacaga ggctgagact ggaactggct | 240 |
| gacactgagc tggaagattt cacacctagt ggtccactca cattgcaagt acgcatgagc | 300 |
| tgcgagtgtg aggccgatgg atacattagg ggcagctggc agtttagctt cgacggaagg | 360 |
| aaattcctgc tcttcgacag taacaatagg aagtggactg ttgtgcatgc tggtgcgcgc | 420 |
| agaatgaagg aaaagtggga gaaagatagc ggcctgacga ccttcttcaa gatggtgtct | 480 |
| atgcgtgact gtaagagctg gctcagagat ttcctcatgc atcgcaagaa gaggttagaa | 540 |
| cctaccgctc cccccatggt g | 561 |

<210> SEQ ID NO 12
<211> LENGTH: 561
<212> TYPE: DNA
<213> ORGANISM: Artificial Sequence
<220> FEATURE:
<223> OTHER INFORMATION: Synthetic polynucleotide, encoding ULBP4
      alpha1-alpha2

<400> SEQUENCE: 12

| gctgctgagc ccactctct ttgcttcaac ttcaccatta atccctgag caggcctggt | 60 |
| cagccgtggt gtgaggcgca ggtctttctt aacaagaatc tcttcctcca atacaactct | 120 |
| gataacaaca tggtaaagcc actgggtctc ctgggtaaaa aagtctatgc tacgagcact | 180 |
| tggggagaac tcacccagac tcttggcgag gtaggaagag acctgcgcat gctcctctgc | 240 |
| gatataaagc cccaaattaa gaccagtgat ccgtccactt tacaagtcga atgttctgc | 300 |
| caaagggagg ctgaacgctg caccggagcc tcttggcagt tcgcgaccaa tggcgaaaag | 360 |
| tccctcttgt tcgatgccat gaatatgacc tggaccgtga tcaatcatga ggcctctaag | 420 |
| atcaaggaga cgtggaaaaa ggaccgcggc cttgaaaagt actttaggaa gttgtctaaa | 480 |
| ggagactgcg accattggtt acgcgagttc ctcggccatt gggaagcgat gcccgagcca | 540 |
| acggttagcc cccccatggt g | 561 |

<210> SEQ ID NO 13
<211> LENGTH: 567
<212> TYPE: DNA
<213> ORGANISM: Artificial Sequence
<220> FEATURE:
<223> OTHER INFORMATION: Synthetic polynucleotide, encoding ILBP6
      alpha1-alpha2

<400> SEQUENCE: 13

| gctgctgagc cccactcctt atgctatgat atcaccgtga ttccaaagtt ccgaccagga | 60 |
| ccccgatggt gcgccgtaca gggacaggtc gacgaaaaga cttttttaca ttacgactgc | 120 |
| ggtaacaaga cagtcacacc ggtaagtcct tgggaaaaaa agttaaacgt aaccactgct | 180 |
| tggaaggccc agaaccccgt ccttcgagaa gtagtggata ttttgactga acagctgctt | 240 |
| gacatccagc tggaaaacta cacacccaaa gagcccctga ctcttcaagc gcgtatgtcg | 300 |
| tgtgagcaaa aggccgaagg acacagctcc ggatcctggc agttcagtat cgacggtcag | 360 |
| accttcctcc tcttcgattc agaaaagcgc atgtggacta ctgtgcaccc cggcgctcgt | 420 |

```
aagatgaagg aaaagtggga gaatgataag gacgttgcca tgagttttca ttacattagt    480
atgggagatt gcatcggttg gctggaagac ttcctgatgg gtatggatag tacccttgaa    540
cctagtgccg gagctccccc catggtg                                         567
```

```
<210> SEQ ID NO 14
<211> LENGTH: 483
<212> TYPE: DNA
<213> ORGANISM: Artificial Sequence
<220> FEATURE:
<223> OTHER INFORMATION: Synthetic polynucleotide, encoding OMCP
      alpha1-alpha2

<400> SEQUENCE: 14
```

```
gctgctgctg agccccacaa gcttgcgttc aacttcaatc tggaaataaa cggttcagat     60
acccattcaa ccgtggacgt ttatttagac gattcgcaga taatcacctt tgacggcaag    120
gacatccgcc caactatccc gttcatgata ggtgacgaaa tcttccttcc ttttttataag   180 aatgtgttct ctgagttctt cagtttgttc cgccgcgtcc ctacctcaac cccctacgaa    240
gacttgactt atttctatga atgcgactac accgacaaca atctacatt cgatcaattc     300 tacctgtaca cggtgaaga gtacaccgtg aagactcaag aggctactaa caagaacatg     360
tggctgacca cttccgagtt cagactgaag aagtggttcg acggcgagga ctgtatcatg    420
caccttagaa gtttagtgag gaaaatggaa gatagcaaga agaacagt gcccccatg       480 gtg                                                                   483
```

```
<210> SEQ ID NO 15
<211> LENGTH: 187
<212> TYPE: PRT
<213> ORGANISM: Artificial Sequence
<220> FEATURE:
<223> OTHER INFORMATION: Synthetic peptide ULBP1 alpha1-alpha2

<400> SEQUENCE: 15
```

```
Ala Ala Glu Pro His Cys Leu Cys Tyr Asp Phe Ile Ile Thr Pro Lys
1               5                   10                  15

Ser Arg Pro Glu Pro Gln Trp Cys Glu Val Gln Gly Leu Val Asp Glu
            20                  25                  30

Arg Pro Phe Leu His Tyr Asp Cys Val Asn His Lys Ala Lys Ala Phe
        35                  40                  45

Ala Ser Leu Gly Lys Lys Val Asn Val Thr Lys Thr Trp Glu Glu Gln
    50                  55                  60

Thr Glu Thr Leu Arg Asp Val Val Asp Phe Leu Lys Gly Gln Leu Leu
65                  70                  75                  80

Asp Ile Gln Val Glu Asn Leu Ile Pro Ile Glu Pro Leu Thr Leu Gln
                85                  90                  95

Ala Arg Met Ser Cys Glu His Glu Ala His Gly His Gly Arg Gly Ser
            100                 105                 110

Trp Gln Phe Leu Phe Asn Gly Gln Lys Phe Leu Leu Phe Asp Ser Asn
        115                 120                 125

Asn Arg Lys Trp Thr Ala Leu His Pro Gly Ala Lys Lys Met Thr Glu
    130                 135                 140

Lys Trp Glu Lys Asn Arg Asp Val Thr Met Phe Phe Gln Lys Ile Ser
145                 150                 155                 160

Leu Gly Asp Cys Lys Met Trp Leu Glu Glu Phe Leu Met Tyr Trp Glu
                165                 170                 175
```

Gln Met Leu Asp Pro Thr Lys Pro Pro Met Val
            180                 185

<210> SEQ ID NO 16
<211> LENGTH: 189
<212> TYPE: PRT
<213> ORGANISM: Artificial Sequence
<220> FEATURE:
<223> OTHER INFORMATION: Synthetic peptide ULBP2 alpha1-alpha2

<400> SEQUENCE: 16

Ala Ala Glu Pro His Ser Leu Cys Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
        35                  40                  45

Ser Pro Leu Gly Lys Lys Leu Asn Val Thr Thr Ala Trp Lys Ala Gln
    50                  55                  60

Asn Pro Val Leu Arg Glu Val Val Asp Ile Leu Thr Glu Gln Leu Arg
65                  70                  75                  80

Asp Ile Gln Leu Glu Asn Tyr Thr Pro Lys Glu Pro Leu Thr Leu Gln
                85                  90                  95

Ala Arg Met Ser Cys Glu Gln Lys Ala Glu Gly His Ser Ser Gly Ser
            100                 105                 110

Trp Gln Phe Ser Phe Asp Gly Gln Ile Phe Leu Leu Phe Asp Ser Glu
        115                 120                 125

Lys Arg Met Trp Thr Thr Val His Pro Gly Ala Arg Lys Met Lys Glu
    130                 135                 140

Lys Trp Glu Asn Asp Lys Val Val Ala Met Ser Phe His Tyr Phe Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro Pro Met Val
            180                 185

<210> SEQ ID NO 17
<211> LENGTH: 187
<212> TYPE: PRT
<213> ORGANISM: Artificial Sequence
<220> FEATURE:
<223> OTHER INFORMATION: Synthetic peptide ULBP3 alpha1-alpha2

<400> SEQUENCE: 17

Ala Ala Glu Pro His Ser Leu Trp Tyr Asn Phe Thr Ile Ile His Leu
1               5                   10                  15

Pro Arg His Gly Gln Gln Trp Cys Glu Val Gln Ser Gln Val Asp Gln
            20                  25                  30

Lys Asn Phe Leu Ser Tyr Asp Cys Gly Ser Asp Lys Val Leu Ser Met
        35                  40                  45

Gly His Leu Glu Glu Gln Leu Tyr Ala Thr Asp Ala Trp Gly Lys Gln
    50                  55                  60

Leu Glu Met Leu Arg Glu Val Gly Gln Arg Leu Arg Leu Glu Leu Ala
65                  70                  75                  80

Asp Thr Glu Leu Glu Asp Phe Thr Pro Ser Gly Pro Leu Thr Leu Gln
                85                  90                  95

Val Arg Met Ser Cys Glu Cys Glu Ala Asp Gly Tyr Ile Arg Gly Ser
            100                 105                 110

```
Trp Gln Phe Ser Phe Asp Gly Arg Lys Phe Leu Leu Phe Asp Ser Asn
            115                 120                 125

Asn Arg Lys Trp Thr Val Val His Ala Gly Ala Arg Arg Met Lys Glu
    130                 135                 140

Lys Trp Glu Lys Asp Ser Gly Leu Thr Thr Phe Phe Lys Met Val Ser
145                 150                 155                 160

Met Arg Asp Cys Lys Ser Trp Leu Arg Asp Phe Leu Met His Arg Lys
                165                 170                 175

Lys Arg Leu Glu Pro Thr Ala Pro Pro Met Val
            180                 185
```

<210> SEQ ID NO 18
<211> LENGTH: 187
<212> TYPE: PRT
<213> ORGANISM: Artificial Sequence
<220> FEATURE:
<223> OTHER INFORMATION: Synthetic peptide ULBP4 alpha1-alpha2

<400> SEQUENCE: 18

```
Ala Ala Glu Pro His Ser Leu Cys Phe Asn Phe Thr Ile Lys Ser Leu
1               5                   10                  15

Ser Arg Pro Gly Gln Pro Trp Cys Glu Ala Gln Val Phe Leu Asn Lys
            20                  25                  30

Asn Leu Phe Leu Gln Tyr Asn Ser Asp Asn Asn Met Val Lys Pro Leu
        35                  40                  45

Gly Leu Leu Gly Lys Lys Val Tyr Ala Thr Ser Thr Trp Gly Glu Leu
    50                  55                  60

Thr Gln Thr Leu Gly Glu Val Gly Arg Asp Leu Arg Met Leu Leu Cys
65                  70                  75                  80

Asp Ile Lys Pro Gln Ile Lys Thr Ser Asp Pro Ser Thr Leu Gln Val
                85                  90                  95

Glu Met Phe Cys Gln Arg Glu Ala Glu Arg Cys Thr Gly Ala Ser Trp
            100                 105                 110

Gln Phe Ala Thr Asn Gly Glu Lys Ser Leu Leu Phe Asp Ala Met Asn
        115                 120                 125

Met Thr Trp Thr Val Ile Asn His Glu Ala Ser Lys Ile Lys Glu Thr
    130                 135                 140

Trp Lys Lys Asp Arg Gly Leu Glu Lys Tyr Phe Arg Lys Leu Ser Lys
145                 150                 155                 160

Gly Asp Cys Asp His Trp Leu Arg Glu Phe Leu Gly His Trp Glu Ala
                165                 170                 175

Met Pro Glu Pro Thr Val Ser Pro Pro Met Val
            180                 185
```

<210> SEQ ID NO 19
<211> LENGTH: 189
<212> TYPE: PRT
<213> ORGANISM: Artificial Sequence
<220> FEATURE:
<223> OTHER INFORMATION: Synthetic peptide ULBP6 alpha1-alpha2

<400> SEQUENCE: 19

```
Ala Ala Glu Pro His Ser Leu Cys Tyr Asp Ile Thr Val Ile Pro Lys
1               5                   10                  15

Phe Arg Pro Gly Pro Arg Trp Cys Ala Val Gln Gly Gln Val Asp Glu
            20                  25                  30

Lys Thr Phe Leu His Tyr Asp Cys Gly Asn Lys Thr Val Thr Pro Val
```

```
                35                  40                  45
Ser Pro Leu Gly Lys Lys Leu Asn Val Thr Thr Ala Trp Lys Ala Gln
 50                  55                  60

Asn Pro Val Leu Arg Glu Val Val Asp Ile Leu Thr Glu Gln Leu Leu
 65                  70                  75                  80

Asp Ile Gln Leu Glu Asn Tyr Thr Pro Lys Glu Pro Leu Thr Leu Gln
                 85                  90                  95

Ala Arg Met Ser Cys Glu Gln Lys Ala Glu Gly His Ser Ser Gly Ser
                100                 105                 110

Trp Gln Phe Ser Ile Asp Gly Gln Thr Phe Leu Leu Phe Asp Ser Glu
                115                 120                 125

Lys Arg Met Trp Thr Thr Val His Pro Gly Ala Arg Lys Met Lys Glu
                130                 135                 140

Lys Trp Glu Asn Asp Lys Asp Val Ala Met Ser Phe His Tyr Ile Ser
145                 150                 155                 160

Met Gly Asp Cys Ile Gly Trp Leu Glu Asp Phe Leu Met Gly Met Asp
                165                 170                 175

Ser Thr Leu Glu Pro Ser Ala Gly Ala Pro Pro Met Val
                180                 185

<210> SEQ ID NO 20
<211> LENGTH: 161
<212> TYPE: PRT
<213> ORGANISM: Artificial Sequence
<220> FEATURE:
<223> OTHER INFORMATION: Synthetic peptide OMCP alpha1-alpha2

<400> SEQUENCE: 20

Ala Ala Ala Glu Pro His Lys Leu Ala Phe Asn Phe Asn Leu Glu Ile
 1               5                  10                  15

Asn Gly Ser Asp Thr His Ser Thr Val Asp Val Tyr Leu Asp Asp Ser
                 20                  25                  30

Gln Ile Ile Thr Phe Asp Gly Lys Asp Ile Arg Pro Thr Ile Pro Phe
                 35                  40                  45

Met Ile Gly Asp Glu Ile Phe Leu Pro Phe Tyr Lys Asn Val Phe Ser
 50                  55                  60

Glu Phe Phe Ser Leu Phe Arg Arg Val Pro Thr Ser Thr Pro Tyr Glu
 65                  70                  75                  80

Asp Leu Thr Tyr Phe Tyr Glu Cys Asp Tyr Thr Asp Asn Lys Ser Thr
                 85                  90                  95

Phe Asp Gln Phe Tyr Leu Tyr Asn Gly Glu Glu Tyr Thr Val Lys Thr
                100                 105                 110

Gln Glu Ala Thr Asn Lys Asn Met Trp Leu Thr Thr Ser Glu Phe Arg
                115                 120                 125

Leu Lys Lys Trp Phe Asp Gly Glu Asp Cys Ile Met His Leu Arg Ser
                130                 135                 140

Leu Val Arg Lys Met Glu Asp Ser Lys Arg Arg Thr Val Pro Pro Met
145                 150                 155                 160

Val

<210> SEQ ID NO 21
<211> LENGTH: 580
<212> TYPE: PRT
<213> ORGANISM: Artificial Sequence
<220> FEATURE:
<223> OTHER INFORMATION: Synthetic peptide ULBP1-alpha3-iFv.2
```

<400> SEQUENCE: 21

```
Met Gly Leu Gly Pro Val Phe Leu Leu Leu Ala Gly Ile Phe Pro Phe
1               5                   10                  15

Ala Pro Pro Gly Ala Ala Glu Pro His Cys Leu Cys Tyr Asp Phe
            20                  25                  30

Ile Ile Thr Pro Lys Ser Arg Pro Glu Pro Gln Trp Cys Glu Val Gln
                35                  40                  45

Gly Leu Val Asp Glu Arg Pro Phe Leu His Tyr Asp Cys Val Asn His
    50                  55                  60

Lys Ala Lys Ala Phe Ala Ser Leu Gly Lys Lys Val Asn Val Thr Lys
65                  70                  75                  80

Thr Trp Glu Glu Gln Thr Glu Thr Leu Arg Asp Val Val Asp Phe Leu
                85                  90                  95

Lys Gly Gln Leu Leu Asp Ile Gln Val Glu Asn Leu Ile Pro Ile Glu
            100                 105                 110

Pro Leu Thr Leu Gln Ala Arg Met Ser Cys Glu His Glu Ala His Gly
                115                 120                 125

His Gly Arg Gly Ser Trp Gln Phe Leu Phe Asn Gly Gln Lys Phe Leu
    130                 135                 140

Leu Phe Asp Ser Asn Asn Arg Lys Trp Thr Ala Leu His Pro Gly Ala
145                 150                 155                 160

Lys Lys Met Thr Glu Lys Trp Glu Lys Asn Arg Asp Val Thr Met Phe
                165                 170                 175

Phe Gln Lys Ile Ser Leu Gly Asp Cys Lys Met Trp Leu Glu Glu Phe
            180                 185                 190

Leu Met Tyr Trp Glu Gln Met Leu Asp Pro Thr Lys Pro Pro Met Val
        195                 200                 205

Gln Val Thr Arg Ser Glu Ala Ser Gly Gly Ser Gly Asp Arg Val Thr
    210                 215                 220

Ile Thr Cys Arg Ala Ser Gln Asp Val Ser Thr Ala Val Ala Trp Tyr
225                 230                 235                 240

Gln Gln Lys Pro Gly Lys Ala Pro Lys Leu Leu Ile Tyr Ser Ala Ser
                245                 250                 255

Phe Leu Tyr Ser Gly Val Pro Ser Arg Phe Ser Gly Ser Gly Ser Gly
            260                 265                 270

Thr Asp Phe Thr Leu Thr Ile Ser Ser Leu Gln Pro Glu Asp Phe Ala
        275                 280                 285

Thr Tyr Tyr Cys Gln Gln Ser Tyr Thr Thr Pro Pro Thr Phe Gly Gln
    290                 295                 300

Gly Thr Lys Val Glu Ile Lys Gly Gly Ser Ser Arg Ser Ser Ser Ser
305                 310                 315                 320

Gly Gly Gly Gly Ser Gly Gly Gly Glu Val Gln Leu Val Glu Ser
                325                 330                 335

Gly Gly Gly Leu Val Gln Pro Gly Gly Ser Leu Arg Leu Ser Cys Ala
            340                 345                 350

Ala Ser Gly Phe Thr Phe Thr Ser Thr Gly Ile Ser Trp Val Arg Gln
        355                 360                 365

Ala Pro Gly Lys Gly Leu Glu Trp Val Gly Arg Ile Tyr Pro Thr Asn
    370                 375                 380

Gly Ser Thr Asn Tyr Ala Asp Ser Val Lys Gly Arg Phe Thr Ile Ser
385                 390                 395                 400

Ala Asp Thr Ser Lys Asn Thr Ala Tyr Leu Gln Met Asn Ser Leu Arg
                405                 410                 415
```

```
Ala Glu Asp Thr Ala Val Tyr Tyr Cys Ala Arg Thr Tyr Gly Ile Tyr
            420                 425                 430

Asp Leu Tyr Val Asp Tyr Thr Glu Tyr Val Met Asp Tyr Trp Gly Gln
            435                 440                 445

Gly Thr Leu Val Thr Val Ser Ser Gly Gly Ser Ser Arg Ser Ser Ser
            450                 455                 460

Ser Gly Gly Gly Ser Gly Gly Gly Asp Ile Gln Met Thr Gln
465                 470                 475                 480

Ser Pro Ser Ser Leu Ser Ala Ser Gly Gly Gln Ile Thr Val
                485                 490                 495

Thr Cys Arg Ala Ser Gly Phe Tyr Pro Trp Asn Ile Thr Leu Ser Trp
            500                 505                 510

Arg Gln Asp Gly Val Ser Leu Ser His Asp Thr Gln Gln Trp Gly Asp
            515                 520                 525

Val Leu Pro Asp Gly Gln Gly Thr Tyr Gln Thr Trp Val Ala Thr Arg
            530                 535                 540

Ile Ser Gln Gly Glu Glu Gln Arg Phe Thr Cys Tyr Met Glu His Ser
545                 550                 555                 560

Gly Gln His Ser Thr His Pro Val Pro Ser Gly Lys Gly Ser His His
                565                 570                 575

His His His His
        580

<210> SEQ ID NO 22
<211> LENGTH: 582
<212> TYPE: PRT
<213> ORGANISM: Artificial Sequence
<220> FEATURE:
<223> OTHER INFORMATION: Synthetic peptide ULBP2-alpha3-iFv.2

<400> SEQUENCE: 22

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Cys Tyr Asp Ile
            20                  25                  30

Thr Val Ile Pro Lys Phe Arg Pro Gly Pro Arg Trp Cys Ala Val Gln
            35                  40                  45

Gly Gln Val Asp Glu Lys Thr Phe Leu His Tyr Asp Cys Gly Asn Lys
        50                  55                  60

Thr Val Thr Pro Val Ser Pro Leu Gly Lys Lys Leu Asn Val Thr Thr
65                  70                  75                  80

Ala Trp Lys Ala Gln Asn Pro Val Leu Arg Glu Val Val Asp Ile Leu
                85                  90                  95

Thr Glu Gln Leu Arg Asp Ile Gln Leu Glu Asn Tyr Thr Pro Lys Glu
            100                 105                 110

Pro Leu Thr Leu Gln Ala Arg Met Ser Cys Glu Gln Lys Ala Glu Gly
            115                 120                 125

His Ser Ser Gly Ser Trp Gln Phe Ser Phe Asp Gly Gln Ile Phe Leu
        130                 135                 140

Leu Phe Asp Ser Glu Lys Arg Met Trp Thr Thr Val His Pro Gly Ala
145                 150                 155                 160

Arg Lys Met Lys Glu Lys Trp Glu Asn Asp Lys Val Val Ala Met Ser
                165                 170                 175

Phe His Tyr Phe Ser Met Gly Asp Cys Ile Gly Trp Leu Glu Asp Phe
            180                 185                 190
```

Leu Met Gly Met Asp Ser Thr Leu Glu Pro Ser Ala Gly Ala Pro Pro
        195                 200                 205

Met Val Gln Val Thr Arg Ser Glu Ala Ser Gly Ser Gly Asp Arg
210                 215                 220

Val Thr Ile Thr Cys Arg Ala Ser Gln Asp Val Ser Thr Ala Val Ala
225                 230                 235                 240

Trp Tyr Gln Gln Lys Pro Gly Lys Ala Pro Lys Leu Leu Ile Tyr Ser
                245                 250                 255

Ala Ser Phe Leu Tyr Ser Gly Val Pro Ser Arg Phe Ser Gly Ser Gly
            260                 265                 270

Ser Gly Thr Asp Phe Thr Leu Thr Ile Ser Ser Leu Gln Pro Glu Asp
        275                 280                 285

Phe Ala Thr Tyr Tyr Cys Gln Gln Ser Tyr Thr Thr Pro Pro Thr Phe
290                 295                 300

Gly Gln Gly Thr Lys Val Glu Ile Lys Gly Gly Ser Arg Ser Ser
305                 310                 315                 320

Ser Ser Gly Gly Gly Gly Ser Gly Gly Gly Glu Val Gln Leu Val
                325                 330                 335

Glu Ser Gly Gly Leu Val Gln Pro Gly Gly Ser Leu Arg Leu Ser
            340                 345                 350

Cys Ala Ala Ser Gly Phe Thr Phe Thr Ser Thr Gly Ile Ser Trp Val
                355                 360                 365

Arg Gln Ala Pro Gly Lys Gly Leu Glu Trp Val Gly Arg Ile Tyr Pro
370                 375                 380

Thr Asn Gly Ser Thr Asn Tyr Ala Asp Ser Val Lys Gly Arg Phe Thr
385                 390                 395                 400

Ile Ser Ala Asp Thr Ser Lys Asn Thr Ala Tyr Leu Gln Met Asn Ser
                405                 410                 415

Leu Arg Ala Glu Asp Thr Ala Val Tyr Tyr Cys Ala Arg Thr Tyr Gly
            420                 425                 430

Ile Tyr Asp Leu Tyr Val Asp Tyr Thr Glu Tyr Val Met Asp Tyr Trp
        435                 440                 445

Gly Gln Gly Thr Leu Val Thr Val Ser Ser Gly Gly Ser Ser Arg Ser
450                 455                 460

Ser Ser Ser Gly Gly Gly Gly Ser Gly Gly Gly Asp Ile Gln Met
465                 470                 475                 480

Thr Gln Ser Pro Ser Ser Leu Ser Ala Ser Gly Gly Ser Gln Ile
                485                 490                 495

Thr Val Thr Cys Arg Ala Ser Gly Phe Tyr Pro Trp Asn Ile Thr Leu
            500                 505                 510

Ser Trp Arg Gln Asp Gly Val Ser Leu Ser His Asp Thr Gln Gln Trp
        515                 520                 525

Gly Asp Val Leu Pro Asp Gly Gln Gly Thr Tyr Gln Thr Trp Val Ala
530                 535                 540

Thr Arg Ile Ser Gln Gly Glu Glu Gln Arg Phe Thr Cys Tyr Met Glu
545                 550                 555                 560

His Ser Gly Gln His Ser Thr His Pro Val Pro Ser Gly Lys Gly Ser
                565                 570                 575

His His His His His His
        580

<210> SEQ ID NO 23
<211> LENGTH: 580

<212> TYPE: PRT
<213> ORGANISM: Artificial Sequence
<220> FEATURE:
<223> OTHER INFORMATION: Synthetic peptide ULBP3-alpha3-iFv.2

<400> SEQUENCE: 23

Met Gly Leu Gly Pro Val Phe Leu Leu Leu Ala Gly Ile Phe Pro Phe
1               5                   10                  15

Ala Pro Pro Gly Ala Ala Glu Pro His Ser Leu Trp Tyr Asn Phe
            20                  25                  30

Thr Ile Ile His Leu Pro Arg His Gly Gln Gln Trp Cys Glu Val Gln
                35                  40                  45

Ser Gln Val Asp Gln Lys Asn Phe Leu Ser Tyr Asp Cys Gly Ser Asp
    50                  55                  60

Lys Val Leu Ser Met Gly His Leu Glu Glu Gln Leu Tyr Ala Thr Asp
65                  70                  75                  80

Ala Trp Gly Lys Gln Leu Glu Met Leu Arg Glu Val Gly Gln Arg Leu
                85                  90                  95

Arg Leu Glu Leu Ala Asp Thr Glu Leu Glu Asp Phe Thr Pro Ser Gly
            100                 105                 110

Pro Leu Thr Leu Gln Val Arg Met Ser Cys Glu Cys Glu Ala Asp Gly
        115                 120                 125

Tyr Ile Arg Gly Ser Trp Gln Phe Ser Phe Asp Gly Arg Lys Phe Leu
130                 135                 140

Leu Phe Asp Ser Asn Asn Arg Lys Trp Thr Val Val His Ala Gly Ala
145                 150                 155                 160

Arg Arg Met Lys Glu Lys Trp Glu Lys Asp Ser Gly Leu Thr Thr Phe
                165                 170                 175

Phe Lys Met Val Ser Met Arg Asp Cys Lys Ser Trp Leu Arg Asp Phe
            180                 185                 190

Leu Met His Arg Lys Lys Arg Leu Glu Pro Thr Ala Pro Pro Met Val
        195                 200                 205

Gln Val Thr Arg Ser Glu Ala Ser Gly Gly Ser Gly Asp Arg Val Thr
210                 215                 220

Ile Thr Cys Arg Ala Ser Gln Asp Val Ser Thr Ala Val Ala Trp Tyr
225                 230                 235                 240

Gln Gln Lys Pro Gly Lys Ala Pro Lys Leu Leu Ile Tyr Ser Ala Ser
                245                 250                 255

Phe Leu Tyr Ser Gly Val Pro Ser Arg Phe Ser Gly Ser Gly Ser Gly
            260                 265                 270

Thr Asp Phe Thr Leu Thr Ile Ser Ser Leu Gln Pro Glu Asp Phe Ala
        275                 280                 285

Thr Tyr Tyr Cys Gln Gln Ser Tyr Thr Thr Pro Pro Thr Phe Gly Gln
290                 295                 300

Gly Thr Lys Val Glu Ile Lys Gly Gly Ser Arg Ser Ser Ser
305                 310                 315                 320

Gly Gly Gly Gly Ser Gly Gly Gly Glu Val Gln Leu Val Glu Ser
            325                 330                 335

Gly Gly Gly Leu Val Gln Pro Gly Gly Ser Leu Arg Leu Ser Cys Ala
        340                 345                 350

Ala Ser Gly Phe Thr Phe Thr Ser Thr Gly Ile Ser Trp Val Arg Gln
            355                 360                 365

Ala Pro Gly Lys Gly Leu Glu Trp Val Gly Arg Ile Tyr Pro Thr Asn
        370                 375                 380

```
Gly Ser Thr Asn Tyr Ala Asp Ser Val Lys Gly Arg Phe Thr Ile Ser
385                 390                 395                 400

Ala Asp Thr Ser Lys Asn Thr Ala Tyr Leu Gln Met Asn Ser Leu Arg
            405                 410                 415

Ala Glu Asp Thr Ala Val Tyr Tyr Cys Ala Arg Thr Tyr Gly Ile Tyr
            420                 425                 430

Asp Leu Tyr Val Asp Tyr Thr Glu Tyr Val Met Asp Tyr Trp Gly Gln
            435                 440                 445

Gly Thr Leu Val Thr Val Ser Ser Gly Gly Ser Arg Ser Ser Ser
        450                 455                 460

Ser Gly Gly Gly Ser Gly Gly Gly Asp Ile Gln Met Thr Gln
465                 470                 475                 480

Ser Pro Ser Ser Leu Ser Ala Ser Gly Gly Ser Gln Ile Thr Val
            485                 490                 495

Thr Cys Arg Ala Ser Gly Phe Tyr Pro Trp Asn Ile Thr Leu Ser Trp
            500                 505                 510

Arg Gln Asp Gly Val Ser Leu Ser His Asp Thr Gln Gln Trp Gly Asp
            515                 520                 525

Val Leu Pro Asp Gly Gln Gly Thr Tyr Gln Thr Trp Val Ala Thr Arg
530                 535                 540

Ile Ser Gln Gly Glu Glu Gln Arg Phe Thr Cys Tyr Met Glu His Ser
545                 550                 555                 560

Gly Gln His Ser Thr His Pro Val Pro Ser Gly Lys Gly Ser His His
            565                 570                 575

His His His His
            580

<210> SEQ ID NO 24
<211> LENGTH: 580
<212> TYPE: PRT
<213> ORGANISM: Artificial Sequence
<220> FEATURE:
<223> OTHER INFORMATION: Synthetic peptide ULBP4-alpha3-iFv.2

<400> SEQUENCE: 24

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Cys Phe Asn Phe
            20                  25                  30

Thr Ile Lys Ser Leu Ser Arg Pro Gly Gln Pro Trp Cys Glu Ala Gln
            35                  40                  45

Val Phe Leu Asn Lys Asn Leu Phe Leu Gln Tyr Asn Ser Asp Asn Asn
        50                  55                  60

Met Val Lys Pro Leu Gly Leu Leu Gly Lys Lys Val Tyr Ala Thr Ser
65                  70                  75                  80

Thr Trp Gly Glu Leu Thr Gln Thr Leu Gly Glu Val Gly Arg Asp Leu
                85                  90                  95

Arg Met Leu Leu Cys Asp Ile Lys Pro Gln Ile Lys Thr Ser Asp Pro
            100                 105                 110

Ser Thr Leu Gln Val Glu Met Phe Cys Gln Arg Glu Ala Glu Arg Cys
            115                 120                 125

Thr Gly Ala Ser Trp Gln Phe Ala Thr Asn Gly Glu Lys Ser Leu Leu
        130                 135                 140

Phe Asp Ala Met Asn Met Thr Trp Thr Val Ile Asn His Glu Ala Ser
145                 150                 155                 160
```

```
Lys Ile Lys Glu Thr Trp Lys Lys Asp Arg Gly Leu Glu Lys Tyr Phe
            165                 170                 175

Arg Lys Leu Ser Lys Gly Asp Cys Asp His Trp Leu Arg Glu Phe Leu
            180                 185                 190

Gly His Trp Glu Ala Met Pro Glu Pro Thr Val Ser Pro Pro Met Val
            195                 200                 205

Gln Val Thr Arg Ser Glu Ala Ser Gly Gly Ser Gly Asp Arg Val Thr
            210                 215                 220

Ile Thr Cys Arg Ala Ser Gln Asp Val Ser Thr Ala Val Ala Trp Tyr
225                 230                 235                 240

Gln Gln Lys Pro Gly Lys Ala Pro Lys Leu Leu Ile Tyr Ser Ala Ser
            245                 250                 255

Phe Leu Tyr Ser Gly Val Pro Ser Arg Phe Ser Gly Ser Gly Ser Gly
            260                 265                 270

Thr Asp Phe Thr Leu Thr Ile Ser Ser Leu Gln Pro Glu Asp Phe Ala
            275                 280                 285

Thr Tyr Tyr Cys Gln Gln Ser Tyr Thr Thr Pro Pro Thr Phe Gly Gln
            290                 295                 300

Gly Thr Lys Val Glu Ile Lys Gly Gly Ser Ser Arg Ser Ser Ser Ser
305                 310                 315                 320

Gly Gly Gly Gly Ser Gly Gly Gly Glu Val Gln Leu Val Glu Ser
            325                 330                 335

Gly Gly Gly Leu Val Gln Pro Gly Gly Ser Leu Arg Leu Ser Cys Ala
            340                 345                 350

Ala Ser Gly Phe Thr Phe Thr Ser Thr Gly Ile Ser Trp Val Arg Gln
            355                 360                 365

Ala Pro Gly Lys Gly Leu Glu Trp Val Gly Arg Ile Tyr Pro Thr Asn
            370                 375                 380

Gly Ser Thr Asn Tyr Ala Asp Ser Val Lys Gly Arg Phe Thr Ile Ser
385                 390                 395                 400

Ala Asp Thr Ser Lys Asn Thr Ala Tyr Leu Gln Met Asn Ser Leu Arg
            405                 410                 415

Ala Glu Asp Thr Ala Val Tyr Tyr Cys Ala Arg Thr Tyr Gly Ile Tyr
            420                 425                 430

Asp Leu Tyr Val Asp Tyr Thr Glu Tyr Val Met Asp Tyr Trp Gly Gln
            435                 440                 445

Gly Thr Leu Val Thr Val Ser Ser Gly Gly Ser Arg Ser Ser Ser
450                 455                 460

Ser Gly Gly Gly Gly Ser Gly Gly Gly Gly Asp Ile Gln Met Thr Gln
465                 470                 475                 480

Ser Pro Ser Ser Leu Ser Ala Ser Gly Gly Ser Gly Gln Ile Thr Val
            485                 490                 495

Thr Cys Arg Ala Ser Gly Phe Tyr Pro Trp Asn Ile Thr Leu Ser Trp
            500                 505                 510

Arg Gln Asp Gly Val Ser Leu Ser His Asp Thr Gln Gln Trp Gly Asp
            515                 520                 525

Val Leu Pro Asp Gly Gln Gly Thr Tyr Gln Thr Trp Val Ala Thr Arg
            530                 535                 540

Ile Ser Gln Gly Glu Glu Gln Arg Phe Thr Cys Tyr Met Glu His Ser
545                 550                 555                 560

Gly Gln His Ser Thr His Pro Val Pro Ser Gly Lys Gly Ser His His
            565                 570                 575

His His His His
```

<210> SEQ ID NO 25
<211> LENGTH: 582
<212> TYPE: PRT
<213> ORGANISM: Artificial Sequence
<220> FEATURE:
<223> OTHER INFORMATION: Synthetic peptide ULBP6-alpha3-iFv.2

<400> SEQUENCE: 25

```
Met Gly Leu Gly Pro Val Phe Leu Leu Leu Ala Gly Ile Phe Pro Phe
1               5                   10                  15

Ala Pro Pro Gly Ala Ala Glu Pro His Ser Leu Cys Tyr Asp Ile
            20                  25                  30

Thr Val Ile Pro Lys Phe Arg Pro Gly Pro Arg Trp Cys Ala Val Gln
        35                  40                  45

Gly Gln Val Asp Glu Lys Thr Phe Leu His Tyr Asp Cys Gly Asn Lys
    50                  55                  60

Thr Val Thr Pro Val Ser Pro Leu Gly Lys Lys Leu Asn Val Thr Thr
65                  70                  75                  80

Ala Trp Lys Ala Gln Asn Pro Val Leu Arg Glu Val Val Asp Ile Leu
                85                  90                  95

Thr Glu Gln Leu Leu Asp Ile Gln Leu Glu Asn Tyr Thr Pro Lys Glu
            100                 105                 110

Pro Leu Thr Leu Gln Ala Arg Met Ser Cys Glu Gln Lys Ala Glu Gly
        115                 120                 125

His Ser Ser Gly Ser Trp Gln Phe Ser Ile Asp Gly Gln Thr Phe Leu
    130                 135                 140

Leu Phe Asp Ser Glu Lys Arg Met Trp Thr Thr Val His Pro Gly Ala
145                 150                 155                 160

Arg Lys Met Lys Glu Lys Trp Glu Asn Asp Lys Asp Val Ala Met Ser
                165                 170                 175

Phe His Tyr Ile Ser Met Gly Asp Cys Ile Gly Trp Leu Glu Asp Phe
            180                 185                 190

Leu Met Gly Met Asp Ser Thr Leu Glu Pro Ser Ala Gly Ala Pro Pro
        195                 200                 205

Met Val Gln Val Thr Arg Ser Glu Ala Ser Gly Gly Ser Gly Asp Arg
    210                 215                 220

Val Thr Ile Thr Cys Arg Ala Ser Gln Asp Val Ser Thr Ala Val Ala
225                 230                 235                 240

Trp Tyr Gln Gln Lys Pro Gly Lys Ala Pro Lys Leu Leu Ile Tyr Ser
                245                 250                 255

Ala Ser Phe Leu Tyr Ser Gly Val Pro Ser Arg Phe Ser Gly Ser Gly
            260                 265                 270

Ser Gly Thr Asp Phe Thr Leu Thr Ile Ser Ser Leu Gln Pro Glu Asp
        275                 280                 285

Phe Ala Thr Tyr Tyr Cys Gln Gln Ser Tyr Thr Thr Pro Pro Thr Phe
    290                 295                 300

Gly Gln Gly Thr Lys Val Glu Ile Lys Gly Gly Ser Ser Arg Ser Ser
305                 310                 315                 320

Ser Ser Gly Gly Gly Gly Ser Gly Gly Gly Glu Val Gln Leu Val
                325                 330                 335

Glu Ser Gly Gly Gly Leu Val Gln Pro Gly Gly Ser Leu Arg Leu Ser
            340                 345                 350

Cys Ala Ala Ser Gly Phe Thr Phe Thr Ser Thr Gly Ile Ser Trp Val
```

```
                    355                 360                 365
Arg Gln Ala Pro Gly Lys Gly Leu Glu Trp Val Gly Arg Ile Tyr Pro
            370                 375                 380

Thr Asn Gly Ser Thr Asn Tyr Ala Asp Ser Val Lys Gly Arg Phe Thr
385                 390                 395                 400

Ile Ser Ala Asp Thr Ser Lys Asn Thr Ala Tyr Leu Gln Met Asn Ser
                405                 410                 415

Leu Arg Ala Glu Asp Thr Ala Val Tyr Tyr Cys Ala Arg Thr Tyr Gly
            420                 425                 430

Ile Tyr Asp Leu Tyr Val Asp Tyr Thr Glu Tyr Val Met Asp Tyr Trp
                435                 440                 445

Gly Gln Gly Thr Leu Val Thr Val Ser Ser Gly Ser Ser Arg Ser
            450                 455                 460

Ser Ser Ser Gly Gly Gly Ser Gly Gly Gly Asp Ile Gln Met
465                 470                 475                 480

Thr Gln Ser Pro Ser Ser Leu Ser Ala Ser Gly Gly Ser Gly Gln Ile
                485                 490                 495

Thr Val Thr Cys Arg Ala Ser Gly Phe Tyr Pro Trp Asn Ile Thr Leu
            500                 505                 510

Ser Trp Arg Gln Asp Gly Val Ser Leu Ser His Asp Thr Gln Gln Trp
                515                 520                 525

Gly Asp Val Leu Pro Asp Gly Gln Gly Thr Tyr Gln Thr Trp Val Ala
            530                 535                 540

Thr Arg Ile Ser Gln Gly Glu Glu Gln Arg Phe Thr Cys Tyr Met Glu
545                 550                 555                 560

His Ser Gly Gln His Ser Thr His Pro Val Pro Ser Gly Lys Gly Ser
                565                 570                 575

His His His His His His
            580

<210> SEQ ID NO 26
<211> LENGTH: 553
<212> TYPE: PRT
<213> ORGANISM: Artificial Sequence
<220> FEATURE:
<223> OTHER INFORMATION: Synthetic peptide OMCP-alpha3-iFv.2

<400> SEQUENCE: 26

Met Gly Leu Gly Pro Val Phe Leu Leu Leu Ala Gly Ile Phe Pro Phe
1               5                   10                  15

Ala Pro Pro Gly Ala Ala Ala Glu Pro His Lys Leu Ala Phe Asn Phe
            20                  25                  30

Asn Leu Glu Ile Asn Gly Ser Asp Thr His Ser Thr Val Asp Val Tyr
        35                  40                  45

Leu Asp Asp Ser Gln Ile Ile Thr Phe Asp Gly Lys Asp Ile Arg Pro
    50                  55                  60

Thr Ile Pro Phe Met Ile Gly Asp Glu Ile Phe Leu Pro Phe Tyr Lys
65                  70                  75                  80

Asn Val Phe Ser Glu Phe Phe Ser Leu Phe Arg Arg Val Pro Thr Ser
                85                  90                  95

Thr Pro Tyr Glu Asp Leu Thr Tyr Phe Tyr Glu Cys Asp Tyr Thr Asp
            100                 105                 110

Asn Lys Ser Thr Phe Asp Gln Phe Tyr Leu Tyr Asn Gly Glu Glu Tyr
        115                 120                 125

Thr Val Lys Thr Gln Glu Ala Thr Asn Lys Asn Met Trp Leu Thr Thr
```

```
              130                 135                 140
Ser Glu Phe Arg Leu Lys Lys Trp Phe Asp Gly Glu Asp Cys Ile Met
145                 150                 155                 160

His Leu Arg Ser Leu Val Arg Lys Met Glu Asp Ser Lys Arg Arg Thr
                165                 170                 175

Val Pro Pro Met Val Gln Val Thr Arg Ser Glu Ala Ser Gly Gly Ser
                180                 185                 190

Gly Asp Arg Val Thr Ile Thr Cys Arg Ala Ser Gln Asp Val Ser Thr
                195                 200                 205

Ala Val Ala Trp Tyr Gln Gln Lys Pro Gly Lys Ala Pro Lys Leu Leu
                210                 215                 220

Ile Tyr Ser Ala Ser Phe Leu Tyr Ser Gly Val Pro Ser Arg Phe Ser
225                 230                 235                 240

Gly Ser Gly Ser Gly Thr Asp Phe Thr Leu Thr Ile Ser Ser Leu Gln
                245                 250                 255

Pro Glu Asp Phe Ala Thr Tyr Tyr Cys Gln Gln Ser Tyr Thr Thr Pro
                260                 265                 270

Pro Thr Phe Gly Gln Gly Thr Lys Val Glu Ile Lys Gly Gly Ser Ser
                275                 280                 285

Arg Ser Ser Ser Ser Gly Gly Gly Ser Gly Gly Gly Gly Glu Val
290                 295                 300

Gln Leu Val Glu Ser Gly Gly Gly Leu Val Gln Pro Gly Gly Ser Leu
305                 310                 315                 320

Arg Leu Ser Cys Ala Ala Ser Gly Phe Thr Phe Thr Ser Thr Gly Ile
                325                 330                 335

Ser Trp Val Arg Gln Ala Pro Gly Lys Gly Leu Glu Trp Val Gly Arg
                340                 345                 350

Ile Tyr Pro Thr Asn Gly Ser Thr Asn Tyr Ala Asp Ser Val Lys Gly
                355                 360                 365

Arg Phe Thr Ile Ser Ala Asp Thr Ser Lys Asn Thr Ala Tyr Leu Gln
                370                 375                 380

Met Asn Ser Leu Arg Ala Glu Asp Thr Ala Val Tyr Tyr Cys Ala Arg
385                 390                 395                 400

Thr Tyr Gly Ile Tyr Asp Leu Tyr Val Asp Tyr Thr Glu Tyr Val Met
                405                 410                 415

Asp Tyr Trp Gly Gln Gly Thr Leu Val Thr Val Ser Ser Gly Gly Ser
                420                 425                 430

Ser Arg Ser Ser Ser Ser Gly Gly Gly Gly Ser Gly Gly Gly Gly Asp
                435                 440                 445

Ile Gln Met Thr Gln Ser Pro Ser Ser Leu Ser Ala Ser Gly Gly Ser
                450                 455                 460

Gly Gln Ile Thr Val Thr Cys Arg Ala Ser Gly Phe Tyr Pro Trp Asn
465                 470                 475                 480

Ile Thr Leu Ser Trp Arg Gln Asp Gly Val Ser Leu Ser His Asp Thr
                485                 490                 495

Gln Gln Trp Gly Asp Val Leu Pro Asp Gly Gln Gly Thr Tyr Gln Thr
                500                 505                 510

Trp Val Ala Thr Arg Ile Ser Gln Gly Glu Glu Gln Arg Phe Thr Cys
                515                 520                 525

Tyr Met Glu His Ser Gly Gln His Ser Thr His Pro Val Pro Ser Gly
                530                 535                 540

Lys Gly Ser His His His His His His
545                 550
```

<210> SEQ ID NO 27
<211> LENGTH: 507
<212> TYPE: DNA
<213> ORGANISM: Artificial Sequence
<220> FEATURE:
<223> OTHER INFORMATION: Synthetic polynucleotide, encoding alpha1-
      alpha2 variant 15

<400> SEQUENCE: 27

| | | | | | |
|---|---|---|---|---|---|
| gctgctgagc | cacacagtct | ccgctacaac | cttacggtgt | tgagctggga | cggctctgtc | 60 |
| cagagtggct | ttctgactga | ggtacatctc | gatggtcagc | ccttcctccg | atgcgacaga | 120 |
| caaaagtgca | gggccaagcc | acagggccaa | tgggccgaag | atgtacttgg | caataagact | 180 |
| tgggacagag | aaaccagaga | tctgactggc | tggggtaagg | acttacgcat | gactctcgca | 240 |
| cacattaaag | accagaagga | aggtcttcat | tcgctccagg | aaattagagt | ctgtgaaatc | 300 |
| catgaagaca | cagcacaag | aagttcccaa | catttctact | acgacggcga | gctgttctta | 360 |
| tcacagaatt | tagagaccaa | cgagtggaca | atgccccaaa | gctcgagggc | ccagaccctc | 420 |
| gctatgaatg | tgaggaattt | ccttaaggag | gacgctatgg | aaactgacac | ccactaccat | 480 |
| gcgatgcgcg | ccgattgcct | gcaggaa | | | | 507 |

<210> SEQ ID NO 28
<211> LENGTH: 507
<212> TYPE: DNA
<213> ORGANISM: Artificial Sequence
<220> FEATURE:
<223> OTHER INFORMATION: Synthetic polynucleotide, encoding alpha1-
      alpha2 variant 16

<400> SEQUENCE: 28

| | | | | | |
|---|---|---|---|---|---|
| gctgctgagc | cacacagtct | ccgctacaac | cttacggtgt | tgagctggga | cggctctgtc | 60 |
| cagagtggct | ttctgactga | ggtacatctc | gatggtcagc | ccttcctccg | atgcgacaga | 120 |
| caaaagtgca | gggccaagcc | acagggccaa | tgggccgaag | atgtacttgg | caataagact | 180 |
| tgggacagag | aaaccagaga | tctgactggc | tggggtaagg | acttacgcat | gactctcgca | 240 |
| cacattaaag | accagaagga | aggtcttcat | tcgctccagg | aaattagagt | ctgtgaaatc | 300 |
| catgaagaca | cagcacaag | aagttcccaa | catttctact | acgacggcga | gctgttctta | 360 |
| tcacagaatt | tagagaccct | cgagtggaca | atgccccaaa | gctcgagggc | ccagaccctc | 420 |
| gctatgaatg | tgaggaattt | ccttaaggag | gacgctatgg | aaactgacac | ccactaccat | 480 |
| gcgatgcgcg | ccgattgcct | gcaggaa | | | | 507 |

<210> SEQ ID NO 29
<211> LENGTH: 507
<212> TYPE: DNA
<213> ORGANISM: Artificial Sequence
<220> FEATURE:
<223> OTHER INFORMATION: Synthetic polynucleotide, encoding alpha1-
      alpha2 variant 17

<400> SEQUENCE: 29

| | | | | | |
|---|---|---|---|---|---|
| gctgctgagc | cacacagtct | ccgctacaac | cttacggtgt | tgagctggga | cggctctgtc | 60 |
| cagagtggct | ttctgactga | ggtacatctc | gatggtcagc | ccttcctccg | atgcgacaga | 120 |
| caaaagtgca | gggccaagcc | acagggccaa | tgggccgaag | atgtacttgg | caataagact | 180 |
| tgggacagag | aaaccagaga | tctgactctc | tggggtaagg | acttacgcat | gactctcgca | 240 |
| cacattaaag | accagaagga | aggtcttcat | tcgctccagg | aaattagagt | ctgtgaaatc | 300 |

```
catgaagaca acagcacaag aagttcccaa catttctact acgacggcga gctgttctta    360
tcacagaatt tagagaccct cgagtggaca atgcccaaa gctcgagggc ccagaccctc     420
gctatgaatg tgaggaattt ccttaaggag gacgctatgg aaactgacac ccactaccat    480
gcgatgcgcg ccgattgcct gcaggaa                                        507
```

<210> SEQ ID NO 30
<211> LENGTH: 507
<212> TYPE: DNA
<213> ORGANISM: Artificial Sequence
<220> FEATURE:
<223> OTHER INFORMATION: Synthetic polynucleotide, encoding alpha1-
      alpha2 variant 18

<400> SEQUENCE: 30

```
gctgctgagc cacacagtct ccgctacaac cttacggtgt tgagctggga cggctctgtc     60
cagcccggct ttctgactga ggtacatctc gatggtcagc ccttcctccg atgcgacaga    120
caaaagtgca gggccaagcc acagggccaa tgggccgaag atgtacttgg caataagact    180
tgggacagag aaaccagaga tctgactctc tggggtaagg acttacgcat gactctcgca    240
cacattaaag accagaagga aggtcttcat tcgctccagg aaattagagt ctgtgaaatc    300
catgaagaca acagcacaag aagttcccaa catttctact acgacggcga gctgttctta    360
tcacagaatt tagagaccct cgagtggaca atgcccaaa gctcgagggc ccagaccctc     420
gctatgaatg tgaggaattt ccttaaggag gacgctatgg aaactgacac ccactaccat    480
gcgatgcgcg ccgattgcct gcaggaa                                        507
```

<210> SEQ ID NO 31
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 15

<400> SEQUENCE: 31

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Asn Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
```

```
            165                 170                 175
Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
            195                 200                 205

Gln Asp Val Ser Thr Ala Val Ala Trp Tyr Gln Gln Lys Pro Gly Lys
        210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
            275                 280                 285

Lys Gly Gly Ser Ser Arg Ser Ser Ser Gly Gly Gly Gly Ser Gly
            290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
            355                 360                 365

Asp Ser Val Lys Gly Arg Phe Thr Ile Ser Ala Asp Thr Ser Lys Asn
        370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Gly Ser
            435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
        530                 535                 540

Pro Val Pro Ser Gly Lys Gly Ser His His His His His
545                 550                 555

<210> SEQ ID NO 32
<211> LENGTH: 558
<212> TYPE: PRT
<213> ORGANISM: Artificial Sequence
```

```
<220> FEATURE:
<223> OTHER INFORMATION: Synthetic peptide MICA alpha1-alpha2 variant 16

<400> SEQUENCE: 32
```

| | | | | | | | | | | | | | | |
|---|---|---|---|---|---|---|---|---|---|---|---|---|---|---|
| Glu | Pro | His | Ser | Leu | Arg | Tyr | Asn | Leu | Thr | Val | Leu | Ser | Trp | Asp | Gly |
| 1 | | | | 5 | | | | | 10 | | | | | 15 |

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
 50                  55                  60

Asp Leu Thr Gly Trp Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Gly Ser Gly
290                 295                 300

Gly Gly Gly Glu Val Gln Leu Val Glu Ser Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

-continued

```
Tyr Tyr Cys Ala Arg Thr Tyr Gly Ile Tyr Asp Leu Tyr Val Asp Tyr
            405                 410                 415

Thr Glu Tyr Val Met Asp Tyr Trp Gly Gln Gly Thr Leu Val Thr Val
        420                 425                 430

Ser Ser Gly Gly Ser Ser Arg Ser Ser Ser Gly Gly Gly Gly Ser
        435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
530                 535                 540

Pro Val Pro Ser Gly Lys Gly Ser His His His His His
545                 550                 555

<210> SEQ ID NO 33
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 17

<400> SEQUENCE: 33

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Leu Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205
```

Gln Asp Val Ser Thr Ala Val Ala Trp Tyr Gln Gln Lys Pro Gly Lys
     210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
        275                 280                 285

Lys Gly Gly Ser Ser Arg Ser Ser Ser Gly Gly Gly Gly Ser Gly
290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
        355                 360                 365

Asp Ser Val Lys Gly Arg Phe Thr Ile Ser Ala Asp Thr Ser Lys Asn
370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Gly Ser
        435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
        515                 520                 525

Gln Arg Phe Thr Cys Tyr Met Glu His Ser Gly Gln His Ser Thr His
530                 535                 540

Pro Val Pro Ser Gly Lys Gly Ser His His His His His
545                 550                 555

<210> SEQ ID NO 34
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 18

<400> SEQUENCE: 34

Glu Pro His Ser Leu Arg Tyr Asn Leu Thr Val Leu Ser Trp Asp Gly
1               5                   10                  15

```
Ser Val Gln Pro Gly Phe Leu Thr Glu Val His Leu Asp Gly Gln Pro
         20                  25                  30

Phe Leu Arg Cys Asp Arg Gln Lys Cys Arg Ala Lys Pro Gln Gly Gln
             35                  40                  45

Trp Ala Glu Asp Val Leu Gly Asn Lys Thr Trp Asp Arg Glu Thr Arg
 50                  55                  60

Asp Leu Thr Leu Trp Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
             100                 105                 110

Asp Gly Glu Leu Phe Leu Ser Gln Asn Leu Glu Thr Leu Glu Trp Thr
         115                 120                 125

Met Pro Gln Ser Ser Arg Ala Gln Thr Leu Ala Met Asn Val Arg Asn
 130                 135                 140

Phe Leu Lys Glu Asp Ala Met Glu Thr Asp Thr His Tyr His Ala Met
145                 150                 155                 160

Arg Ala Asp Cys Leu Gln Glu Leu Arg Arg Tyr Leu Lys Ser Gly Val
                 165                 170                 175

Val Leu Arg Arg Thr Val Pro Pro Met Val Gln Val Thr Arg Ser Glu
             180                 185                 190

Ala Ser Gly Gly Ser Gly Asp Arg Val Thr Ile Thr Cys Arg Ala Ser
         195                 200                 205

Gln Asp Val Ser Thr Ala Val Ala Trp Tyr Gln Gln Lys Pro Gly Lys
 210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                 245                 250                 255

Ile Ser Ser Leu Gln Pro Glu Asp Phe Ala Thr Tyr Tyr Cys Gln Gln
             260                 265                 270

Ser Tyr Thr Thr Pro Pro Thr Phe Gly Gln Gly Thr Lys Val Glu Ile
         275                 280                 285

Lys Gly Gly Ser Ser Arg Ser Ser Ser Gly Gly Gly Gly Ser Gly
 290                 295                 300

Gly Gly Gly Glu Val Gln Leu Val Glu Ser Gly Gly Leu Val Gln
305                 310                 315                 320

Pro Gly Gly Ser Leu Arg Leu Ser Cys Ala Ala Ser Gly Phe Thr Phe
                 325                 330                 335

Thr Ser Thr Gly Ile Ser Trp Val Arg Gln Ala Pro Lys Gly Leu
             340                 345                 350

Glu Trp Val Gly Arg Ile Tyr Pro Thr Asn Gly Ser Thr Asn Tyr Ala
         355                 360                 365

Asp Ser Val Lys Gly Arg Phe Thr Ile Ser Ala Asp Thr Ser Lys Asn
 370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                 405                 410                 415

Thr Glu Tyr Val Met Asp Tyr Trp Gly Gln Gly Thr Leu Val Thr Val
             420                 425                 430
```

```
Ser Ser Gly Ser Ser Arg Ser Ser Ser Gly Gly Gly Ser
        435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gln Gly Glu Glu
                515                 520                 525

Gln Arg Phe Thr Cys Tyr Met Glu His Ser Gly Gln His Ser Thr His
                530                 535                 540

Pro Val Pro Ser Gly Lys Gly Ser His His His His His
545                 550                 555
```

<210> SEQ ID NO 35
<211> LENGTH: 558
<212> TYPE: PRT
<213> ORGANISM: Artificial Sequence
<220> FEATURE:
<223> OTHER INFORMATION: Synthetic peptide MICA-WED

<400> SEQUENCE: 35

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Glu Thr Asp Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240
```

Pro Ser Arg Phe Ser Gly Ser Gly Ser Gly Thr Asp Phe Thr Leu Thr
            245                 250                 255

Ile Ser Ser Leu Gln Pro Glu Asp Phe Ala Thr Tyr Tyr Cys Gln Gln
        260                 265                 270

Ser Tyr Thr Thr Pro Pro Thr Phe Gly Gln Gly Thr Lys Val Glu Ile
    275                 280                 285

Lys Gly Gly Ser Ser Arg Ser Ser Ser Gly Gly Gly Gly Ser Gly
290                 295                 300

Gly Gly Gly Glu Val Gln Leu Val Glu Ser Gly Gly Leu Val Gln
305                 310                 315                 320

Pro Gly Gly Ser Leu Arg Leu Ser Cys Ala Ala Ser Gly Phe Thr Phe
            325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
            355                 360                 365

Asp Ser Val Lys Gly Arg Phe Thr Ile Ser Ala Asp Thr Ser Lys Asn
    370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
            405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Gly Ser
            435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
            485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
    530                 535                 540

Pro Val Pro Ser Gly Lys Gly Ser His His His His His
545                 550                 555

<210> SEQ ID NO 36
<211> LENGTH: 1677
<212> TYPE: DNA
<213> ORGANISM: Artificial Sequence
<220> FEATURE:
<223> OTHER INFORMATION: Synthetic polynucleotide, encoding MICA alpha1-
      alpha2 variant 20

<400> SEQUENCE: 36
gagcctcaca gcctccggta taatttgact gtactctctt gggatggctc cgtgcagtcc     60
ggctttctga ctgaagttca tctcgacggt caacctttcc tgcgctgcga ccgacaaaaa    120
tgccgcgcca gccccaagg gcagtgggcc gaagatgtac tgggaaacaa gacctgggac    180
cgggagacac gagacctgac agcatgggga aaggacttgc gcatgacact cgcccatatc    240

```
aaggaccaga aggaaggatt gcactctttg caagagattc gcgtgtgtga atccacgag    300 gacaattcaa cgaggagctc ccagcacttc tattacgatg agaactctt cttgtcacag    360 aacttggaaa ccctggaatg gactatgcct cagagctccc gggcacagac tctcgctatg    420
aacgttagaa acttccttaa ggaggatgct atgcagaccg atactcacta ccgggccatg    480
cacgccgact gcctctttga actgcggaga tatctgaagt ccggcgtggt tttgagaaga    540
accgtgcccc ccatggtgca ggtgactcgc tctgaggcct ctggcggatc tggggaccgt    600
gtgacaatca cctgcagagc ctcccaggac gtctccactg ccgtggcgtg gtaccaacag    660
aagcccggga aggcacccaa actgctcatt tacagcgcat cctttctcta ctctggcgtg    720
ccgtctcgct ttagcgggtc cggcagcggt acagacttta ctctgaccat ctcctctctg    780
caaccggagg attttgcaac ctattattgc cagcaatcct acacaacccc ccccaccttt    840
ggccagggca ccaaggtgga gatcaaggga ggttctagcc gctccagcag ctctggaggt    900
ggaggctctg gcggaggagg cgaggtgcaa ctggtggagt ctggggggcgg cctggtccag    960 cccggcggaa gcttgcgcct gagctgtgcc gcctccggtt ttaccttcac cagcactgga   1020
atctcctggg tgcgccaagc tcccggcaaa gggctcgaat gggtgggccg tatctacccc   1080
accaacggaa gcaccaacta tgcagacagc gtgaaggggc gcttcactat ctccgccgac   1140
accagcaaaa acaccgcgta cctgcagatg aattctttga gggcagagga tactgccgtg   1200
tactactgcg cgaggacata cggcatttac gatctgtatg tggattacac cgaatacgtg   1260
atggactatt ggggccaggg cactctggtc acagtgtcta gcggtggcag ctcccgcagc   1320
tccagcagcg gtggtggcgg tagcggaggc ggaggcgata tccagatgac tcagagtccc   1380
tcttctctga gtgcttctgg cggaagtggg cagatcaccg tcacatgtcg cgcaagcggc   1440 tttttatcctt ggaacatcac cctgagctgg cggcaggacg gcgtcagcct gtcccatgat   1500
acccaacagt ggggagatgt gctcccggac ggtcagggaa cttaccagac ctgggttgca   1560
actcgcatct cccaggggga ggagcagcgt ttcacatgtt atatgagcca ctctggccag   1620
cacagcactc atccggtgcc gtccggaaag ggatctcatc accatcacca ccactag     1677
```

<210> SEQ ID NO 37
<211> LENGTH: 1677
<212> TYPE: DNA
<213> ORGANISM: Artificial Sequence
<220> FEATURE:
<223> OTHER INFORMATION: Synthetic polynucleotide, encoding MICA alpha1-
      alpha2 variant 25

<400> SEQUENCE: 37

```
gagcctcaca gcctccggta taatttgact gtactctctt gggatggctc cgtgcagtcc     60
ggctttctga ctgaagttca tctcgacggt caaccttcc tgcgctgcga ccgacaaaaa    120
tgccgcgcca gccccaagg gcagtgggcc gaagatgtac tgggaaacaa gacctgggac    180
cgggagacac gagacctgac aggctgggc aaggacttgc gcatgacact cgcccatatc    240
aaggaccaga aggaaggatt gcactctttg caagagattc gcgtgtgtga atccacgag    300 gacaattcaa cgaggagctc ccagcacttc tattacgatg agaactctt cttgtcacag    360 aacttggaaa ccctcgaatg gactatgcct cagagctccc gggcacagac tctcgctatg    420
aacgttagaa acttccttaa ggaggatgct atggagaccg atactcacta ccacgccatg    480
cgcgccgact gcctctctga actgcggaga tatctgaagt ccggcgtggt tttgagaaga    540
accgtgcccc ccatggtgca ggtgactcgc tctgaggcct ctggcggatc tggggaccgt    600
```

```
gtgacaatca cctgcagagc ctcccaggac gtctccactg ccgtggcgtg gtaccaacag      660
aagcccggga aggcacccaa actgctcatt tacagcgcat cctttctcta ctctggcgtg      720
ccgtctcgct ttagcgggtc cggcagcggt acagacttta ctctgaccat ctcctctctg      780
caaccggagg attttgcaac ctattattgc cagcaatcct acacaacccc cccacccttt      840
ggccagggca ccaaggtgga gatcaaggga ggttctagcc gctccagcag ctctggaggt      900
ggaggctctg gcggaggagg cgaggtgcaa ctggtggagt ctggggggcgg cctggtccag      960 cccggcggaa gcttgcgcct gagctgtgcc gcctccggtt ttaccttcac cagcactgga     1020
atctcctggg tgcgccaagc tcccggcaaa gggctcgaat gggtgggccg tatctacccc     1080
accaacggaa gcaccaacta tgcagacagc gtgaaggggc gcttcactat ctccgccgac     1140
accagcaaaa acaccgcgta cctgcagatg aattctttga gggcagagga tactgccgtg     1200
tactactgcg cgaggacata cggcatttac gatctgtatg tggattacac cgaatacgtg     1260
atggactatt ggggccaggg cactctggtc acagtgtcta gcggtggcag ctcccgcagc     1320
tccagcagcg gtggtggcgg tagcggaggc ggaggcgata tccagatgac tcagagtccc     1380
tcttctctga gtgcttctgg cggaagtggg cagatcaccg tcacatgtcg cgcaagcggc     1440
ttttatcctt ggaacatcac cctgagctgg cggcaggacg cgtcagcct gtcccatgat     1500 acccaacagt ggggagatgt gctcccggac ggtcagggaa cttaccagac ctgggttgca     1560
actcgcatct cccaggggga ggagcagcgt ttcacatgtt atatgagca ctctggccaa     1620 cacagcactc atccggtgcc gtccggaaag ggatctcatc accatcacca ccactag      1677

<210> SEQ ID NO 38
<211> LENGTH: 1677
<212> TYPE: DNA
<213> ORGANISM: Artificial Sequence
<220> FEATURE:
<223> OTHER INFORMATION: Synthetic polynucleotide, encoding MICA alpha1-
      alpha2 variant 48

<400> SEQUENCE: 38
gagccccaca gtcttcgtta taacctcacg gtgctgtcct gggacggatc tgttgtttca       60
gggtttctca ctgaggtaca tctggatggt cagcccttcc tgcgctgtga caggcagaaa      120
tgcagggcaa agccccaggg acagtgggca gaagatgtcc tggaaataa gacatgggac       180 agagagacca gagacttgga cgggtgggga aaggacctca ggatgaccct ggctcatatt      240
aaggaccaga agaaggcttg cattccctc caggagatta gggtctgtga gatccatgaa       300
gacaacagca ccaggagctc ccagcatttc tactacgatg gggagctgtt cctctcccaa      360
aacctggaga ctctggagtg gacaatgccc cagtcctcca gagctcagac cttggccatg      420
aacgtcagga cttccttgaa agaggacgcc atggcgaccg acacacacta cattgcaatg      480
cgggcagact gcctggctga actacggcga tatctgaaga gcggcgtagt cctgaggaga      540
acagtgcccc ccatggtgca ggtgactcgc tctgaggcct ctggcggatc tggggaccgt      600
gtgacaatca cctgcagagc ctcccaggac gtctccactg ccgtggcgtg gtaccaacag      660
aagcccggga aggcacccaa actgctcatt tacagcgcat cctttctcta ctctggcgtg      720
ccgtctcgct ttagcgggtc cggcagcggt acagacttta ctctgaccat ctcctctctg      780
caaccggagg attttgcaac ctattattgc cagcaatcct acacaacccc cccacccttt      840
ggccagggca ccaaggtgga gatcaaggga ggttctagcc gctccagcag ctctggaggt      900
ggaggctctg gcggaggagg cgaggtgcaa ctggtggagt ctggggggcgg cctggtccag      960
```

```
cccggcggaa gcttgcgcct gagctgtgcc gcctccggtt ttaccttcac cagcactgga    1020
atctcctggg tgcgccaagc tcccggcaaa gggctcgaat gggtgggccg tatctacccc    1080
accaacggaa gcaccaacta tgcagacagc gtgaaggggc gcttcactat ctccgccgac    1140
accagcaaaa acaccgcgta cctgcagatg aattctttga gggcagagga tactgccgtg    1200
tactactgcg cgaggacata cggcatttac gatctgtatg tggattacac cgaatacgtg    1260
atggactatt ggggccaggg cactctggtc acagtgtcta gcggtggcag ctcccgcagc    1320
tccagcagcg gtggtggcgg tagcggaggc ggaggcgata tccagatgac tcagagtccc    1380
tcttctctga gtgcttctgg cggaagtggg cagatcaccg tcacatgtcg cgcaagcggc    1440
ttttatcctt ggaacatcac cctgagctgg cggcaggacg gcgtcagcct gtcccatgat    1500
acccaacagt ggggagatgt gctcccggac ggtcagggaa cttaccagac ctgggttgca    1560
actcgcatct cccaggggga ggagcagcgt ttcacatgtt atatggagca ctctggccag    1620
cacagcactc atccggtgcc gtccggaaag ggatctcatc accatcacca ccactag       1677
```

<210> SEQ ID NO 39
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 20

<400> SEQUENCE: 39

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Ala Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Gln Thr Asp Thr His Tyr Arg Ala Met
145                 150                 155                 160

His Ala Asp Cys Leu Phe Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240
```

```
Pro Ser Arg Phe Ser Gly Ser Gly Ser Gly Thr Asp Phe Thr Leu Thr
            245                 250                 255

Ile Ser Ser Leu Gln Pro Glu Asp Phe Ala Thr Tyr Tyr Cys Gln Gln
        260                 265                 270

Ser Tyr Thr Thr Pro Pro Thr Phe Gly Gln Gly Thr Lys Val Glu Ile
            275                 280                 285

Lys Gly Gly Ser Ser Arg Ser Ser Ser Gly Gly Gly Gly Ser Gly
        290                 295                 300

Gly Gly Gly Glu Val Gln Leu Val Glu Ser Gly Gly Leu Val Gln
305                 310                 315                 320

Pro Gly Gly Ser Leu Arg Leu Ser Cys Ala Ala Ser Gly Phe Thr Phe
            325                 330                 335

Thr Ser Thr Gly Ile Ser Trp Val Arg Gln Ala Pro Gly Lys Gly Leu
            340                 345                 350

Glu Trp Val Gly Arg Ile Tyr Pro Thr Asn Gly Ser Thr Asn Tyr Ala
            355                 360                 365

Asp Ser Val Lys Gly Arg Phe Thr Ile Ser Ala Asp Thr Ser Lys Asn
        370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
            405                 410                 415

Thr Glu Tyr Val Met Asp Tyr Trp Gly Gln Gly Thr Leu Val Thr Val
            420                 425                 430

Ser Ser Gly Gly Ser Ser Arg Ser Ser Ser Gly Gly Gly Gly Ser
            435                 440                 445

Gly Gly Gly Gly Asp Ile Gln Met Thr Gln Ser Pro Ser Ser Leu Ser
        450                 455                 460

Ala Ser Gly Gly Ser Gly Gln Ile Thr Val Thr Cys Arg Ala Ser Gly
465                 470                 475                 480

Phe Tyr Pro Trp Asn Ile Thr Leu Ser Trp Arg Gln Asp Gly Val Ser
            485                 490                 495

Leu Ser His Asp Thr Gln Gln Trp Gly Asp Val Leu Pro Asp Gly Gln
            500                 505                 510

Gly Thr Tyr Gln Thr Trp Val Ala Thr Arg Ile Ser Gln Gly Glu Glu
            515                 520                 525

Gln Arg Phe Thr Cys Tyr Met Glu His Ser Gly Gln His Ser Thr His
            530                 535                 540

Pro Val Pro Ser Gly Lys Gly Ser His His His His His
545                 550                 555

<210> SEQ ID NO 40
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 25

<400> SEQUENCE: 40

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45
```

```
Trp Ala Glu Asp Val Leu Gly Asn Lys Thr Trp Asp Arg Glu Thr Arg
             50                  55                  60

Asp Leu Thr Gly Trp Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                     85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Leu Glu Trp Thr
                115                 120                 125

Met Pro Gln Ser Ser Arg Ala Gln Thr Leu Ala Met Asn Val Arg Asn
130                 135                 140

Phe Leu Lys Glu Asp Ala Met Glu Thr Asp Thr His Tyr His Ala Met
145                 150                 155                 160

Arg Ala Asp Cys Leu Ser Glu Leu Arg Arg Tyr Leu Lys Ser Gly Val
                165                 170                 175

Val Leu Arg Arg Thr Val Pro Pro Met Val Gln Val Thr Arg Ser Glu
                180                 185                 190

Ala Ser Gly Gly Ser Gly Asp Arg Val Thr Ile Thr Cys Arg Ala Ser
                195                 200                 205

Gln Asp Val Ser Thr Ala Val Ala Trp Tyr Gln Gln Lys Pro Gly Lys
                210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
                260                 265                 270

Ser Tyr Thr Thr Pro Pro Thr Phe Gly Gln Gly Thr Lys Val Glu Ile
                275                 280                 285

Lys Gly Gly Ser Ser Arg Ser Ser Ser Ser Gly Gly Gly Gly Ser Gly
                290                 295                 300

Gly Gly Gly Glu Val Gln Leu Val Glu Ser Gly Gly Gly Leu Val Gln
305                 310                 315                 320

Pro Gly Gly Ser Leu Arg Leu Ser Cys Ala Ala Ser Gly Phe Thr Phe
                325                 330                 335

Thr Ser Thr Gly Ile Ser Trp Val Arg Gln Ala Pro Gly Lys Gly Leu
                340                 345                 350

Glu Trp Val Gly Arg Ile Tyr Pro Thr Asn Gly Ser Thr Asn Tyr Ala
                355                 360                 365

Asp Ser Val Lys Gly Arg Phe Thr Ile Ser Ala Asp Thr Ser Lys Asn
                370                 375                 380

Thr Ala Tyr Leu Gln Met Asn Ser Leu Arg Ala Glu Asp Thr Ala Val
385                 390                 395                 400

Tyr Tyr Cys Ala Arg Thr Tyr Gly Ile Tyr Asp Leu Tyr Val Asp Tyr
                405                 410                 415

Thr Glu Tyr Val Met Asp Tyr Trp Gly Gln Gly Thr Leu Val Thr Val
                420                 425                 430

Ser Ser Gly Gly Ser Ser Arg Ser Ser Ser Gly Gly Gly Gly Ser
                435                 440                 445

Gly Gly Gly Gly Asp Ile Gln Met Thr Gln Ser Pro Ser Ser Leu Ser
450                 455                 460

Ala Ser Gly Gly Ser Gly Gln Ile Thr Val Thr Cys Arg Ala Ser Gly
```

```
            465                 470                 475                 480

Phe Tyr Pro Trp Asn Ile Thr Leu Ser Trp Arg Gln Asp Gly Val Ser
                485                 490                 495

Leu Ser His Asp Thr Gln Gln Trp Gly Asp Val Leu Pro Asp Gly Gln
                500                 505                 510

Gly Thr Tyr Gln Thr Trp Val Ala Thr Arg Ile Ser Gln Gly Glu Glu
                515                 520                 525

Gln Arg Phe Thr Cys Tyr Met Glu His Ser Gly Gln His Ser Thr His
                530                 535                 540

Pro Val Pro Ser Gly Lys Gly Ser His His His His His His
545                 550                 555

<210> SEQ ID NO 41
<211> LENGTH: 558
<212> TYPE: PRT
<213> ORGANISM: Artificial Sequence
<220> FEATURE:
<223> OTHER INFORMATION: Synthetic peptide MICA alpha1-alpha2 variant 48

<400> SEQUENCE: 41

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
                20                  25                  30

Phe Leu Arg Cys Asp Arg Gln Lys Cys Arg Ala Lys Pro Gln Gly Gln
                35                  40                  45

Trp Ala Glu Asp Val Leu Gly Asn Lys Thr Trp Asp Arg Glu Thr Arg
        50                  55                  60

Asp Leu Thr Gly Trp Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Leu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Ala Thr Asp Thr His Tyr Ile Ala Met
145                 150                 155                 160

Arg Ala Asp Cys Leu Ala Glu Leu Arg Arg Tyr Leu Lys Ser Gly Val
                165                 170                 175

Val Leu Arg Arg Thr Val Pro Pro Met Val Gln Val Thr Arg Ser Glu
            180                 185                 190

Ala Ser Gly Gly Ser Gly Asp Arg Val Thr Ile Thr Cys Arg Ala Ser
        195                 200                 205

Gln Asp Val Ser Thr Ala Val Ala Trp Tyr Gln Gln Lys Pro Gly Lys
    210                 215                 220

Ala Pro Lys Leu Leu Ile Tyr Ser Ala Ser Phe Leu Tyr Ser Gly Val
225                 230                 235                 240

Pro Ser Arg Phe Ser Gly Ser Gly Ser Gly Thr Asp Phe Thr Leu Thr
                245                 250                 255

Ile Ser Ser Leu Gln Pro Glu Asp Phe Ala Thr Tyr Tyr Cys Gln Gln
            260                 265                 270

Ser Tyr Thr Thr Pro Pro Thr Phe Gly Gln Gly Thr Lys Val Glu Ile
```

```
        275                 280                 285
Lys Gly Gly Ser Ser Arg Ser Ser Ser Gly Gly Gly Ser Gly
    290                 295                 300
Gly Gly Gly Glu Val Gln Leu Val Glu Ser Gly Gly Leu Val Gln
305                 310                 315                 320
Pro Gly Gly Ser Leu Arg Leu Ser Cys Ala Ala Ser Gly Phe Thr Phe
                325                 330                 335
Thr Ser Thr Gly Ile Ser Trp Val Arg Gln Ala Pro Gly Lys Gly Leu
            340                 345                 350
Glu Trp Val Gly Arg Ile Tyr Pro Thr Asn Gly Ser Thr Asn Tyr Ala
        355                 360                 365
Asp Ser Val Lys Gly Arg Phe Thr Ile Ser Ala Asp Thr Ser Lys Asn
    370                 375                 380
Thr Ala Tyr Leu Gln Met Asn Ser Leu Arg Ala Glu Asp Thr Ala Val
385                 390                 395                 400
Tyr Tyr Cys Ala Arg Thr Tyr Gly Ile Tyr Asp Leu Tyr Val Asp Tyr
                405                 410                 415
Thr Glu Tyr Val Met Asp Tyr Trp Gly Gln Gly Thr Leu Val Thr Val
            420                 425                 430
Ser Ser Gly Gly Ser Ser Arg Ser Ser Ser Gly Gly Gly Ser
        435                 440                 445
Gly Gly Gly Gly Asp Ile Gln Met Thr Gln Ser Pro Ser Ser Leu Ser
    450                 455                 460
Ala Ser Gly Gly Ser Gly Gln Ile Thr Val Thr Cys Arg Ala Ser Gly
465                 470                 475                 480
Phe Tyr Pro Trp Asn Ile Thr Leu Ser Trp Arg Gln Asp Gly Val Ser
                485                 490                 495
Leu Ser His Asp Thr Gln Gln Trp Gly Asp Val Leu Pro Asp Gly Gln
            500                 505                 510
Gly Thr Tyr Gln Thr Trp Val Ala Thr Arg Ile Ser Gln Gly Glu Glu
        515                 520                 525
Gln Arg Phe Thr Cys Tyr Met Glu His Ser Gly Gln His Ser Thr His
    530                 535                 540
Pro Val Pro Ser Gly Lys Gly Ser His His His His His
545                 550                 555
```

<210> SEQ ID NO 42
<211> LENGTH: 1974
<212> TYPE: DNA
<213> ORGANISM: Artificial Sequence
<220> FEATURE:
<223> OTHER INFORMATION: Synthetic polynucleotide, encoding HC_WT

<400> SEQUENCE: 42

```
atgcggccaa ttgtcctcgt gctccttttc gccacctccg ccctcgctga ggtgcaactg      60
gtggagtctg ggggcggcct ggtccagccc ggcggaagct tgcgcctgag ctgtgccgcc     120
tccggtttta ccttcaccag cactggaatc tcctgggtgc gccagctcc cggcaaaggg      180 ctcgaatggg tgggccgtat ctaccccacc aacggaagca ccaactatgc agacagcgtg     240
aaggggcgct tcactatctc cgccgacacc agcaaaaaca ccgcgtacct gcagatgaac     300
tctttgaggg cagaggatac tgccgtgtac tactgcgcga ggacatacgg catttacgat     360
ctgtatgtgg attacaccga atacgtgatg gactattggg gccagggcac tctggtcaca     420
gtgtctagcg cgtcgaccaa gggcccgtca gtgttcccgc tggccccgtc atccaagtcc     480
```

| | |
|---|---|
| acgtctgggg gcacagcagc cctgggatgc ttggtcaagg actacttccc cgagcccgtg | 540 |
| actgtgtcct ggaactccgg agcactgacc tccggagtgc acacctttcc cgcggtgctg | 600 |
| cagtcctccg gactgtactc cctgtcgtcg gtcgtgaccg tgccgagctc ctcgctcgga | 660 |
| acccagacct acatctgcaa cgtgaaccac aagccctcga acaccaaagt ggacaagaag | 720 |
| gtcgagccca aaagctgcga caagactcac acttgtccgc cgtgccccgc ccccgaactg | 780 |
| ctgggtggcc cctccgtgtt cctgttcccg cctaagccta aggacaccct tatgatcagc | 840 |
| cgcacccctg aagtgacctg tgtcgtcgtg gatgtgtcac acgaggaccc ggaggtcaag | 900 |
| ttcaattggt acgtggacgg cgtggaagtg cataacgcaa agaccaagcc tcgggaggaa | 960 |
| cagtacaact cgacctaccg cgtggtgtca gtcctgactg tgctgcacca ggactggctg | 1020 |
| aacgggaagg agtacaagtg caaagtgtcg aacaaggccc tgccggctcc aattgaaaag | 1080 |
| accatcagca aggccaaggg ccagccaagg gaaccacagg tgtacaccct ccctccttcc | 1140 |
| cgggacgagc tgaccaaaaa ccaagtgtcc ctgacttgcc ttgtgaaggg gttctaccct | 1200 |
| tctgacattg ccgtcgaatg ggaatcgaac ggacagcctg aaaacaacta taagactacc | 1260 |
| ccgcccgtgc tggattccga cggaagcttc ttcctgtact ccaagctgac cgtggacaag | 1320 |
| tcgagatggc agcaggaaaa tgtgttcagc tgctccgtga tgcatgaggc gctgcacaac | 1380 |
| cactacaccc cgaagtcact gagcctctcc ccggaggag gtggcagcga gcctcacagc | 1440 |
| ctccggtata atttgactgt actctcttgg gatggctccg tgcagtccgg ctttctgact | 1500 |
| gaagttcatc tcgacggtca accttttcctg cgctgcgacc gacaaaaatg ccgcgccaag | 1560 |
| ccccaagggg agtgggccga agatgtactg ggaaacaaga cctgggaccg ggagacacga | 1620 |
| gacctgacag gcaacggcaa ggacttgcgc atgacactcg cccatatcaa ggaccagaag | 1680 |
| gaaggattgc actcttttgca agagattcgc gtgtgtgaaa tccacgagga caattcaacg | 1740 |
| aggagctccc agcacttcta ttacgatgga gaactcttct tgtcacagaa cttggaaacc | 1800 |
| aaggaatgga ctatgcctca gagctctcgg gcacagactc tcgctatgaa cgttagaaac | 1860 |
| ttccttaagg aggatgctat gaagaccaaa actcactacc acgccatgca cgccgactgc | 1920 |
| ctccaggaac tgcggagata tctgaagtcc ggcgtggttt tgagaagaac ctag | 1974 |

<210> SEQ ID NO 43
<211> LENGTH: 1974
<212> TYPE: DNA
<213> ORGANISM: Artificial Sequence
<220> FEATURE:
<223> OTHER INFORMATION: Synthetic polynucleotide, encoding HC_WED

<400> SEQUENCE: 43

| | |
|---|---|
| atgcggccaa ttgtcctcgt gctccttttc gccacctccg ccctcgctga ggtgcaactg | 60 |
| gtggagtctg ggggcggcct ggtccagccc ggcggaagct gcgcctgag ctgtgccgcc | 120 |
| tccggtttta ccttcaccag cactggaatc tcctgggtgc gccaagctcc cggcaaaggg | 180 |
| ctcgaatggg tgggccgtat ctaccccacc aacggaagca ccaactatgc agacagcgtg | 240 |
| aaggggcgct tcactatctc cgccgacacc agcaaaaaca ccgcgtacct gcagatgaac | 300 |
| tctttgaggg cagaggatac tgccgtgtac tactgcgcga ggacatacgg catttacgat | 360 |
| ctgtatgtgg attacaccga atacgtgatg gactattggg gccagggcac tctggtcaca | 420 |
| gtgtctagcg cgtcgaccaa gggcccgtca gtgttcccgc tggccccgtc atccaagtcc | 480 |
| acgtctgggg gcacagcagc cctgggatgc ttggtcaagg actacttccc cgagcccgtg | 540 |
| actgtgtcct ggaactccgg agcactgacc tccggagtgc acacctttcc cgcggtgctg | 600 |

```
cagtcctccg gactgtactc cctgtcgtcg gtcgtgaccg tgccgagctc ctcgctcgga    660
acccagacct acatctgcaa cgtgaaccac aagcccctcga acaccaaagt ggacaagaag    720
gtcgagccca aaagctgcga caagactcac acttgtccgc cgtgccccgc ccccgaactg    780
ctgggtggcc cctccgtgtt cctgttcccg cctaagccta aggacaccct tatgatcagc    840 cgcaccctg  aagtgacctg tgtcgtcgtg gatgtgtcac acgaggaccc ggaggtcaag    900
ttcaattggt acgtggacgg cgtggaagtg cataacgcaa agaccaagcc tcgggaggaa    960
cagtacaact cgacctaccg cgtggtgtca gtcctgactg tgctgcacca ggactggctg   1020
aacgggaagg agtacaagtg caaagtgtcg aacaaggccc tgccggctcc aattgaaaag   1080
accatcagca aggccaaggg ccagccaagg gaaccacagg tgtacaccct ccctccttcc   1140
cgggacgagc tgaccaaaaa ccaagtgtcc ctgacttgcc ttgtgaaggg gttctaccct   1200
tctgacattg ccgtcgaatg ggaatcgaac ggacagcctg aaaacaacta taagactacc   1260
ccgcccgtgc tggattccga cggaagcttc ttcctgtact ccaagctgac cgtggacaag   1320
tcgagatggc agcagggaaa tgtgttcagc tgctccgtga tgcatgaggc gctgcacaac   1380
cactacaccc agaagtcact gagcctctcc cccggaggag gtggcagcga gcctcacagc   1440
ctccggtata atttgactgt actctcttgg gatggctccg tgcagtccgg cttctctgact   1500 gaagttcatc tcgacggtca accttttcctg cgctgcgacc gacaaaaatg ccgcgccaag   1560
ccccaagggc agtgggccga agatgtactg ggaaacaaga cctgggaccg ggagacacga   1620
gacctgacag gctggggcaa ggacttgcgc atgacactcg cccatatcaa ggaccagaag   1680
gaaggattgc actctttgca agagattcgc gtgtgtgaaa tccacgagga caattcaacg   1740
aggagctccc agcacttcta ttacgatgga gaactcttct tgtcacagaa cttggaaacc   1800
aaggaatgga ctatgcctca gagctctcgg gcacagactc tcgctatgaa cgttagaaac   1860
ttccttaagg aggatgctat ggagaccgat actcactacc acgccatgca cgccgactgc   1920
ctccaggaac tgcggagata tctgaagtcc ggcgtggttt tgagaagaac ctag         1974
```

<210> SEQ ID NO 44
<211> LENGTH: 1974
<212> TYPE: DNA
<213> ORGANISM: Artificial Sequence
<220> FEATURE:
<223> OTHER INFORMATION: Synthetic polynucleotide, encoding HC_25

<400> SEQUENCE: 44

```
atgcggccaa ttgtcctcgt gctccttttc gccacctccg ccctcgctga ggtgcaactg     60
gtggagtctg ggggcggcct ggtccagccc ggcggaagct tgcgcctgag ctgtgccgcc    120
tccggtttta ccttcaccag cactggaatc tcctgggtgc gccaagctcc cggcaaaggg    180
ctcgaatggg tgggccgtat ctaccccacc aacggaagca ccaactatgc agacagcgtg    240 aagggcgct  tcactatctc cgccgacacc agcaaaaaca ccgcgtacct gcagatgaac    300
tctttgaggg cagaggatac tgccgtgtac tactgcgcga ggacatacgg catttacgat    360
ctgtatgtgg attacaccga atacgtgatg gactattggg gccagggcac tctggtcaca    420
gtgtctagcg cgtcgaccaa gggcccgtca gtgttcccgc tggccccgtc atccaagtcc    480
acgtctgggg gcacagcagc cctgggatgc ttggtcaagg actacttccc cgagcccgtg    540
actgtgtcct ggaactccgg agcactgacc tccggagtgc acacctttcc cgcggtgctg    600
cagtcctccg gactgtactc cctgtcgtcg gtcgtgaccg tgccgagctc ctcgctcgga    660
```

```
acccagacct acatctgcaa cgtgaaccac aagccctcga acaccaaagt ggacaagaag        720
gtcgagccca aaagctgcga caagactcac acttgtccgc cgtgcccgc ccccgaactg         780 ctgggtggcc cctccgtgtt cctgttccg cctaagccta aggacaccct tatgatcagc         840 cgcaccctg aagtgacctg tgtcgtcgtg gatgtgtcac acgaggaccc ggaggtcaag         900
ttcaattggt acgtggacgg cgtggaagtg cataacgcaa agaccaagcc tcggaggaa         960 cagtacaact cgacctaccg cgtggtgtca gtcctgactg tgctgcacca ggactggctg       1020
aacgggaagg agtacaagtg caaagtgtcg aacaaggccc tgccggctcc aattgaaaag       1080
accatcagca aggccaaggg ccagccaagg gaaccacagg tgtacaccct ccctccttcc       1140
cgggacgagc tgaccaaaaa ccaagtgtcc ctgacttgcc ttgtgaaggg gttctaccct       1200
tctgacattg ccgtcgaatg ggaatcgaac ggacagcctg aaaacaacta taagactacc       1260
ccgcccgtgc tggattccga cggaagcttc ttcctgtact ccaagctgac cgtggacaag       1320
tcgagatggc agcagggaaa tgtgttcagc tgctccgtga tgcatgaggc gctgcacaac       1380
cactaccccc agaagtcact gagcctctcc cccggaggag gtggcagcga gcctcacagc       1440
ctccggtata atttgactgt actctcttgg gatggctccg tgcagtccgg ctttctgact       1500
gaagttcatc tcgacggtca acctttcctg cgctgcgacc gacaaaaatg ccgcgccaag       1560
ccccaagggc agtgggccga agatgtactg ggaaacaaga cctgggaccg ggagacacga       1620
gacctgacag gctggggcaa ggacttgcgc atgacactcg cccatatcaa ggaccagaag       1680
gaaggattgc actctttgca agagattcgc gtgtgtgaaa tccacgagga caattcaacg       1740
aggagctccc agcacttcta ttacgatgga gaactcttct tgtcacagaa cttggaaacc       1800
ctcgaatgga ctatgcctca gagctctcgg gcacagactc tcgctatgaa cgttagaaac       1860
ttccttaagg aggatgctat ggagaccgat actcactacc acgccatgcg cgccgactgc       1920
ctctctgaac tgcggagata tctgaagtcc ggcgtggttt tgagaagaac ctag            1974

<210> SEQ ID NO 45
<211> LENGTH: 1974
<212> TYPE: DNA
<213> ORGANISM: Artificial Sequence
<220> FEATURE:
<223> OTHER INFORMATION: Synthetic polynucleotide, encoding HC_48

<400> SEQUENCE: 45
atgcggccaa ttgtcctcgt gctccttttc gccacctccg ccctcgctga ggtgcaactg         60
gtggagtctg ggggcggcct ggtccagccc ggcggaagct tgcgcctgag ctgtgccgcc        120
tccggtttta ccttcaccag cactggaatc tcctgggtgc gccaagctcc cggcaaaggg        180
ctcgaatggg tggccgtat ctaccccacc aacggaagca ccaactatgc agacagcgtg         240
aaggggcgct tcactatctc cgccgacacc agcaaaaaca ccgcgtacct gcagatgaac        300
tctttgaggg cagaggatac tgccgtgtac tactgcgcga ggacatacgg catttacgat        360
ctgtatgtgg attacaccga atacgtgatg gactattggg gccagggcac tctggtcaca        420
gtgtctagcg cgtcgaccaa gggcccgtca gtgttcccgc tggccccgtc atccaagtcc        480
acgtctgggg gcacagcagc cctgggatgc ttggtcaagg actacttccc cgagccgtg         540 actgtgtcct ggaactccgg agcactgacc tccggagtgc acacctttcc cgcggtgctg        600
cagtcctccg gactgtactc cctgtcgtcg gtcgtgaccg tgccgagctc ctcgctcgga        660
acccagacct acatctgcaa cgtgaaccac aagccctcga acaccaaagt ggacaagaag        720
gtcgagccca aaagctgcga caagactcac acttgtccgc cgtgcccgc ccccgaactg         780
```

```
ctgggtggcc cctccgtgtt cctgttcccg cctaagccta aggacaccct tatgatcagc    840
cgcacccctg aagtgacctg tgtcgtcgtg gatgtgtcac acgaggaccc ggaggtcaag    900
ttcaattggt acgtggacgg cgtggaagtg cataacgcaa agaccaagcc tcggaggaa     960 cagtacaact cgacctaccg cgtggtgtca gtcctgactg tgctgcacca ggactggctg   1020
aacgggaagg agtacaagtg caaagtgtcg aacaaggccc tgccggctcc aattgaaaag   1080
accatcagca aggccaaggg ccagccaagg gaaccacagg tgtacaccct ccctccttcc   1140
cgggacgagc tgaccaaaaa ccaagtgtcc ctgacttgcc ttgtgaaggg gttctaccct   1200
tctgacattg ccgtcgaatg ggaatcgaac ggacagcctg aaaacaacta taagactacc   1260
ccgcccgtgc tggattccga cggaagcttc ttcctgtact ccaagctgac cgtggacaag   1320
tcgagatggc agcagggaaa tgtgttcagc tgctccgtga tgcatgaggc gctgcacaac   1380
cactacaccc agaagtcact gagcctctcc cccggaggag gtggcagcga gcctcacagc   1440
ctccggtata atttgactgt actctcttgg gatggctccg tgcagtccgg ctttctgact   1500
gaagttcatc tcgacggtca acctttcctg cgctgcgacc gacaaaaatg ccgcgccaag   1560
ccccaagggc agtgggccga agatgtactg gaaacaagga cctgggaccg ggagacacga   1620
gacctgacag gctggggcaa ggacttgcgc atgacactcg cccatatcaa ggaccagaag   1680
gaaggattgc actctttgca agagattcgc gtgtgtgaaa tccacgagga caattcaacg   1740
aggagctccc agcacttcta ttacgatgga gaactcttct tgtcacagaa cttggaaacc   1800
ctcgaatgga ctatgcctca gagctctcgg gcacagactc tcgctatgaa cgttagaaac   1860
ttccttaagg aggatgctat ggctaccgat actcactaca tcgccatgcg cgccgactgc   1920
ctcgctgaac tgcggagata tctgaagtcc ggcgtggttt tgagaagaac ctag          1974
```

<210> SEQ ID NO 46  
<211> LENGTH: 1269  
<212> TYPE: DNA  
<213> ORGANISM: Artificial Sequence  
<220> FEATURE:  
<223> OTHER INFORMATION: Synthetic polynucleotide, encoding LC_WT

<400> SEQUENCE: 46

```
atgagaccta tcgttcttgt actccttttc gctacctccg ccctcgccga cattcagatg     60
actcagtctc ccagttctct tagtgcctct gtgggagatc gcgtaactat cacttgcaga    120
gcttctcagg acgtgtccac cgcggttgct tggtaccagc aaaagcctgg aaaggcgccg    180
aagctgctga tctactccgc ctcattcttg tactcaggag tgcccagtcg atttagtggt    240
agcggttctg gtactgattt cacccttacc atcagcagtc tccagcccga ggatttcgct    300
acttattact gccagcagtc atacaccact cctcccactt tcggccaagg taccaaggtc    360
gagattaaac ggaccgtggc cgccccgagc gtgttcattt tccctccctc gacgagcag    420 ttgaaatcgg gcaccgctag cgtggtctgc cttctcaaca atttctatcc cgggaagcc    480 aaagtgcagt ggaaggtcga caacgcgctc caatccggga actcacagga atccgtgact    540
gagcaggatt ccaaggactc gacctactcc ctgtcatcca cgctgaccct gagcaaggca    600
gactacgaga agcacaaggt ctacgcctgc gaagtgacac accagggact gtccagcccc    660
gtgaccaaga gcttcaacag aggagaatgc gcacctacct caagctctgg aggaggtggc    720
agcgagcctc acagcctccg gtataatttg actgtactct cttgggatgg ctccgtgcag    780
tccggctttc tgactgaagt tcatctcgac ggtcaacctt tcctgcgctg cgaccgacaa    840
```

```
aaatgccgcg ccaagcccca agggcagtgg gccgaagatg tactgggaaa caagacctgg    900
gaccgggaga cacgagacct gacaggcaac ggcaaggact tgcgcatgac actcgcccat    960
atcaaggacc agaaggaagg attgcactct ttgcaagaga ttcgcgtgtg tgaaatccac   1020
gaggacaatt caacgaggag ctcccagcac ttctattacg atggagaact cttcttgtca   1080
cagaacttgg aaaccaagga atggactatg cctcagagct ctcgggcaca gactctcgct   1140
atgaacgtta gaaacttcct taaggaggat gctatgaaga ccaaaactca ctaccacgcc   1200
atgcacgccg actgcctcca ggaactgcgg agatatctga agtccggcgt ggttttgaga   1260
agaacctaa                                                           1269
```

<210> SEQ ID NO 47
<211> LENGTH: 1269
<212> TYPE: DNA
<213> ORGANISM: Artificial Sequence
<220> FEATURE:
<223> OTHER INFORMATION: Synthetic polynucleotide, encoding LC_WED

<400> SEQUENCE: 47

```
atgagaccta tcgttcttgt actccttttc gctacctccg ccctcgccga cattcagatg     60
actcagtctc ccagttctct tagtgcctct gtgggagatc gcgtaactat cacttgcaga    120
gcttctcagg acgtgtccac cgcggttgct tggtaccagc aaaagcctgg aaaggcgccg    180
aagctgctga tctactccgc tcattcttg tactcaggag tgcccagtcg atttagtggt    240
agcggttctg gtactgattt caccccttacc atcagcagtc tccagcccga ggatttcgct    300
acttattact gccagcagtc atacaccact cctcccactt tcggccaagg taccaaggtc    360
gagattaaac ggaccgtggc cgccccgagc gtgttcattt tccctccctc cgacgagcag    420
ttgaaatcgg gcaccgctag cgtggtctgc cttctcaaca atttctatcc acgggaagcc    480
aaagtgcagt ggaaggtcga caacgcgctc caatccggga actcacagga atccgtgact    540
gagcaggatt ccaaggactc gacctactcc ctgtcatcca cgctgaccct gagcaaggca    600
gactacgaga agcacaaggt ctacgcctgc gaagtgacac accagggact gtccagcccc    660
gtgaccaaga gcttcaacag aggagaatgc gcacctacct caagctctgg aggaggtggc    720
agcgagcctc acagcctccg gtataatttg actgtactct cttgggatgg ctccgtgcag    780
tccggctttc tgactgaagt tcatctcgac ggtcaacctt tcctgcgctg cgaccgacaa    840
aaatgccgcg ccaagcccca agggcagtgg gccgaagatg tactgggaaa caagacctgg    900
gaccgggaga cacgagacct gacaggctgg ggcaaggact tgcgcatgac actcgcccat    960
atcaaggacc agaaggaagg attgcactct ttgcaagaga ttcgcgtgtg tgaaatccac   1020
gaggacaatt caacgaggag ctcccagcac ttctattacg atggagaact cttcttgtca   1080
cagaacttgg aaaccaagga atggactatg cctcagagct ctcgggcaca gactctcgct   1140
atgaacgtta gaaacttcct taaggaggat gctatgaaga ccgatactca ctaccacgcc   1200
atgcacgccg actgcctcca ggaactgcgg agatatctga agtccggcgt ggttttgaga   1260
agaacctaa                                                           1269
```

<210> SEQ ID NO 48
<211> LENGTH: 1269
<212> TYPE: DNA
<213> ORGANISM: Artificial Sequence
<220> FEATURE:
<223> OTHER INFORMATION: Synthetic polynucleotide, encoding LC_25

<400> SEQUENCE: 48

```
atgagaccta tcgttcttgt actccttttc gctacctccg ccctcgccga cattcagatg    60
actcagtctc ccagttctct tagtgcctct gtgggagatc gcgtaactat cacttgcaga   120
gcttctcagg acgtgtccac cgcggttgct tggtaccagc aaaagcctgg aaaggcgccg   180
aagctgctga tctactccgc ctcattcttg tactcaggag tgcccagtcg atttagtggt   240
agcggttctg gtactgattt caccettacc atcagcagtc tccagcccga ggatttcgct   300
acttattact gccagcagtc atacaccact cctcccactt tcggccaagg taccaaggtc   360
gagattaaac ggaccgtggc cgccccgagc gtgttcattt tccctccctc cgacgagcag   420
ttgaaatcgg gcaccgctag cgtggtctgc cttctcaaca atttctatcc acgggaagcc   480
aaagtgcagt ggaaggtcga caacgcgctc caatccggga actcacagga atccgtgact   540
gagcaggatt ccaaggactc gacctactcc ctgtcatcca cgctgaccct gagcaaggca   600
gactacgaga agcacaaggt ctacgcctgc gaagtgacac caggggact gtccagcccc    660
gtgaccaaga gcttcaacag aggagaatgc gcacctacct caagctctgg aggaggtggc   720
agcgagcctc acagcctccg gtataatttg actgtactct cttgggatgg ctccgtgcag   780
tccggctttc tgactgaagt tcatctcgac ggtcaacctt cctgcgctg cgaccgacaa     840
aaatgccgcg ccaagcccca agggcagtgg gccgaagatg tactgggaaa caagacctgg   900
gaccgggaga cacgagacct gacaggctgg ggcaaggact gcgcatgac actcgcccat     960
atcaaggacc agaaggaagg attgcactct ttgcaagaga ttcgcgtgtg tgaaatccac  1020
gaggacaatt caacgaggag ctcccagcac ttctattacg atggagaact cttcttgtca  1080
cagaacttgg aaaccctcga atggactatg cctcagagct ctcgggcaca gactctcgct  1140
atgaacgtta gaaacttcct taaggaggat gctatggaaa ccgatactca ctaccatgcc  1200
atgagagccg actgcctctc tgaactgcgg agatatctga agtccggagt ggttttgaga  1260
agaacttaa                                                            1269
```

<210> SEQ ID NO 49
<211> LENGTH: 1269
<212> TYPE: DNA
<213> ORGANISM: Artificial Sequence
<220> FEATURE:
<223> OTHER INFORMATION: Synthetic polynucleotide, encoding LC_48

<400> SEQUENCE: 49

```
atgagaccta tcgttcttgt actccttttc gctacctccg ccctcgccga cattcagatg    60
actcagtctc ccagttctct tagtgcctct gtgggagatc gcgtaactat cacttgcaga   120
gcttctcagg acgtgtccac cgcggttgct tggtaccagc aaaagcctgg aaaggcgccg   180
aagctgctga tctactccgc ctcattcttg tactcaggag tgcccagtcg atttagtggt   240
agcggttctg gtactgattt caccettacc atcagcagtc tccagcccga ggatttcgct   300
acttattact gccagcagtc atacaccact cctcccactt tcggccaagg taccaaggtc   360
gagattaaac ggaccgtggc cgccccgagc gtgttcattt tccctccctc cgacgagcag   420
ttgaaatcgg gcaccgctag cgtggtctgc cttctcaaca atttctatcc acgggaagcc   480
aaagtgcagt ggaaggtcga caacgcgctc caatccggga actcacagga atccgtgact   540
gagcaggatt ccaaggactc gacctactcc ctgtcatcca cgctgaccct gagcaaggca   600
gactacgaga agcacaaggt ctacgcctgc gaagtgacac caggggact gtccagcccc    660
gtgaccaaga gcttcaacag aggagaatgc gcacctacct caagctctgg aggaggtggc   720
```

| | |
|---|---|
| agcgagcctc acagcctccg gtataatttg actgtactct cttgggatgg ctccgtgcag | 780 |
| tccggctttc tgactgaagt tcatctcgac ggtcaacctt tcctgcgctg cgaccgacaa | 840 |
| aaatgccgcg ccaagcccca agggcagtgg gccgaagatg tactgggaaa caagacctgg | 900 |
| gaccgggaga cacgagacct gacaggctgg ggcaaggact tgcgcatgac actcgcccat | 960 |
| atcaaggacc agaaggaagg attgcactct ttgcaagaga ttcgcgtgtg tgaaatccac | 1020 |
| gaggacaatt caacgaggag ctcccagcac ttctattacg atggagaact cttcttgtca | 1080 |
| cagaacttgg aaaccctcga atggactatg cctcagagct ctcgggcaca gactctcgct | 1140 |
| atgaacgtta gaaacttcct taaggaggat gctatggcta ccgatactca ctacatcgcc | 1200 |
| atgcgcgccg actgcctcgc tgaactgcgg agatatctga agtccggcgt ggttttgaga | 1260 |
| agaacctaa | 1269 |

<210> SEQ ID NO 50
<211> LENGTH: 657
<212> TYPE: PRT
<213> ORGANISM: Artificial Sequence
<220> FEATURE:
<223> OTHER INFORMATION: Synthetic peptide HC_WT

<400> SEQUENCE: 50

Met Arg Pro Ile Val Leu Val Leu Leu Phe Ala Thr Ser Ala Leu Ala
1               5                   10                  15

Glu Val Gln Leu Val Glu Ser Gly Gly Gly Leu Val Gln Pro Gly Gly
            20                  25                  30

Ser Leu Arg Leu Ser Cys Ala Ala Ser Gly Phe Thr Phe Thr Ser Thr
        35                  40                  45

Gly Ile Ser Trp Val Arg Gln Ala Pro Gly Lys Gly Leu Glu Trp Val
    50                  55                  60

Gly Arg Ile Tyr Pro Thr Asn Gly Ser Thr Asn Tyr Ala Asp Ser Val
65                  70                  75                  80

Lys Gly Arg Phe Thr Ile Ser Ala Asp Thr Ser Lys Asn Thr Ala Tyr
                85                  90                  95

Leu Gln Met Asn Ser Leu Arg Ala Glu Asp Thr Ala Val Tyr Tyr Cys
            100                 105                 110

Ala Arg Thr Tyr Gly Ile Tyr Asp Leu Tyr Val Asp Tyr Thr Glu Tyr
        115                 120                 125

Val Met Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys

```
              260                 265                 270
Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
            450                 455                 460

Lys Ser Leu Ser Leu Ser Pro Gly Gly Gly Gly Ser Glu Pro His Ser
465                 470                 475                 480

Leu Arg Tyr Asn Leu Thr Val Leu Ser Trp Asp Gly Ser Val Gln Ser
                485                 490                 495

Gly Phe Leu Thr Glu Val His Leu Asp Gly Gln Pro Phe Leu Arg Cys
            500                 505                 510

Asp Arg Gln Lys Cys Arg Ala Lys Pro Gln Gly Gln Trp Ala Glu Asp
            515                 520                 525

Val Leu Gly Asn Lys Thr Trp Asp Arg Glu Thr Arg Asp Leu Thr Gly
            530                 535                 540

Asn Gly Lys Asp Leu Arg Met Thr Leu Ala His Ile Lys Asp Gln Lys
545                 550                 555                 560

Glu Gly Leu His Ser Leu Gln Glu Ile Arg Val Cys Glu Ile His Glu
                565                 570                 575

Asp Asn Ser Thr Arg Ser Ser Gln His Phe Tyr Tyr Asp Gly Glu Leu
            580                 585                 590

Phe Leu Ser Gln Asn Leu Glu Thr Lys Glu Trp Thr Met Pro Gln Ser
            595                 600                 605

Ser Arg Ala Gln Thr Leu Ala Met Asn Val Arg Asn Phe Leu Lys Glu
            610                 615                 620

Asp Ala Met Lys Thr Lys Thr His Tyr His Ala Met His Ala Asp Cys
625                 630                 635                 640

Leu Gln Glu Leu Arg Arg Tyr Leu Lys Ser Gly Val Val Leu Arg Arg
                645                 650                 655

Thr

<210> SEQ ID NO 51
<211> LENGTH: 657
```

```
<212> TYPE: PRT
<213> ORGANISM: Artificial Sequence
<220> FEATURE:
<223> OTHER INFORMATION: Synthetic peptide HC_WED

<400> SEQUENCE: 51

Met Arg Pro Ile Val Leu Val Leu Leu Phe Ala Thr Ser Ala Leu Ala
1               5                   10                  15

Glu Val Gln Leu Val Glu Ser Gly Gly Gly Leu Val Gln Pro Gly Gly
            20                  25                  30

Ser Leu Arg Leu Ser Cys Ala Ala Ser Gly Phe Thr Phe Thr Ser Thr
        35                  40                  45

Gly Ile Ser Trp Val Arg Gln Ala Pro Gly Lys Gly Leu Glu Trp Val
    50                  55                  60

Gly Arg Ile Tyr Pro Thr Asn Gly Ser Thr Asn Tyr Ala Asp Ser Val
65                  70                  75                  80

Lys Gly Arg Phe Thr Ile Ser Ala Asp Thr Ser Lys Asn Thr Ala Tyr
                85                  90                  95

Leu Gln Met Asn Ser Leu Arg Ala Glu Asp Thr Ala Val Tyr Tyr Cys
            100                 105                 110

Ala Arg Thr Tyr Gly Ile Tyr Asp Leu Tyr Val Asp Tyr Thr Glu Tyr
        115                 120                 125

Val Met Asp Tyr Trp Gly Gln Gly Thr Leu Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380
```

```
Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
        420                 425                 430

Tyr Ser Lys Leu Thr Val Asp Lys Ser Arg Trp Gln Gln Gly Asn Val
    435                 440                 445

Phe Ser Cys Ser Val Met His Glu Ala Leu His Asn His Tyr Thr Gln
450                 455                 460

Lys Ser Leu Ser Leu Ser Pro Gly Gly Gly Gly Ser Glu Pro His Ser
465                 470                 475                 480

Leu Arg Tyr Asn Leu Thr Val Leu Ser Trp Asp Gly Ser Val Gln Ser
            485                 490                 495

Gly Phe Leu Thr Glu Val His Leu Asp Gly Gln Pro Phe Leu Arg Cys
        500                 505                 510

Asp Arg Gln Lys Cys Arg Ala Lys Pro Gln Gly Gln Trp Ala Glu Asp
    515                 520                 525

Val Leu Gly Asn Lys Thr Trp Asp Arg Glu Thr Arg Asp Leu Thr Gly
530                 535                 540

Trp Gly Lys Asp Leu Arg Met Thr Leu Ala His Ile Lys Asp Gln Lys
545                 550                 555                 560

Glu Gly Leu His Ser Leu Gln Glu Ile Arg Val Cys Glu Ile His Glu
            565                 570                 575

Asp Asn Ser Thr Arg Ser Ser Gln His Phe Tyr Tyr Asp Gly Glu Leu
        580                 585                 590

Phe Leu Ser Gln Asn Leu Glu Thr Lys Glu Trp Thr Met Pro Gln Ser
    595                 600                 605

Ser Arg Ala Gln Thr Leu Ala Met Asn Val Arg Asn Phe Leu Lys Glu
610                 615                 620

Asp Ala Met Glu Thr Asp Thr His Tyr His Ala Met His Ala Asp Cys
625                 630                 635                 640

Leu Gln Glu Leu Arg Arg Tyr Leu Lys Ser Gly Val Val Leu Arg Arg
            645                 650                 655

Thr

<210> SEQ ID NO 52
<211> LENGTH: 657
<212> TYPE: PRT
<213> ORGANISM: Artificial Sequence
<220> FEATURE:
<223> OTHER INFORMATION: Synthetic peptide HC_25

<400> SEQUENCE: 52

Met Arg Pro Ile Val Leu Val Leu Leu Phe Ala Thr Ser Ala Leu Ala
1               5                   10                  15

Glu Val Gln Leu Val Glu Ser Gly Gly Gly Leu Val Gln Pro Gly Gly
            20                  25                  30

Ser Leu Arg Leu Ser Cys Ala Ala Ser Gly Phe Thr Phe Thr Ser Thr
        35                  40                  45

Gly Ile Ser Trp Val Arg Gln Ala Pro Gly Lys Gly Leu Glu Trp Val
    50                  55                  60

Gly Arg Ile Tyr Pro Thr Asn Gly Ser Thr Asn Tyr Ala Asp Ser Val
65                  70                  75                  80

Lys Gly Arg Phe Thr Ile Ser Ala Asp Thr Ser Lys Asn Thr Ala Tyr
```

```
            85                  90                  95
Leu Gln Met Asn Ser Leu Arg Ala Glu Asp Thr Ala Val Tyr Tyr Cys
            100                 105                 110
Ala Arg Thr Tyr Gly Ile Tyr Asp Leu Tyr Val Asp Tyr Thr Glu Tyr
            115                 120                 125
Val Met Asp Tyr Trp Gly Gln Gly Thr Leu Val Thr Val Ser Ser Ala
    130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
            195                 200                 205
Ser Ser Val Val Thr Val Pro Ser Ser Ser Leu Gly Thr Gln Thr Tyr
    210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
            275                 280                 285
Val Val Asp Val Ser His Glu Asp Pro Glu Val Lys Phe Asn Trp Tyr
    290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
            355                 360                 365
Pro Arg Glu Pro Gln Val Tyr Thr Leu Pro Pro Ser Arg Asp Glu Leu
    370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
            435                 440                 445
Phe Ser Cys Ser Val Met His Glu Ala Leu His Asn His Tyr Thr Gln
    450                 455                 460
Lys Ser Leu Ser Leu Ser Pro Gly Gly Gly Gly Ser Glu Pro His Ser
465                 470                 475                 480
Leu Arg Tyr Asn Leu Thr Val Leu Ser Trp Asp Gly Ser Val Gln Ser
                485                 490                 495
Gly Phe Leu Thr Glu Val His Leu Asp Gly Gln Pro Phe Leu Arg Cys
            500                 505                 510
```

```
Asp Arg Gln Lys Cys Arg Ala Lys Pro Gln Gly Gln Trp Ala Glu Asp
            515                 520                 525

Val Leu Gly Asn Lys Thr Trp Asp Arg Glu Thr Arg Asp Leu Thr Gly
        530                 535                 540

Trp Gly Lys Asp Leu Arg Met Thr Leu Ala His Ile Lys Asp Gln Lys
545                 550                 555                 560

Glu Gly Leu His Ser Leu Gln Glu Ile Arg Val Cys Glu Ile His Glu
                565                 570                 575

Asp Asn Ser Thr Arg Ser Ser Gln His Phe Tyr Tyr Asp Gly Glu Leu
            580                 585                 590

Phe Leu Ser Gln Asn Leu Glu Thr Leu Glu Trp Thr Met Pro Gln Ser
        595                 600                 605

Ser Arg Ala Gln Thr Leu Ala Met Asn Val Arg Asn Phe Leu Lys Glu
        610                 615                 620

Asp Ala Met Glu Thr Asp Thr His Tyr His Ala Met Arg Ala Asp Cys
625                 630                 635                 640

Leu Ser Glu Leu Arg Arg Tyr Leu Lys Ser Gly Val Val Leu Arg Arg
                645                 650                 655

Thr

<210> SEQ ID NO 53
<211> LENGTH: 657
<212> TYPE: PRT
<213> ORGANISM: Artificial Sequence
<220> FEATURE:
<223> OTHER INFORMATION: Synthetic peptide HC_48

<400> SEQUENCE: 53

Met Arg Pro Ile Val Leu Val Leu Leu Phe Ala Thr Ser Ala Leu Ala
1               5                   10                  15

Glu Val Gln Leu Val Glu Ser Gly Gly Gly Leu Val Gln Pro Gly Gly
                20                  25                  30

Ser Leu Arg Leu Ser Cys Ala Ala Ser Gly Phe Thr Phe Thr Ser Thr
            35                  40                  45

Gly Ile Ser Trp Val Arg Gln Ala Pro Gly Lys Gly Leu Glu Trp Val
        50                  55                  60

Gly Arg Ile Tyr Pro Thr Asn Gly Ser Thr Asn Tyr Ala Asp Ser Val
65                  70                  75                  80

Lys Gly Arg Phe Thr Ile Ser Ala Asp Thr Ser Lys Asn Thr Ala Tyr
                85                  90                  95

Leu Gln Met Asn Ser Leu Arg Ala Glu Asp Thr Ala Val Tyr Tyr Cys
            100                 105                 110

Ala Arg Thr Tyr Gly Ile Tyr Asp Leu Tyr Val Asp Tyr Thr Glu Tyr
        115                 120                 125

Val Met Asp Tyr Trp Gly Gln Gly Thr Leu Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Leu Gly Thr Gln Thr Tyr
    210             215             220
Ile Cys Asn Val Asn His Lys Pro Ser Asn Thr Lys Val Asp Lys Lys
225             230             235             240
Val Glu Pro Lys Ser Cys Asp Lys Thr His Thr Cys Pro Pro Cys Pro
                245             250             255
Ala Pro Glu Leu Leu Gly Gly Pro Ser Val Phe Leu Phe Pro Pro Lys
            260             265             270
Pro Lys Asp Thr Leu Met Ile Ser Arg Thr Pro Glu Val Thr Cys Val
        275             280             285
Val Val Asp Val Ser His Glu Asp Pro Glu Val Lys Phe Asn Trp Tyr
290             295             300
Val Asp Gly Val Glu Val His Asn Ala Lys Thr Lys Pro Arg Glu Glu
305             310             315             320
Gln Tyr Asn Ser Thr Tyr Arg Val Val Ser Val Leu Thr Val Leu His
                325             330             335
Gln Asp Trp Leu Asn Gly Lys Glu Tyr Lys Cys Lys Val Ser Asn Lys
            340             345             350
Ala Leu Pro Ala Pro Ile Glu Lys Thr Ile Ser Lys Ala Lys Gly Gln
        355             360             365
Pro Arg Glu Pro Gln Val Tyr Thr Leu Pro Pro Ser Arg Asp Glu Leu
370             375             380
Thr Lys Asn Gln Val Ser Leu Thr Cys Leu Val Lys Gly Phe Tyr Pro
385             390             395             400
Ser Asp Ile Ala Val Glu Trp Glu Ser Asn Gly Gln Pro Glu Asn Asn
                405             410             415
Tyr Lys Thr Thr Pro Pro Val Leu Asp Ser Asp Gly Ser Phe Phe Leu
            420             425             430
Tyr Ser Lys Leu Thr Val Asp Lys Ser Arg Trp Gln Gln Gly Asn Val
        435             440             445
Phe Ser Cys Ser Val Met His Glu Ala Leu His Asn His Tyr Thr Gln
450             455             460
Lys Ser Leu Ser Leu Ser Pro Gly Gly Gly Gly Ser Glu Pro His Ser
465             470             475             480
Leu Arg Tyr Asn Leu Thr Val Leu Ser Trp Asp Gly Ser Val Gln Ser
                485             490             495
Gly Phe Leu Thr Glu Val His Leu Asp Gly Gln Pro Phe Leu Arg Cys
            500             505             510
Asp Arg Gln Lys Cys Arg Ala Lys Pro Gln Gly Gln Trp Ala Glu Asp
        515             520             525
Val Leu Gly Asn Lys Thr Trp Asp Arg Glu Thr Arg Asp Leu Thr Gly
530             535             540
Trp Gly Lys Asp Leu Arg Met Thr Leu Ala His Ile Lys Asp Gln Lys
545             550             555             560
Glu Gly Leu His Ser Leu Gln Glu Ile Arg Val Cys Glu Ile His Glu
                565             570             575
Asp Asn Ser Thr Arg Ser Ser Gln His Phe Tyr Tyr Asp Gly Glu Leu
            580             585             590
Phe Leu Ser Gln Asn Leu Glu Thr Leu Glu Trp Thr Met Pro Gln Ser
        595             600             605
Ser Arg Ala Gln Thr Leu Ala Met Asn Val Arg Asn Phe Leu Lys Glu
610             615             620
Asp Ala Met Ala Thr Asp Thr His Tyr Ile Ala Met Arg Ala Asp Cys
```

```
                625                 630                 635                 640
Leu Ala Glu Leu Arg Arg Tyr Leu Lys Ser Gly Val Val Leu Arg Arg
                    645                 650                 655
Thr

<210> SEQ ID NO 54
<211> LENGTH: 422
<212> TYPE: PRT
<213> ORGANISM: Artificial Sequence
<220> FEATURE:
<223> OTHER INFORMATION: Synthetic peptide LC_WT

<400> SEQUENCE: 54

Met Arg Pro Ile Val Leu Val Leu Leu Phe Ala Thr Ser Ala Leu Ala
1               5                   10                  15

Asp Ile Gln Met Thr Gln Ser Pro Ser Ser Leu Ser Ala Ser Val Gly
                20                  25                  30

Asp Arg Val Thr Ile Thr Cys Arg Ala Ser Gln Asp Val Ser Thr Ala
            35                  40                  45

Val Ala Trp Tyr Gln Gln Lys Pro Gly Lys Ala Pro Lys Leu Leu Ile
        50                  55                  60

Tyr Ser Ala Ser Phe Leu Tyr Ser Gly Val Pro Ser Arg Phe Ser Gly
65                  70                  75                  80

Ser Gly Ser Gly Thr Asp Phe Thr Leu Thr Ile Ser Ser Leu Gln Pro
                85                  90                  95

Glu Asp Phe Ala Thr Tyr Tyr Cys Gln Gln Ser Tyr Thr Thr Pro Pro
            100                 105                 110

Thr Phe Gly Gln Gly Thr Lys Val Glu Ile Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys Ala Pro Thr Ser Ser Gly Gly Gly Gly
225                 230                 235                 240

Ser Glu Pro His Ser Leu Arg Tyr Asn Leu Thr Val Leu Ser Trp Asp
                245                 250                 255

Gly Ser Val Gln Ser Gly Phe Leu Thr Glu Val His Leu Asp Gly Gln
            260                 265                 270

Pro Phe Leu Arg Cys Asp Arg Gln Lys Cys Arg Ala Lys Pro Gln Gly
        275                 280                 285

Gln Trp Ala Glu Asp Val Leu Gly Asn Lys Thr Trp Asp Arg Glu Thr
    290                 295                 300

Arg Asp Leu Thr Gly Asn Gly Lys Asp Leu Arg Met Thr Leu Ala His
305                 310                 315                 320

Ile Lys Asp Gln Lys Glu Gly Leu His Ser Leu Gln Glu Ile Arg Val
                325                 330                 335
```

```
Cys Glu Ile His Glu Asp Asn Ser Thr Arg Ser Ser Gln His Phe Tyr
            340                 345                 350

Tyr Asp Gly Glu Leu Phe Leu Ser Gln Asn Leu Glu Thr Lys Glu Trp
            355                 360                 365

Thr Met Pro Gln Ser Ser Arg Ala Gln Thr Leu Ala Met Asn Val Arg
            370                 375                 380

Asn Phe Leu Lys Glu Asp Ala Met Lys Thr Lys Thr His Tyr His Ala
385                 390                 395                 400

Met His Ala Asp Cys Leu Gln Glu Leu Arg Arg Tyr Leu Lys Ser Gly
                405                 410                 415

Val Val Leu Arg Arg Thr
            420

<210> SEQ ID NO 55
<211> LENGTH: 422
<212> TYPE: PRT
<213> ORGANISM: Artificial Sequence
<220> FEATURE:
<223> OTHER INFORMATION: Synthetic peptide LC_WED

<400> SEQUENCE: 55

Met Arg Pro Ile Val Leu Val Leu Leu Phe Ala Thr Ser Ala Leu Ala
1               5                   10                  15

Asp Ile Gln Met Thr Gln Ser Pro Ser Ser Leu Ser Ala Ser Val Gly
            20                  25                  30

Asp Arg Val Thr Ile Thr Cys Arg Ala Ser Gln Asp Val Ser Thr Ala
        35                  40                  45

Val Ala Trp Tyr Gln Gln Lys Pro Gly Lys Ala Pro Lys Leu Leu Ile
    50                  55                  60

Tyr Ser Ala Ser Phe Leu Tyr Ser Gly Val Pro Ser Arg Phe Ser Gly
65                  70                  75                  80

Ser Gly Ser Gly Thr Asp Phe Thr Leu Thr Ile Ser Ser Leu Gln Pro
                85                  90                  95

Glu Asp Phe Ala Thr Tyr Tyr Cys Gln Gln Ser Tyr Thr Thr Pro Pro
            100                 105                 110

Thr Phe Gly Gln Gly Thr Lys Val Glu Ile Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys Ala Pro Thr Ser Ser Gly Gly Gly Gly
225                 230                 235                 240

Ser Glu Pro His Ser Leu Arg Tyr Asn Leu Thr Val Leu Ser Trp Asp
                245                 250                 255

Gly Ser Val Gln Ser Gly Phe Leu Thr Glu Val His Leu Asp Gly Gln
            260                 265                 270
```

```
Pro Phe Leu Arg Cys Asp Arg Gln Lys Cys Arg Ala Lys Pro Gln Gly
            275                 280                 285

Gln Trp Ala Glu Asp Val Leu Gly Asn Lys Thr Trp Asp Arg Glu Thr
290                 295                 300

Arg Asp Leu Thr Gly Trp Gly Lys Asp Leu Arg Met Thr Leu Ala His
305                 310                 315                 320

Ile Lys Asp Gln Lys Glu Gly Leu His Ser Leu Gln Glu Ile Arg Val
            325                 330                 335

Cys Glu Ile His Glu Asp Asn Ser Thr Arg Ser Ser Gln His Phe Tyr
            340                 345                 350

Tyr Asp Gly Glu Leu Phe Leu Ser Gln Asn Leu Glu Thr Lys Glu Trp
            355                 360                 365

Thr Met Pro Gln Ser Ser Arg Ala Gln Thr Leu Ala Met Asn Val Arg
            370                 375                 380

Asn Phe Leu Lys Glu Asp Ala Met Glu Thr His Tyr His Ala
385                 390                 395                 400

Met His Ala Asp Cys Leu Gln Glu Leu Arg Arg Tyr Leu Lys Ser Gly
            405                 410                 415

Val Val Leu Arg Arg Thr
            420

<210> SEQ ID NO 56
<211> LENGTH: 422
<212> TYPE: PRT
<213> ORGANISM: Artificial Sequence
<220> FEATURE:
<223> OTHER INFORMATION: Synthetic peptide LC_25

<400> SEQUENCE: 56

Met Arg Pro Ile Val Leu Val Leu Leu Phe Ala Thr Ser Ala Leu Ala
1               5                   10                  15

Asp Ile Gln Met Thr Gln Ser Pro Ser Ser Leu Ser Ala Ser Val Gly
            20                  25                  30

Asp Arg Val Thr Ile Thr Cys Arg Ala Ser Gln Asp Val Ser Thr Ala
        35                  40                  45

Val Ala Trp Tyr Gln Gln Lys Pro Gly Lys Ala Pro Lys Leu Leu Ile
    50                  55                  60

Tyr Ser Ala Ser Phe Leu Tyr Ser Gly Val Pro Ser Arg Phe Ser Gly
65                  70                  75                  80

Ser Gly Ser Gly Thr Asp Phe Thr Leu Thr Ile Ser Ser Leu Gln Pro
                85                  90                  95

Glu Asp Phe Ala Thr Tyr Tyr Cys Gln Gln Ser Tyr Thr Thr Pro Pro
            100                 105                 110

Thr Phe Gly Gln Gly Thr Lys Val Glu Ile Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205
```

Ala Cys Glu Val Thr His Gln Gly Leu Ser Ser Pro Val Thr Lys Ser
        210                 215                 220

Phe Asn Arg Gly Glu Cys Ala Pro Thr Ser Ser Ser Gly Gly Gly Gly
225                 230                 235                 240

Ser Glu Pro His Ser Leu Arg Tyr Asn Leu Thr Val Leu Ser Trp Asp
                245                 250                 255

Gly Ser Val Gln Ser Gly Phe Leu Thr Glu Val His Leu Asp Gly Gln
                260                 265                 270

Pro Phe Leu Arg Cys Asp Arg Gln Lys Cys Arg Ala Lys Pro Gln Gly
            275                 280                 285

Gln Trp Ala Glu Asp Val Leu Gly Asn Lys Thr Trp Asp Arg Glu Thr
290                 295                 300

Arg Asp Leu Thr Gly Trp Gly Lys Asp Leu Arg Met Thr Leu Ala His
305                 310                 315                 320

Ile Lys Asp Gln Lys Glu Gly Leu His Ser Leu Gln Glu Ile Arg Val
                325                 330                 335

Cys Glu Ile His Glu Asp Asn Ser Thr Arg Ser Ser Gln His Phe Tyr
            340                 345                 350

Tyr Asp Gly Glu Leu Phe Leu Ser Gln Asn Leu Glu Thr Leu Glu Trp
        355                 360                 365

Thr Met Pro Gln Ser Ser Arg Ala Gln Thr Leu Ala Met Asn Val Arg
370                 375                 380

Asn Phe Leu Lys Glu Asp Ala Met Glu Thr Asp Thr His Tyr His Ala
385                 390                 395                 400

Met Arg Ala Asp Cys Leu Ser Glu Leu Arg Arg Tyr Leu Lys Ser Gly
                405                 410                 415

Val Val Leu Arg Arg Thr
                420

<210> SEQ ID NO 57
<211> LENGTH: 422
<212> TYPE: PRT
<213> ORGANISM: Artificial Sequence
<220> FEATURE:
<223> OTHER INFORMATION: Synthetic peptide LC_48

<400> SEQUENCE: 57

Met Arg Pro Ile Val Leu Val Leu Leu Phe Ala Thr Ser Ala Leu Ala
1               5                   10                  15

Asp Ile Gln Met Thr Gln Ser Pro Ser Ser Leu Ser Ala Ser Val Gly
                20                  25                  30

Asp Arg Val Thr Ile Thr Cys Arg Ala Ser Gln Asp Val Ser Thr Ala
            35                  40                  45

Val Ala Trp Tyr Gln Gln Lys Pro Gly Lys Ala Pro Lys Leu Leu Ile
        50                  55                  60

Tyr Ser Ala Ser Phe Leu Tyr Ser Gly Val Pro Ser Arg Phe Ser Gly
65                  70                  75                  80

Ser Gly Ser Gly Thr Asp Phe Thr Leu Thr Ile Ser Ser Leu Gln Pro
                85                  90                  95

Glu Asp Phe Ala Thr Tyr Tyr Cys Gln Gln Ser Tyr Thr Thr Pro Pro
            100                 105                 110

Thr Phe Gly Gln Gly Thr Lys Val Glu Ile Lys Arg Thr Val Ala Ala
        115                 120                 125

Pro Ser Val Phe Ile Phe Pro Pro Ser Asp Glu Gln Leu Lys Ser Gly
        130                 135                 140

```
Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
            165                 170                 175

Glu Ser Val Thr Glu Gln Asp Ser Lys Asp Ser Thr Tyr Ser Leu Ser
        180                 185                 190

Ser Thr Leu Thr Leu Ser Lys Ala Asp Tyr Glu Lys His Lys Val Tyr
            195                 200                 205

Ala Cys Glu Val Thr His Gln Gly Leu Ser Ser Pro Val Thr Lys Ser
        210                 215                 220

Phe Asn Arg Gly Glu Cys Ala Pro Thr Ser Ser Gly Gly Gly
225                 230                 235                 240

Ser Glu Pro His Ser Leu Arg Tyr Asn Leu Thr Val Leu Ser Trp Asp
                245                 250                 255

Gly Ser Val Gln Ser Gly Phe Leu Thr Glu Val His Leu Asp Gly Gln
            260                 265                 270

Pro Phe Leu Arg Cys Asp Arg Gln Lys Cys Arg Ala Lys Pro Gln Gly
            275                 280                 285

Gln Trp Ala Glu Asp Val Leu Gly Asn Lys Thr Trp Asp Arg Glu Thr
290                 295                 300

Arg Asp Leu Thr Gly Trp Gly Lys Asp Leu Arg Met Thr Leu Ala His
305                 310                 315                 320

Ile Lys Asp Gln Lys Glu Gly Leu His Ser Leu Gln Glu Ile Arg Val
            325                 330                 335

Cys Glu Ile His Glu Asp Asn Ser Thr Arg Ser Ser Gln His Phe Tyr
            340                 345                 350

Tyr Asp Gly Glu Leu Phe Leu Ser Gln Asn Leu Glu Thr Leu Glu Trp
            355                 360                 365

Thr Met Pro Gln Ser Ser Arg Ala Gln Thr Leu Ala Met Asn Val Arg
370                 375                 380

Asn Phe Leu Lys Glu Asp Ala Met Ala Thr Asp Thr His Tyr Ile Ala
385                 390                 395                 400

Met Arg Ala Asp Cys Leu Ala Glu Leu Arg Arg Tyr Leu Lys Ser Gly
            405                 410                 415

Val Val Leu Arg Arg Thr
            420

<210> SEQ ID NO 58
<211> LENGTH: 649
<212> TYPE: PRT
<213> ORGANISM: Artificial Sequence
<220> FEATURE:
<223> OTHER INFORMATION: Synthetic peptide cetuximab HC_25

<400> SEQUENCE: 58

Met Arg Pro Ile Val Leu Val Leu Leu Phe Ala Thr Ser Ala Leu Ala
1               5                   10                  15

Gln Val Gln Leu Lys Gln Ser Gly Pro Gly Leu Val Gln Pro Ser Gln
            20                  25                  30

Ser Leu Ser Ile Thr Cys Thr Val Ser Gly Phe Ser Leu Thr Asn Tyr
        35                  40                  45

Gly Val His Trp Val Arg Gln Ser Pro Gly Lys Gly Leu Glu Trp Leu
    50                  55                  60

Gly Val Ile Trp Ser Gly Gly Asn Thr Asp Tyr Asn Thr Pro Phe Thr
65                  70                  75                  80
```

```
Ser Arg Leu Ser Ile Asn Lys Asp Asn Ser Lys Ser Gln Val Phe Phe
            85                  90                  95

Lys Met Asn Ser Leu Gln Ser Asn Asp Thr Ala Ile Tyr Tyr Cys Ala
            100                 105                 110

Arg Ala Leu Thr Tyr Tyr Asp Tyr Glu Phe Ala Tyr Trp Gly Gln Gly
            115                 120                 125

Thr Leu Val Thr Val Ser Ala Ala Ser Thr Lys Gly Pro Ser Val Phe
        130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
            195                 200                 205

Ser Ser Leu Gly Thr Gln Thr Tyr Ile Cys Asn Val Asn His Lys Pro
        210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
        370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
        450                 455                 460

Gly Gly Gly Ser Glu Pro His Ser Leu Arg Tyr Asn Leu Thr Val Leu
465                 470                 475                 480

Ser Trp Asp Gly Ser Val Gln Ser Gly Phe Leu Thr Glu Val His Leu
                485                 490                 495
```

```
Asp Gly Gln Pro Phe Leu Arg Cys Asp Arg Gln Lys Cys Arg Ala Lys
            500                 505                 510

Pro Gln Gly Gln Trp Ala Glu Asp Val Leu Gly Asn Lys Thr Trp Asp
        515                 520                 525

Arg Glu Thr Arg Asp Leu Thr Gly Trp Gly Lys Asp Leu Arg Met Thr
    530                 535                 540

Leu Ala His Ile Lys Asp Gln Lys Glu Gly Leu His Ser Leu Gln Glu
545                 550                 555                 560

Ile Arg Val Cys Glu Ile His Glu Asp Asn Ser Thr Arg Ser Ser Gln
                565                 570                 575

His Phe Tyr Tyr Asp Gly Glu Leu Phe Leu Ser Gln Asn Leu Glu Thr
            580                 585                 590

Leu Glu Trp Thr Met Pro Gln Ser Ser Arg Ala Gln Thr Leu Ala Met
        595                 600                 605

Asn Val Arg Asn Phe Leu Lys Glu Asp Ala Met Glu Thr Asp Thr His
    610                 615                 620

Tyr His Ala Met Arg Ala Asp Cys Leu Ser Glu Leu Arg Arg Tyr Leu
625                 630                 635                 640

Lys Ser Gly Val Val Leu Arg Arg Thr
                645

<210> SEQ ID NO 59
<211> LENGTH: 422
<212> TYPE: PRT
<213> ORGANISM: Artificial Sequence
<220> FEATURE:
<223> OTHER INFORMATION: Synthetic peptide cetuximab LC_25

<400> SEQUENCE: 59

Met Arg Pro Ile Val Leu Val Leu Leu Phe Ala Thr Ser Ala Leu Ala
1               5                   10                  15

Asp Ile Leu Leu Thr Gln Ser Pro Val Ile Leu Ser Val Ser Pro Gly
            20                  25                  30

Glu Arg Val Ser Phe Ser Cys Arg Ala Ser Gln Ser Ile Gly Thr Asn
        35                  40                  45

Ile His Trp Tyr Gln Gln Arg Thr Asn Gly Ser Pro Arg Leu Leu Ile
    50                  55                  60

Lys Tyr Ala Ser Glu Ser Ile Ser Gly Ile Pro Ser Arg Phe Ser Gly
65                  70                  75                  80

Ser Gly Ser Gly Thr Asp Phe Thr Leu Ser Ile Asn Ser Val Glu Ser
                85                  90                  95

Glu Asp Ile Ala Asp Tyr Tyr Cys Gln Gln Asn Asn Asn Trp Pro Thr
            100                 105                 110

Thr Phe Gly Ala Gly Thr Lys Leu Glu Leu Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205
```

```
Ala Cys Glu Val Thr His Gln Gly Leu Ser Ser Pro Val Thr Lys Ser
    210                 215                 220

Phe Asn Arg Gly Glu Cys Ala Pro Thr Ser Ser Ser Gly Gly Gly Gly
225                 230                 235                 240

Ser Glu Pro His Ser Leu Arg Tyr Asn Leu Thr Val Leu Ser Trp Asp
                245                 250                 255

Gly Ser Val Gln Ser Gly Phe Leu Thr Glu Val His Leu Asp Gly Gln
            260                 265                 270

Pro Phe Leu Arg Cys Asp Arg Gln Lys Cys Arg Ala Lys Pro Gln Gly
        275                 280                 285

Gln Trp Ala Glu Asp Val Leu Gly Asn Lys Thr Trp Asp Arg Glu Thr
290                 295                 300

Arg Asp Leu Thr Gly Trp Gly Lys Asp Leu Arg Met Thr Leu Ala His
305                 310                 315                 320

Ile Lys Asp Gln Lys Glu Gly Leu His Ser Leu Gln Glu Ile Arg Val
                325                 330                 335

Cys Glu Ile His Glu Asp Asn Ser Thr Arg Ser Ser Gln His Phe Tyr
            340                 345                 350

Tyr Asp Gly Glu Leu Phe Leu Ser Gln Asn Leu Glu Thr Leu Glu Trp
        355                 360                 365

Thr Met Pro Gln Ser Ser Arg Ala Gln Thr Leu Ala Met Asn Val Arg
370                 375                 380

Asn Phe Leu Lys Glu Asp Ala Met Glu Thr Asp Thr His Tyr His Ala
385                 390                 395                 400

Met Arg Ala Asp Cys Leu Ser Glu Leu Arg Arg Tyr Leu Lys Ser Gly
                405                 410                 415

Val Val Leu Arg Arg Thr
            420

<210> SEQ ID NO 60
<211> LENGTH: 650
<212> TYPE: PRT
<213> ORGANISM: Artificial Sequence
<220> FEATURE:
<223> OTHER INFORMATION: Synthetic peptide trastuzumab HC_25

<400> SEQUENCE: 60

Met Arg Pro Ile Val Leu Val Leu Leu Phe Ala Thr Ser Ala Leu Ala
1               5                   10                  15

Glu Val Gln Leu Val Glu Ser Gly Gly Gly Leu Val Gln Pro Gly Gly
            20                  25                  30

Ser Leu Arg Leu Ser Cys Ala Ala Ser Gly Phe Asn Ile Lys Asp Thr
        35                  40                  45

Tyr Ile His Trp Val Arg Gln Ala Pro Gly Lys Gly Leu Glu Trp Val
    50                  55                  60

Ala Arg Ile Tyr Pro Thr Asn Gly Tyr Thr Arg Tyr Ala Asp Ser Val
65                  70                  75                  80

Lys Gly Arg Phe Thr Ile Ser Ala Asp Thr Ser Lys Asn Thr Ala Tyr
                85                  90                  95

Leu Gln Met Asn Ser Leu Arg Ala Glu Asp Thr Ala Val Tyr Tyr Cys
            100                 105                 110

Ser Arg Trp Gly Gly Asp Gly Phe Tyr Ala Met Asp Tyr Trp Gly Gln
        115                 120                 125

Gly Thr Leu Val Thr Val Ser Ser Ala Ser Thr Lys Gly Pro Ser Val
    130                 135                 140
```

```
Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
            165                 170                 175

Trp Asn Ser Gly Ala Leu Thr Ser Gly Val His Thr Phe Pro Ala Val
        180                 185                 190

Leu Gln Ser Ser Gly Leu Tyr Ser Leu Ser Ser Val Val Thr Val Pro
    195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Gly Gly Gly Ser Glu Pro His Ser Leu Arg Tyr Asn Leu Thr Val
465                 470                 475                 480

Leu Ser Trp Asp Gly Ser Val Gln Ser Gly Phe Leu Thr Glu Val His
                485                 490                 495

Leu Asp Gly Gln Pro Phe Leu Arg Cys Asp Arg Gln Lys Cys Arg Ala
            500                 505                 510

Lys Pro Gln Gly Gln Trp Ala Glu Asp Val Leu Gly Asn Lys Thr Trp
        515                 520                 525

Asp Arg Glu Thr Arg Asp Leu Thr Gly Trp Gly Lys Asp Leu Arg Met
    530                 535                 540

Thr Leu Ala His Ile Lys Asp Gln Lys Glu Gly Leu His Ser Leu Gln
545                 550                 555                 560

Glu Ile Arg Val Cys Glu Ile His Glu Asp Asn Ser Thr Arg Ser Ser
```

```
                  565                 570                 575
Gln His Phe Tyr Tyr Asp Gly Glu Leu Phe Leu Ser Gln Asn Leu Glu
            580                 585                 590

Thr Leu Glu Trp Thr Met Pro Gln Ser Ser Arg Ala Gln Thr Leu Ala
            595                 600                 605

Met Asn Val Arg Asn Phe Leu Lys Glu Asp Ala Met Glu Thr Asp Thr
            610                 615                 620

His Tyr His Ala Met Arg Ala Asp Cys Leu Ser Glu Leu Arg Arg Tyr
625                 630                 635                 640

Leu Lys Ser Gly Val Val Leu Arg Arg Thr
            645                 650

<210> SEQ ID NO 61
<211> LENGTH: 422
<212> TYPE: PRT
<213> ORGANISM: Artificial Sequence
<220> FEATURE:
<223> OTHER INFORMATION: Synthetic peptide trastuzumab LC_25

<400> SEQUENCE: 61

Met Arg Pro Ile Val Leu Val Leu Leu Phe Ala Thr Ser Ala Leu Ala
1               5                   10                  15

Asp Ile Gln Met Thr Gln Ser Pro Ser Ser Leu Ser Ala Ser Val Gly
            20                  25                  30

Asp Arg Val Thr Ile Thr Cys Arg Ala Ser Gln Asp Val Asn Thr Ala
        35                  40                  45

Val Ala Trp Tyr Gln Gln Lys Pro Gly Lys Ala Pro Lys Leu Leu Ile
    50                  55                  60

Tyr Ser Ala Ser Phe Leu Tyr Ser Gly Val Pro Ser Arg Phe Ser Gly
65                  70                  75                  80

Ser Arg Ser Gly Thr Asp Phe Thr Leu Thr Ile Ser Ser Leu Gln Pro
                85                  90                  95

Glu Asp Phe Ala Thr Tyr Tyr Cys Gln Gln His Tyr Thr Thr Pro Pro
            100                 105                 110

Thr Phe Gly Gln Gly Thr Lys Val Glu Ile Lys Arg Thr Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys Ala Pro Thr Ser Ser Ser Gly Gly Gly Gly
225                 230                 235                 240

Ser Glu Pro His Ser Leu Arg Tyr Asn Leu Thr Val Leu Ser Trp Asp
                245                 250                 255

Gly Ser Val Gln Ser Gly Phe Leu Thr Glu Val His Leu Asp Gly Gln
            260                 265                 270

Pro Phe Leu Arg Cys Asp Arg Gln Lys Cys Arg Ala Lys Pro Gln Gly
```

```
                275                 280                 285
Gln Trp Ala Glu Asp Val Leu Gly Asn Lys Thr Trp Asp Arg Glu Thr
290                 295                 300
Arg Asp Leu Thr Gly Trp Gly Lys Asp Leu Arg Met Thr Leu Ala His
305                 310                 315                 320
Ile Lys Asp Gln Lys Glu Gly Leu His Ser Leu Gln Glu Ile Arg Val
                325                 330                 335
Cys Glu Ile His Glu Asp Asn Ser Thr Arg Ser Ser Gln His Phe Tyr
                340                 345                 350
Tyr Asp Gly Glu Leu Phe Leu Ser Gln Asn Leu Glu Thr Leu Glu Trp
                355                 360                 365
Thr Met Pro Gln Ser Ser Arg Ala Gln Thr Leu Ala Met Asn Val Arg
370                 375                 380
Asn Phe Leu Lys Glu Asp Ala Met Glu Thr Asp Thr His Tyr His Ala
385                 390                 395                 400
Met Arg Ala Asp Cys Leu Ser Glu Leu Arg Arg Tyr Leu Lys Ser Gly
                405                 410                 415
Val Val Leu Arg Arg Thr
                420

<210> SEQ ID NO 62
<211> LENGTH: 650
<212> TYPE: PRT
<213> ORGANISM: Artificial Sequence
<220> FEATURE:
<223> OTHER INFORMATION: Synthetic peptide anti-PDL1 HC_25

<400> SEQUENCE: 62

Met Arg Pro Ile Val Leu Val Leu Leu Phe Ala Thr Ser Ala Leu Ala
1               5                   10                  15
Glu Val Gln Leu Leu Glu Ser Gly Gly Gly Leu Val Gln Pro Gly Gly
                20                  25                  30
Ser Leu Arg Leu Ser Cys Ala Ala Ser Gly Phe Thr Phe Ser Met Tyr
                35                  40                  45
Met Met Met Trp Val Arg Gln Ala Pro Gly Lys Gly Leu Glu Val Trp
50                  55                  60
Ser Ser Ile Tyr Pro Ser Gly Gly Ile Thr Phe Tyr Ala Asp Ser Val
65                  70                  75                  80
Lys Gly Arg Phe Thr Ile Ser Arg Asp Asn Ser Lys Asn Thr Leu Tyr
                85                  90                  95
Leu Gln Met Asn Ser Leu Arg Ala Glu Asp Thr Ala Ile Tyr Tyr Cys
                100                 105                 110
Ala Arg Ile Lys Leu Gly Thr Val Thr Thr Val Asp Tyr Trp Gly Gln
                115                 120                 125
Gly Thr Leu Val Thr Val Ser Ser Ala Ser Thr Lys Gly Pro Ser Val
                130                 135                 140
Phe Pro Leu Ala Pro Ser Ser Lys Ser Thr Ser Gly Gly Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
                180                 185                 190
Leu Gln Ser Ser Gly Leu Tyr Ser Leu Ser Ser Val Val Thr Val Pro
                195                 200                 205
Ser Ser Ser Leu Gly Thr Gln Thr Tyr Ile Cys Asn Val Asn His Lys
```

-continued

```
            210                 215                 220
Pro Ser Asn Thr Lys Val Asp Lys Lys Val Glu Pro Lys Ser Cys Asp
225                 230                 235                 240
Lys Thr His Thr Cys Pro Pro Cys Pro Ala Pro Glu Leu Leu Gly Gly
                    245                 250                 255
Pro Ser Val Phe Leu Phe Pro Pro Lys Pro Lys Asp Thr Leu Met Ile
                260                 265                 270
Ser Arg Thr Pro Glu Val Thr Cys Val Val Val Asp Val Ser His Glu
            275                 280                 285
Asp Pro Glu Val Lys Phe Asn Trp Tyr Val Asp Gly Val Glu Val His
        290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                    325                 330                 335
Glu Tyr Lys Cys Lys Val Ser Asn Lys Ala Leu Pro Ala Pro Ile Glu
                340                 345                 350
Lys Thr Ile Ser Lys Ala Lys Gly Gln Pro Arg Glu Pro Gln Val Tyr
            355                 360                 365
Thr Leu Pro Pro Ser Arg Asp Glu Leu Thr Lys Asn Gln Val Ser Leu
        370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                    405                 410                 415
Leu Asp Ser Asp Gly Ser Phe Phe Leu Tyr Ser Lys Leu Thr Val Asp
                420                 425                 430
Lys Ser Arg Trp Gln Gln Gly Asn Val Phe Ser Cys Ser Val Met His
            435                 440                 445
Glu Ala Leu His Asn His Tyr Thr Gln Lys Ser Leu Ser Leu Ser Pro
        450                 455                 460
Gly Gly Gly Gly Ser Glu Pro His Ser Leu Arg Tyr Asn Leu Thr Val
465                 470                 475                 480
Leu Ser Trp Asp Gly Ser Val Gln Ser Gly Phe Leu Thr Glu Val His
                    485                 490                 495
Leu Asp Gly Gln Pro Phe Leu Arg Cys Asp Arg Gln Lys Cys Arg Ala
                500                 505                 510
Lys Pro Gln Gly Gln Trp Ala Glu Asp Val Leu Gly Asn Lys Thr Trp
            515                 520                 525
Asp Arg Glu Thr Arg Asp Leu Thr Gly Trp Gly Lys Asp Leu Arg Met
        530                 535                 540
Thr Leu Ala His Ile Lys Asp Gln Lys Glu Gly Leu His Ser Leu Gln
545                 550                 555                 560
Glu Ile Arg Val Cys Glu Ile His Glu Asp Asn Ser Thr Arg Ser Ser
                    565                 570                 575
Gln His Phe Tyr Tyr Asp Gly Glu Leu Phe Leu Ser Gln Asn Leu Glu
                580                 585                 590
Thr Leu Glu Trp Thr Met Pro Gln Ser Ser Arg Ala Gln Thr Leu Ala
            595                 600                 605
Met Asn Val Arg Asn Phe Leu Lys Glu Asp Ala Met Glu Thr Asp Thr
        610                 615                 620
His Tyr His Ala Met Arg Ala Asp Cys Leu Ser Glu Leu Arg Arg Tyr
625                 630                 635                 640
```

```
Leu Lys Ser Gly Val Val Leu Arg Arg Thr
            645                 650

<210> SEQ ID NO 63
<211> LENGTH: 425
<212> TYPE: PRT
<213> ORGANISM: Artificial Sequence
<220> FEATURE:
<223> OTHER INFORMATION: Synthetic peptide anti-PDL1 LC_25

<400> SEQUENCE: 63

Met Arg Pro Ile Val Leu Val Leu Leu Phe Ala Thr Ser Ala Leu Ala
1               5                   10                  15

Gln Ser Ala Leu Thr Gln Pro Ala Ser Val Ser Gly Ser Pro Gly Gln
            20                  25                  30

Ser Ile Thr Ile Ser Cys Thr Gly Thr Ser Ser Asp Val Gly Ala Tyr
        35                  40                  45

Asn Tyr Val Ser Trp Tyr Gln Gln His Pro Gly Lys Ala Pro Lys Leu
50                  55                  60

Met Ile Tyr Asp Val Ser Asn Arg Pro Ser Gly Val Ser Asn Arg Phe
65                  70                  75                  80

Ser Gly Ser Lys Ser Gly Asn Thr Ala Ser Leu Thr Ile Ser Gly Leu
                85                  90                  95

Gln Ala Glu Asp Glu Ala Asp Tyr Tyr Cys Ser Ser Tyr Thr Ser Ser
            100                 105                 110

Ser Thr Arg Val Phe Gly Thr Gly Thr Lys Val Thr Val Leu Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
210                 215                 220

Thr Lys Ser Phe Asn Arg Gly Glu Cys Ala Pro Thr Ser Ser Ser Gly
225                 230                 235                 240

Gly Gly Gly Ser Glu Pro His Ser Leu Arg Tyr Asn Leu Thr Val Leu
                245                 250                 255

Ser Trp Asp Gly Ser Val Gln Ser Gly Phe Leu Thr Glu Val His Leu
            260                 265                 270

Asp Gly Gln Pro Phe Leu Arg Cys Asp Arg Gln Lys Cys Arg Ala Lys
        275                 280                 285

Pro Gln Gly Gln Trp Ala Glu Asp Val Leu Gly Asn Lys Thr Trp Asp
290                 295                 300

Arg Glu Thr Arg Asp Leu Thr Gly Trp Gly Lys Asp Leu Arg Met Thr
305                 310                 315                 320

Leu Ala His Ile Lys Asp Gln Lys Glu Gly Leu His Ser Leu Gln Glu
                325                 330                 335

Ile Arg Val Cys Glu Ile His Glu Asp Asn Ser Thr Arg Ser Ser Gln
            340                 345                 350
```

His Phe Tyr Tyr Asp Gly Glu Leu Phe Leu Ser Gln Asn Leu Glu Thr
            355                 360                 365

Leu Glu Trp Thr Met Pro Gln Ser Ser Arg Ala Gln Thr Leu Ala Met
        370                 375                 380

Asn Val Arg Asn Phe Leu Lys Glu Asp Ala Met Glu Thr Asp Thr His
385                 390                 395                 400

Tyr His Ala Met Arg Ala Asp Cys Leu Ser Glu Leu Arg Arg Tyr Leu
                405                 410                 415

Lys Ser Gly Val Val Leu Arg Arg Thr
            420                 425

<210> SEQ ID NO 64
<211> LENGTH: 274
<212> TYPE: PRT
<213> ORGANISM: Homo sapiens

<400> SEQUENCE: 64

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr Leu Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 65

<211> LENGTH: 274
<212> TYPE: PRT
<213> ORGANISM: Homo sapiens

<400> SEQUENCE: 65

```
Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Ile Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser
```

<210> SEQ ID NO 66
<211> LENGTH: 274
<212> TYPE: PRT
<213> ORGANISM: Homo sapiens

<400> SEQUENCE: 66

```
Glu Pro His Ser Leu Pro Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60
```

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
            85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
            115                 120                 125

Met Pro Gln Ser Ser Arg Ala Gln Thr Leu Ala Met Asn Val Arg Asn
            130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
            195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 67
<211> LENGTH: 274
<212> TYPE: PRT
<213> ORGANISM: Homo sapiens

<400> SEQUENCE: 67

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
            85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Trp Thr
            115                 120                 125

Val Pro Gln Ser Ser Arg Ala Gln Thr Leu Ala Met Asn Val Arg Asn
            130                 135                 140

Phe Leu Lys Glu Asp Ala Met Lys Thr Lys Thr His Tyr His Ala Met
145                 150                 155                 160

```
His Ala Asp Cys Leu Gln Glu Leu Arg Arg Tyr Leu Glu Ser Gly Val
            165                 170                 175

Val Leu Arg Arg Thr Val Pro Pro Met Val Asn Val Thr Arg Ser Glu
        180                 185                 190

Ala Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
        210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 68
<211> LENGTH: 274
<212> TYPE: PRT
<213> ORGANISM: Homo sapiens

<400> SEQUENCE: 68

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
            165                 170                 175

Val Leu Arg Arg Thr Val Pro Pro Met Val Asn Val Thr Arg Ser Glu
        180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
        210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255
```

Phe Thr Cys Tyr Met Glu His Ser Gly Asn His Ser Thr His Pro Val
                260                 265                 270

Pro Ser

<210> SEQ ID NO 69
<211> LENGTH: 274
<212> TYPE: PRT
<213> ORGANISM: Homo sapiens

<400> SEQUENCE: 69

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 70
<211> LENGTH: 276
<212> TYPE: PRT
<213> ORGANISM: Homo sapiens

<400> SEQUENCE: 70

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

```
Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser Gly Lys
        275

<210> SEQ ID NO 71
<211> LENGTH: 306
<212> TYPE: PRT
<213> ORGANISM: Homo sapiens

<400> SEQUENCE: 71

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
        35                  40                  45

Trp Ala Glu Asp Val Leu Gly Ala Lys Thr Trp Asp Thr Glu Thr Glu
    50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asp Gly Glu Leu Phe Leu Ser Gln Asn Leu Glu Thr Gln Glu Ser Thr
```

```
                115                 120                 125
Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Leu Pro Pro Met Val Asn Val
                165                 170                 175

Ile Cys Ser Glu Val Ser Glu Gly Asn Ile Thr Val Thr Cys Arg Ala
                180                 185                 190

Ser Ser Phe Tyr Pro Arg Asn Ile Thr Leu Thr Trp Arg Gln Asp Gly
                195                 200                 205

Val Ser Leu Ser His Asn Thr Gln Gln Trp Gly Asp Val Leu Pro Asp
210                 215                 220

Gly Asn Gly Thr Tyr Gln Thr Trp Val Ala Thr Arg Ile Arg Gln Gly
225                 230                 235                 240

Glu Glu Gln Arg Phe Thr Cys Tyr Met Glu His Ser Gly Asn His Gly
                245                 250                 255

Thr His Pro Val Pro Ser Gly Lys Ala Leu Val Leu Gln Ser Gln Arg
                260                 265                 270

Thr Asp Phe Pro Tyr Val Ser Ala Ala Met Pro Cys Phe Val Ile Ile
                275                 280                 285

Ile Ile Leu Cys Val Pro Cys Cys Lys Lys Thr Ser Ala Ala Glu
290                 295                 300

Gly Pro
305

<210> SEQ ID NO 72
<211> LENGTH: 318
<212> TYPE: PRT
<213> ORGANISM: Homo sapiens

<400> SEQUENCE: 72

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
                20                  25                  30

Phe Leu Arg Tyr Asp Arg Gln Lys Arg Arg Ala Lys Pro Gln Gly Gln
                35                  40                  45

Trp Ala Glu Asp Val Leu Gly Ala Glu Thr Trp Asp Thr Glu Thr Glu
50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Met His Glu Asp Ser Ser Thr Arg Gly Ser Arg His Phe Tyr Tyr
                100                 105                 110

Asn Gly Glu Leu Phe Leu Ser Gln Asn Leu Glu Thr Gln Glu Ser Thr
                115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175
```

```
Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
    210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
        275                 280                 285

Tyr Val Ser Ala Ala Met Pro Cys Phe Val Ile Ile Ile Leu Cys
    290                 295                 300

Val Pro Cys Cys Lys Lys Lys Thr Ser Ala Ala Glu Gly Pro
305                 310                 315

<210> SEQ ID NO 73
<211> LENGTH: 318
<212> TYPE: PRT
<213> ORGANISM: Homo sapiens

<400> SEQUENCE: 73

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
        35                  40                  45

Trp Ala Glu Asp Val Leu Gly Ala Lys Thr Trp Asp Thr Glu Thr Glu
    50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asp Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
    130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Ile Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
    210                 215                 220

His Asn Thr Gln Gln Trp Gly Asp Val Leu Pro Asp Gly Asn Gly Thr
225                 230                 235                 240
```

```
Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
        275                 280                 285

Tyr Val Ser Ala Ala Met Pro Cys Phe Val Ile Ile Ile Ile Leu Cys
    290                 295                 300

Val Pro Cys Cys Lys Lys Lys Thr Ser Ala Ala Glu Gly Pro
305                 310                 315

<210> SEQ ID NO 74
<211> LENGTH: 318
<212> TYPE: PRT
<213> ORGANISM: Homo sapiens

<400> SEQUENCE: 74

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
        35                  40                  45

Trp Ala Glu Asn Val Leu Gly Ala Lys Thr Trp Asp Thr Glu Thr Glu
    50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asp Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
        275                 280                 285

Tyr Val Ser Ala Ala Met Pro Cys Phe Val Ile Ile Ile Ile Leu Cys
```

```
                        290                 295                 300

Val Pro Cys Cys Lys Lys Lys Thr Ser Ala Ala Glu Gly Pro
305                 310                 315

<210> SEQ ID NO 75
<211> LENGTH: 318
<212> TYPE: PRT
<213> ORGANISM: Homo sapiens

<400> SEQUENCE: 75

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
        35                  40                  45

Trp Ala Glu Asp Val Leu Gly Ala Glu Thr Trp Asp Thr Glu Thr Glu
50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asn Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Lys
                245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
        275                 280                 285

Tyr Val Ser Ala Ala Met Pro Cys Phe Val Ile Ile Ile Leu Cys
290                 295                 300

Val Pro Cys Cys Lys Lys Lys Thr Ser Ala Ala Glu Gly Pro
305                 310                 315

<210> SEQ ID NO 76
<211> LENGTH: 318
<212> TYPE: PRT
<213> ORGANISM: Homo sapiens
```

<400> SEQUENCE: 76

Glu Pro His Ser Leu Arg Tyr Asn Leu Met Val Leu Ser Gln Asp Gly
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Ala Lys Pro Gln Gly Gln
        35                  40                  45

Trp Ala Glu Asp Val Leu Gly Ala Glu Thr Trp Asp Thr Glu Thr Glu
    50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys
                85                  90                  95

Glu Ile His Glu Asp Ser Ser Thr Arg Gly Ser Arg His Phe Tyr Tyr
            100                 105                 110

Asn Gly Glu Leu Phe Leu Ser Gln Asn Leu Glu Thr Gln Glu Ser Thr
        115                 120                 125

Val Pro Gln Ser Ser Arg Ala Gln Thr Leu Ala Met Asn Val Thr Asn
130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
            180                 185                 190

Val Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
    210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
            260                 265                 270

Pro Ser Gly Lys Ala Leu Val Leu Gln Ser Gln Arg Thr Asp Phe Pro
        275                 280                 285

Tyr Val Ser Ala Ala Met Pro Cys Phe Val Ile Ile Ile Leu Cys
    290                 295                 300

Val Pro Cys Cys Lys Lys Lys Thr Ser Ala Ala Glu Gly Pro
305                 310                 315

<210> SEQ ID NO 77
<211> LENGTH: 171
<212> TYPE: PRT
<213> ORGANISM: Homo sapiens

<400> SEQUENCE: 77

His Ser Leu Arg Tyr Asn Leu Thr Val Leu Ser Gly Asp Gly Ser Val
1               5                   10                  15

Gln Ser Gly Phe Leu Ala Glu Val His Leu Asp Gly Gln Pro Phe Leu
            20                  25                  30

Arg Cys Asp Arg Gln Lys Cys Arg Ala Lys Pro Gln Gly Gln Trp Ala
        35                  40                  45

```
Glu Asp Val Leu Gly Asn Lys Thr Trp Asp Arg Glu Thr Arg Asp Leu
 50                  55                  60
Thr Gly Asn Gly Lys Asp Leu Arg Met Thr Leu Ala His Ile Lys Asp
 65                  70                  75                  80
Gln Lys Glu Gly Leu His Ser Leu Gln Glu Ile Arg Val Cys Glu Ile
                 85                  90                  95
His Glu Asp Asn Ser Thr Arg Ser Ser Gln His Phe Tyr Tyr Asp Gly
             100                 105                 110
Glu Leu Phe Leu Ser Gln Asn Leu Glu Thr Glu Trp Thr Met Pro
         115                 120                 125
Gln Ser Ser Arg Ala Gln Thr Leu Ala Met Asn Val Arg Asn Phe Leu
130                 135                 140
Lys Glu Asp Ala Met Lys Thr Lys Thr His Tyr His Ala Met His Ala
145                 150                 155                 160
Asp Cys Leu Gln Glu Leu Arg Arg Tyr Leu Lys
                165                 170

<210> SEQ ID NO 78
<211> LENGTH: 169
<212> TYPE: PRT
<213> ORGANISM: Homo sapiens

<400> SEQUENCE: 78

His Cys Leu Cys Tyr Asp Phe Ile Ile Thr Pro Lys Ser Arg Pro Glu
 1                5                  10                  15
Pro Gln Trp Cys Glu Val Gln Gly Leu Val Asp Glu Arg Pro Phe Leu
             20                  25                  30
His Tyr Asp Cys Val Asn His Lys Ala Lys Ala Phe Ala Ser Leu Gly
         35                  40                  45
Lys Lys Val Asn Val Thr Lys Thr Trp Glu Glu Gln Thr Glu Thr Leu
 50                  55                  60
Arg Asp Val Val Asp Phe Leu Lys Gly Gln Leu Leu Asp Ile Gln Val
 65                  70                  75                  80
Glu Asn Leu Ile Pro Ile Glu Pro Leu Thr Leu Gln Ala Arg Met Ser
                 85                  90                  95
Cys Glu His Glu Ala His Gly His Gly Arg Gly Ser Trp Gln Phe Leu
             100                 105                 110
Phe Asn Gly Gln Lys Phe Leu Leu Phe Asp Ser Asn Asn Arg Lys Trp
         115                 120                 125
Thr Ala Leu His Pro Gly Ala Lys Lys Met Thr Glu Lys Trp Glu Lys
130                 135                 140
Asn Arg Asp Val Thr Met Phe Phe Gln Lys Ile Ser Leu Gly Asp Cys
145                 150                 155                 160
Lys Met Trp Leu Glu Glu Phe Leu Met
                165

<210> SEQ ID NO 79
<211> LENGTH: 169
<212> TYPE: PRT
<213> ORGANISM: Homo sapiens

<400> SEQUENCE: 79

His Ser Leu Cys Tyr Asp Ile Thr Val Ile Pro Lys Phe Arg Pro Gly
 1                5                  10                  15
Pro Arg Trp Cys Ala Val Gln Gly Gln Val Asp Glu Lys Thr Phe Leu
             20                  25                  30
```

His Tyr Asp Cys Gly Asn Lys Thr Val Thr Pro Val Ser Pro Leu Gly
             35                  40                  45

Lys Lys Leu Asn Val Thr Thr Ala Trp Lys Ala Gln Asn Pro Val Leu
 50                  55                  60

Arg Glu Val Val Asp Ile Leu Thr Glu Gln Leu Arg Asp Ile Gln Leu
 65                  70                  75                  80

Glu Asn Tyr Thr Pro Lys Glu Pro Leu Thr Leu Gln Ala Arg Met Ser
                 85                  90                  95

Cys Glu Gln Lys Ala Glu Gly His Ser Ser Gly Ser Trp Gln Phe Ser
                100                 105                 110

Phe Asp Gly Gln Ile Phe Leu Leu Phe Asp Ser Glu Lys Arg Met Trp
            115                 120                 125

Thr Thr Val His Pro Gly Ala Arg Lys Met Lys Glu Lys Trp Glu Asn
    130                 135                 140

Asp Lys Val Val Ala Met Ser Phe His Tyr Phe Ser Met Gly Asp Cys
145                 150                 155                 160

Ile Gly Trp Leu Glu Asp Phe Leu Met
                165

<210> SEQ ID NO 80
<211> LENGTH: 169
<212> TYPE: PRT
<213> ORGANISM: Homo sapiens

<400> SEQUENCE: 80

His Ser Leu Trp Tyr Asn Phe Thr Ile Ile His Leu Pro Arg His Gly
1                5                  10                  15

Gln Gln Trp Cys Glu Val Gln Ser Gln Val Asp Gln Lys Asn Phe Leu
             20                  25                  30

Ser Tyr Asp Cys Gly Ser Asp Lys Val Leu Ser Met Gly His Leu Glu
             35                  40                  45

Glu Gln Leu Tyr Ala Thr Asp Ala Trp Gly Lys Gln Leu Glu Met Leu
 50                  55                  60

Arg Glu Val Gly Gln Arg Leu Arg Leu Glu Leu Ala Asp Thr Glu Leu
 65                  70                  75                  80

Glu Asp Phe Thr Pro Ser Gly Pro Leu Thr Leu Gln Val Arg Met Ser
                 85                  90                  95

Cys Glu Cys Glu Ala Asp Gly Tyr Ile Arg Gly Ser Trp Gln Phe Ser
                100                 105                 110

Phe Asp Gly Arg Lys Phe Leu Leu Phe Asp Ser Asn Asn Arg Lys Trp
            115                 120                 125

Thr Val Val His Ala Gly Ala Arg Arg Met Lys Glu Lys Trp Glu Lys
    130                 135                 140

Asp Ser Gly Leu Thr Thr Phe Phe Lys Met Val Ser Met Arg Asp Cys
145                 150                 155                 160

Lys Ser Trp Leu Arg Asp Phe Leu Met
                165

<210> SEQ ID NO 81
<211> LENGTH: 168
<212> TYPE: PRT
<213> ORGANISM: Homo sapiens

<400> SEQUENCE: 81

His Ser Leu Cys Phe Asn Phe Thr Ile Lys Ser Leu Ser Arg Pro Gly
1                5                  10                  15

-continued

Gln Pro Trp Cys Glu Ala Gln Val Phe Leu Asn Lys Asn Leu Phe Leu
            20                  25                  30

Gln Tyr Asn Ser Asp Asn Asn Met Val Lys Pro Leu Gly Leu Leu Gly
        35                  40                  45

Lys Lys Val Tyr Ala Thr Ser Thr Trp Gly Glu Leu Thr Gln Thr Leu
50                  55                  60

Gly Glu Val Gly Arg Asp Leu Arg Met Leu Leu Cys Asp Ile Lys Pro
65                  70                  75                  80

Gln Ile Lys Thr Ser Asp Pro Ser Thr Leu Gln Val Glu Met Phe Cys
                85                  90                  95

Gln Arg Glu Ala Glu Arg Cys Thr Gly Ala Ser Trp Gln Phe Ala Thr
            100                 105                 110

Asn Gly Glu Lys Ser Leu Leu Phe Asp Ala Met Asn Met Thr Trp Thr
        115                 120                 125

Val Ile Asn His Glu Ala Ser Lys Ile Lys Glu Thr Trp Lys Lys Asp
130                 135                 140

Arg Gly Leu Glu Lys Tyr Phe Arg Lys Leu Ser Lys Gly Asp Cys Asp
145                 150                 155                 160

His Trp Leu Arg Glu Phe Leu Gly
                165

<210> SEQ ID NO 82
<211> LENGTH: 169
<212> TYPE: PRT
<213> ORGANISM: Homo sapiens

<400> SEQUENCE: 82

His Ser Leu Cys Tyr Asp Ile Thr Val Ile Pro Lys Phe Arg Pro Gly
1               5                   10                  15

Pro Arg Trp Cys Ala Val Gln Gly Gln Val Asp Glu Lys Thr Phe Leu
            20                  25                  30

His Tyr Asp Cys Gly Ser Lys Thr Val Thr Pro Val Ser Pro Leu Gly
        35                  40                  45

Lys Lys Leu Asn Val Thr Thr Ala Trp Lys Ala Gln Asn Pro Val Leu
50                  55                  60

Arg Glu Val Val Asp Ile Leu Thr Glu Gln Leu Leu Asp Ile Gln Leu
65                  70                  75                  80

Glu Asn Tyr Ile Pro Lys Glu Pro Leu Thr Leu Gln Ala Arg Met Ser
                85                  90                  95

Cys Glu Gln Lys Ala Glu Gly His Gly Ser Gly Ser Trp Gln Leu Ser
            100                 105                 110

Phe Asp Gly Gln Ile Phe Leu Leu Phe Asp Ser Glu Asn Arg Met Trp
        115                 120                 125

Thr Thr Val His Pro Gly Ala Arg Lys Met Lys Glu Lys Trp Glu Asn
        130                 135                 140

Asp Lys Asp Met Thr Met Ser Phe His Tyr Ile Ser Met Gly Asp Cys
145                 150                 155                 160

Thr Gly Trp Leu Glu Asp Phe Leu Met
                165

<210> SEQ ID NO 83
<211> LENGTH: 169
<212> TYPE: PRT
<213> ORGANISM: Homo sapiens

<400> SEQUENCE: 83

-continued

```
His Ser Leu Cys Tyr Asp Ile Thr Val Ile Pro Lys Phe Arg Pro Gly
1               5                   10                  15

Pro Arg Trp Cys Ala Val Gln Gly Gln Val Asp Glu Lys Thr Phe Leu
            20              25                  30

His Tyr Asp Cys Gly Asn Lys Thr Val Thr Pro Val Ser Pro Leu Gly
            35              40              45

Lys Lys Leu Asn Val Thr Thr Ala Trp Lys Ala Gln Asn Pro Val Leu
        50              55              60

Arg Glu Val Val Asp Ile Leu Thr Glu Gln Leu Leu Asp Ile Gln Leu
65              70              75              80

Glu Asn Tyr Thr Pro Lys Glu Pro Leu Thr Leu Gln Ala Arg Met Ser
                85              90              95

Cys Glu Gln Lys Ala Glu Gly His Ser Ser Gly Ser Trp Gln Phe Ser
            100             105             110

Ile Asp Gly Gln Thr Phe Leu Leu Phe Asp Ser Glu Lys Arg Met Trp
            115             120             125

Thr Thr Val His Pro Gly Ala Arg Lys Met Lys Glu Lys Trp Glu Asn
    130             135             140

Asp Lys Asp Val Ala Met Ser Phe His Tyr Ile Ser Met Gly Asp Cys
145             150             155             160

Ile Gly Trp Leu Glu Asp Phe Leu Met
                165
```